United States Patent
Gajewski et al.

(10) Patent No.: US 10,753,938 B2
(45) Date of Patent: Aug. 25, 2020

(54) BETA-CATENIN INHIBITORS IN CANCER IMMUNOTHERAPY

(71) Applicant: The University of Chicago, Chicago, IL (US)

(72) Inventors: Thomas Gajewski, Chicago, IL (US); Stefani Spranger, Chicago, IL (US)

(73) Assignee: The University of Chicago, Chicago, IL (US)

( * ) Notice: Subject to any disclaimer, the term of this patent is extended or adjusted under 35 U.S.C. 154(b) by 150 days.

(21) Appl. No.: 15/555,099

(22) PCT Filed: Mar. 4, 2016

(86) PCT No.: PCT/US2016/020944
§ 371 (c)(1),
(2) Date: Sep. 1, 2017

(87) PCT Pub. No.: WO2016/141312
PCT Pub. Date: Sep. 9, 2016

(65) Prior Publication Data
US 2018/0038868 A1   Feb. 8, 2018

Related U.S. Application Data

(60) Provisional application No. 62/128,285, filed on Mar. 4, 2015.

(51) Int. Cl.
| | |
|---|---|
| *G01N 33/574* | (2006.01) |
| *C07K 16/28* | (2006.01) |
| *A61K 39/395* | (2006.01) |
| *G01N 33/50* | (2006.01) |
| *A61K 35/15* | (2015.01) |
| *A61K 35/17* | (2015.01) |
| *A61K 45/06* | (2006.01) |
| *C12Q 1/6886* | (2018.01) |
| *C12N 15/113* | (2010.01) |

(52) U.S. Cl.
CPC ....... *G01N 33/57496* (2013.01); *A61K 35/15* (2013.01); *A61K 35/17* (2013.01); *A61K 39/395* (2013.01); *A61K 39/3955* (2013.01); *A61K 39/39558* (2013.01); *A61K 45/06* (2013.01); *C07K 16/2818* (2013.01); *C07K 16/2827* (2013.01); *C12Q 1/6886* (2013.01); *G01N 33/5017* (2013.01); *G01N 33/57484* (2013.01); *G01N 33/57492* (2013.01); *C12N 15/113* (2013.01); *C12N 2310/14* (2013.01); *C12Q 2600/158* (2013.01); *G01N 2333/4706* (2013.01); *G01N 2333/70517* (2013.01)

(58) Field of Classification Search
None
See application file for complete search history.

(56) References Cited

U.S. PATENT DOCUMENTS

| | | | |
|---|---|---|---|
| 4,946,778 A | 8/1990 | Ladner et al. | |
| 5,260,203 A | 11/1993 | Ladner et al. | |
| 6,066,500 A | 5/2000 | Bennett et al. | |
| 8,815,825 B2 * | 8/2014 | Brown | C12N 15/113 514/44 A |
| 2013/0039998 A1 | 2/2013 | Fass et al. | |
| 2014/0288174 A1 | 9/2014 | Lee et al. | |

FOREIGN PATENT DOCUMENTS

| | | |
|---|---|---|
| CN | 201210490539 | 6/2014 |
| EP | 0265244 | 9/1992 |
| WO | WO 88/01649 | 3/1988 |
| WO | WO 2012/018754 | 2/2012 |
| WO | WO 2014/061828 | 4/2014 |

OTHER PUBLICATIONS

Lin et al. (PNAS, 97(8): 4262-4266, 2000).*
Callahan et al. (Semin Oncol, 37: 473-484, 2010).*
Spranger et al. (Journal of ImmunoTherapy of Cancer, 3(43): 1-3, 2015).*
Aliberti et al., CCR5 provides a signal for microbial induced production of IL-12 by CD8 alpha+ dendritic cells. Nat Immunol. Jul. 2000;1(1):83-7.
Bedoui et al., Cross-presentation of viral and self antigens by skin-derived CD103+ dendritic cells. Nat Immunol. May 2009;10(5):488-95.
Bosenberg et al., Characterization of melanocyte-specific inducible Cre recombinase transgenic mice. Genesis. May 2006;44(5):262-7.
Cheung et al., Regulated expression of a tumor-associated antigen reveals multiple levels of T-cell tolerance in a mouse model of lung cancer. Cancer Res. Nov. 15, 2008;68(22):9459-68.
Chien et al., Activated Wnt/beta-catenin signaling in melanoma is associated withdecreased proliferation in patient tumors and a murine melanoma model. Proceedings ofthe National Academy of Sciences of the United States of America. Jan. 27, 2009;106(4):1193-8.
Cipponi et al., Tumor-infiltrating lymphocytes: apparently good for melanoma patients. But why? Cancer Immunology, Immunotherapy. Aug. 2011;60(8):1153-60.
Clackson et al., Making antibody fragments using phage display libraries. Nature. Aug. 15, 1991;352(6336):624-8.

(Continued)

*Primary Examiner* — Nelson B Moseley, II
(74) *Attorney, Agent, or Firm* — Casimir Jones SC; David W. Staple

(57) ABSTRACT

Provided herein are compositions and methods for the treatment of cancer by inhibition of β-catenin or a β-catenin pathway. In particular, inhibitors of β-catenin and/or the Wnt/p-catenin signaling pathway are employed prevent or reverse evasion of immune response or immunotherapy by cancers.

15 Claims, 43 Drawing Sheets

Specification includes a Sequence Listing.

(56) References Cited

OTHER PUBLICATIONS

Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80.

Damksy et al., β-catenin signaling controls metastasis in Braf-activated Pten-deficient melanomas. Cancer Cell. Dec. 13, 2011;20(6):741-54.

Dankort et al., Braf(V600E) cooperates with Pten loss to induce metastatic melanoma. Nature genetics. May 2009;41(5):544-52.

Dankort et al., A new mouse model to explore the initiation, progression, and therapy of BRAFV600E-induced lung tumors. Genes & development. Feb. 15, 2007;21(4):379-84.

Driessens et al., Beta-catenin inhibits T cell activation by selective interference withlinker for activation of T cells-phospholipase C-gamma1 phosphorylation. Journal of Immunology. Jan. 15, 2011;186(2):784-90.

Driessens et al., Beta-catenin does not regulate memory T cellphenotype. Nature Medicine. May 16, 2010(5):513-4.

Dupage et al.,Endogenous T cell responses to antigens expressed in lung adenocarcinomas delay malignant tumor progression. Cancer cell. Jan. 18, 2011;19(1):72-85.

Edelson et al., Peripheral CD103+ dendritic cells form a unified subset developmentally related to CD8alpha+ conventional dendritic cells. The Journal of Experimental Medicine. Apr. 12, 2010;207(4):823-36.

Engelhardt et al., Marginating dendritic cells of the tumor microenvironment cross-present tumor antigens and stably engage tumor-specific T cells. Cancer cell. Mar. 20, 2012;21(3):402-17.

Erdag et al., Immunotype and immunohistologic characteristics of tumor-infiltratingimmune cells are associated with clinical outcome in metastatic melanoma. Cancer Research. Mar. 1, 2012;72(5):1070-80.

Fuertes et al., Host type I IFN signals are required for antitumor CD8+ T cell responses through CD8{alpha}+ dendritic cells. J Exp Med. Sep. 26, 2011;208(10):2005-16.

Fundamental Immunology (1989) Ch. 7 Paul, W., ed., 2nd ed. Raven Press, N.Y.

Gajewski et al., Gene signature in melanoma associated with clinical activity: a potential clue to unlock cancer immunotherapy. Cancer J. Jul.-Aug. 2010;16(4):399-403.

Gajewski et al., Cancer immunotherapy strategies based on overcoming barriers within the tumor microenvironment. Curr Opin Immunol. Apr. 2013;25(2):268-76.

Gajewski et al., Innate and adaptive immune cells in the tumormicroenvironment. Nature Immunology. Oct. 2013;14(10):1014-22.

Galon et al., Type, density, and location of immune cells within human colorectal tumors predict clinical outcome. Science. Sep. 29, 2006;313(5795):1960-4.

Genomes Project et al., An integrated map of genetic variation from 1,092 humangenomes. Nature. Nov. 1, 2012;491(7422):56-65.

Gounari et al., Stabilization of beta-catenin induces lesions reminiscent of prostatic intraepithelial neoplasia, but terminal squamous transdifferentiation of other secretory epithelia. Oncogene 21. Jun. 13, 2002;21(26):4099-107.

Harada et al., Intestinal polyposis in mice with a dominant stable mutation of the beta-catenin gene. The EMBO Journal. Nov. 1, 1999;18(21):5931-42.

Harlin et al., Chemokine expression in melanoma metastases associated with CD8+ T-cell recruitment. Cancer Res. Apr. 1, 2009;69(7):3077-85.

Harlow, et al. Antibodies: A Laboratory Manual Ch. 6, (Cold Spring Harbor Laboratory, Cold Spring Harbor, N.Y.) 1988.

Herbst et al., Comprehensive analysis of beta-catenin target genes in colorectalcarcinoma cell lines with deregulated Wnt/beta-catenin signaling. BMC Genomics. Jan. 28, 2014;15:74.

Hildner et al., Batf3 deficiency reveals a critical role for CD8alpha+ dendritic cells in cytotoxic T cell immunity. Science. Nov. 14, 2008;322(5904):1097-100.

Hodi et al., Improved Survival with Ipilimumab in Patients with Metastatic Melanoma. N Engl J Med. Aug. 19, 2010;393(8):711-723.

Huang et al., ShRNA-mediated gene silencing of beta-catenin inhibits growth of human colon cancer cells. World J Gastroenterol. Dec. 28, 2007;13(48):6581-7.

Hudson et al., Engineered antibodies. Nat Med. Jan. 2003;9(1):129-34.

Jensen et al., STRING 8—a global view on proteins and their functional interactionsin 630 organisms. Nucleic Acids Research. Jan. 2009;37(Database issue):D412-6.

Jeong et al., Hedgehog signalingin the neural crest cells regulates the patterning and growth of facial primordia. Genes &Development. Apr. 15, 2004;18(8):937-51.

Ji et al., An immune-active tumor microenvironment favors clinical response to ipilimumab. Cancer Immunol Immunother. Jul. 2012;61(7):1019-31.

Jongbloed et al., Human CD141+ (BDCA-3)+ dendritic cells (DCs) represent aunique myeloid DC subset that cross-presents necrotic cell antigens. The Journal of Experimental Medicine. Jun. 7, 2010;207(6):1247-60.

Kaufman et al., The Society for Immunotherapy of Cancer consensus statement on tumour immunotherapy for the treatment of cutaneous melanoma. Nature Reviews Clinical Oncology. Oct. 2013;10(10):588-98.

Kawakami et al., Improvement of cancer immunotherapy by combining molecular targeted therapy. Front Oncol. May 28, 2013;3:136.

Khuu et al., Activating transcription factor 3(ATF3) represses the expression of CCL4 in murine macrophages. MolecularImmunology. Mar. 2007;44(7):1598-605.

Landsberg et al., Melanomas resist T-cell therapy through inflammation-induced reversible dedifferentiation. Nature. Oct. 18, 2012;490(7420):412-6.

Li et al., RSEM: accurate transcript quantification from RNA-Seq data with or without a reference genome. BMC Bioinformatics. Aug. 4, 2011;12:323.

Li et al., N-myc downstream-regulated gene 2, a novel estrogen-targeted gene, is involved in the regulation of Na+/K+−ATPase. The Journal of Biological Chemistry. Sep. 16, 2011;286(37):32289-99.

Malissen et al., The origins and functions of dendritic cells and macrophages in the skin. Nature Reviews Immunology. Jun. 2014;14(6):417-28.

Manning et al., Antigen recognition and allogeneic tumor rejection in CD8+ TCR transgenic/RAG(−/−) mice. Journal of immunology. Nov. 15, 1997;159(10):4665-75.

Marks et al., By-passing immunization. Human antibodies from V-gene libraries displayed on phage. Journal of Molecular Biology. Dec. 5, 1991;222(3):581-97.

Matsushita et al., Cancer exome analysis reveals a T-cell-dependent mechanism ofcancer immunoediting. Nature. Feb. 8, 2012;482(7385):400-4.

Meijering et al., Methods for cell and particle tracking. Methods in Enzymology. 2012;504:183-200.

Mellman et al., Cancer immunotherapy comes of age. Nature. Dec. 21, 2011;480(7378):480-9.

Mollah et al., Flt3L dependence helps define an uncharacterized subset of murine cutaneous dendritic cells. The Journal of Investigative Dermatology. May 2014;134(5):1265-1275.

Molon et al., Chemokine nitration prevents intratumoral infiltration of antigen-specificT cells. The Journal of Experimental Medicine. Sep. 26, 2011;208(10):1949-62.

Nelson et al., The impact of T-cell immunity on ovarian cancer outcomes. Immunological Reviews. Apr. 2008;222:101-16.

Ott et al., CTLA-4 and PD-1/PD-L1 blockade: new immunotherapeutic modalities with durable clinical benefit in melanoma patients. Clin Cancer Res. Oct. 1, 2013;19(19):5300-9.

Peng et al., PD-1 blockade enhances T-cell migration to tumors by elevating IFN-γ inducible chemokines. Cancer Research. Oct. 15, 2012;72(20):5209-18.

Rimm et al., Frequent nuclear/cytoplasmic localization of beta-catenin without exon 3 mutations in malignant melanoma. The American Journal of Pathology. Feb. 1999;154(2):325-9.

(56) References Cited

OTHER PUBLICATIONS

Salerno et al., T cells in the human metastatic melanoma microenvironment express site-specific homing receptors and retention integrins. Journal International du Cancer. Feb. 1, 2014;134(3):563-74.
Sato et al., Intraepithelial CD8+ tumor-infiltrating lymphocytes and a highCD8+/regulatory T cell ratio are associated with favorable prognosis in ovarian cancer. Proceedings of the National Academy of Sciences of the United States of America. Dec. 20, 2005;102(51):18538-43. Epub Dec. 12, 2005
Schmittgen et al., Analyzing real-time PCR data by the comparative C(T)method. Nature Protocols. 2008;3(6):1101-8.
Soudja et al., Tumor-initiated inflammation overrides protective adaptive immunity in an induced melanoma model in mice. Cancer Research. May 1, 2010;70(9):3515-25.
Spranger et al., Generation of Th1-polarizing dendritic cells using the TLR7/8 agonistCL075. Journal of Immunology. Jul. 1, 2010;185(1):738-47.
Spranger et al., Up-regulation of PD-L1, IDO, and T(regs) in the melanoma tumor microenvironment is driven by CD8(+) T cells. Sci Transl Med. Aug. 28, 2013;5(200):200ra116.
Spranger et al., Mechanism of tumor rejection with doublets of CTLA-4, PD-1/PD-L1, or IDO blockade involves restored IL-2 production and proliferation of CD8+ T cells directly within the tumor microenvironment. Journal of ImmunoTherapy of Cancer. Feb. 18, 2014;2:3.
Spranger et al., Melanoma-intrinstic beta-catenin signaling prevents T cell inflitration and anti-tumor immunity. Journal of ImmunoTherapy of Cancer. 2014;2(Suppl 3):O15.
Spranger et al., Melanoma-intrinsic β-catenin signalling prevents anti-tumour immunity. Nature. Jul. 9, 2015;523(7559):231-5.

Suzuki et al., High cancer susceptibility and embryonic lethality associated with mutation of the PTEN tumor suppressor gene in mice. Current Biology. Oct. 22, 1998;8(21):1169-78.
Topalian et al., Survival, durable tumor remission, and long-term safety in patients with advanced melanoma receiving nivolumab. J Clin Oncol. Apr. 1, 2014;32(10):1020-30.
Topalian et al., Safety, activity, and immune correlates of anti-PD-1 antibody in cancer. N Engl J Med. Jun. 28, 2012;366(26):2443-54.
Wang et al., ANNOVAR: functional annotation of genetic variants from high-throughput sequencing data. Nucleic Acids Research. Sep. 2010;38(16):e164.
Wilkerson et al., ConsensusClusterPlus: a class discovery tool with confidence assessments and item tracking. Bioinformatics 26. Jun. 15, 2010;26(12):1572-3.
Wolchok et al., Nivolumab plus ipilimumab in advanced melanoma. N Engl J Med. Jul. 11, 2013;369(2):122-33.
Woo et al., Immune inhibitory molecules LAG-3 and PD-1 synergistically regulateT-cell function to promote tumoral immune escape. Cancer Research. Feb. 15, 2012;72(4):917-27.
Yaguchi et al., Immune suppression and resistance mediated by constitutive activationof Wnt/beta-catenin signaling in human melanoma cells. Journal of Immunology. Sep. 1, 2012;189(5):2110-7.
Yee et al., Adoptive T cell therapy using antigen-specific CD8+ T cell clones for the treatment of patients with metastatic melanoma: in vivo persistence, migration, and antitumor effect of transferred T cells. Proc Natl Acad Sci U S A. Dec. 10, 2002;99(25):16168-73.
Extended European Search Report for EP16759593.3, dated Jun. 18, 2018, 11 pages.
International Search Report and Written Opinion for PCT/US2016/020944, dated May 31, 2016, 15 pages.

* cited by examiner a b c a b

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial sequence
<220> FEATURE:
<223> OTHER INFORMATION: DNA Primer

<400> SEQUENCE: 1
agcgaaggtt gtggatctgg                                                 20

<210> SEQ ID NO 2
<211> LENGTH: 19
<212> TYPE: DNA
<213> ORGANISM: Artificial sequence
<220> FEATURE:
<223> OTHER INFORMATION: DNA Primer

<400> SEQUENCE: 2
```
tgaccctgct tctgcttgt                                                19

<210> SEQ ID NO 3
<211> LENGTH: 19
<212> TYPE: DNA
<213> ORGANISM: Artificial sequence
<220> FEATURE:
<223> OTHER INFORMATION: DNA Primer

<400> SEQUENCE: 3
gtgaagttcg agggcgaca                                                19

<210> SEQ ID NO 4
<211> LENGTH: 20
<212> TYPE: DNA
<213> ORGANISM: Artificial sequence
<220> FEATURE:
<223> OTHER INFORMATION: DNA Primer

<400> SEQUENCE: 4
ggcgaggcgg tgttgtagct                                               20

<210> SEQ ID NO 5
<211> LENGTH: 20
<212> TYPE: DNA
<213> ORGANISM: Artificial sequence
<220> FEATURE:
<223> OTHER INFORMATION: DNA Primer

<400> SEQUENCE: 5
cggctaccac atccaaggaa                                               20

<210> SEQ ID NO 6
<211> LENGTH: 18
<212> TYPE: DNA
<213> ORGANISM: Artificial sequence
<220> FEATURE:
<223> OTHER INFORMATION: DNA Primer

<400> SEQUENCE: 6
tcggcgccat taaggtcg                                                 18

<210> SEQ ID NO 7
<211> LENGTH: 8
<212> TYPE: PRT
<213> ORGANISM: Artificial sequence
<220> FEATURE:
<223> OTHER INFORMATION: Model antigen SIY

<400> SEQUENCE: 7

Ser Ile Tyr Arg Tyr Tyr Gly Leu
1               5

<210> SEQ ID NO 8
<211> LENGTH: 8
<212> TYPE: PRT
<213> ORGANISM: Artificial sequence
<220> FEATURE:
<223> OTHER INFORMATION: Pentamer

<400> SEQUENCE: 8

Ser Ile Ile Asn Phe Glu Lys Leu
1               5

BETA-CATENIN INHIBITORS IN CANCER IMMUNOTHERAPY

FIELD

Provided herein are compositions and methods for the treatment of cancer by inhibition of β-catenin or a β-catenin pathway. In particular, inhibitors of β-catenin and/or the Wnt/β-catenin signaling pathway are employed prevent or reverse evasion of immune response or immunotherapy by cancers.

BACKGROUND

Cancer treatment, and melanoma treatment in particular, is being revolutionized by the development of effective immunotherapeutic approaches (Kaufman, H. L. et al. Nature reviews. Clinical oncology 10, 588-598 (2013); Mellman et al. Nature 480, 480-489 (2011).; herein incorporated by reference in their entireties). These strategies include blockade of immune-inhibitory receptors on activated T cells, for example using monoclonal antibodies (mAbs) against CTLA-4 and PD-1/PD-L1 (Wolchok, J. D. et al. The New England Journal of Medicine 369, 122-133 (2013); Topalian, S. L. et al. Journal of clinical oncology 32, 1020-1030 (2014); Topalian, S. L. et al. The New England journal of medicine 366, 2443-2454 (2012); Hodi, F. S. et al. The New England journal of medicine 363, 711-723 (2010); herein incorporated by reference in their entireties). However, only a subset of patients responds to these treatments, and data suggest that therapeutic benefit is preferentially achieved in patients who have a pre-existing T cell response against their tumor as evidenced by a baseline $CD8^+$ T cell-infiltration within the tumor-microenvironment (Harlin, H. et al. Cancer research 69, 3077-3085 (2009); Ji, R. R. et al. Cancer immunology, immunotherapy: CII 61, 1019-1031 (2012); Gajewski et al. Cancer journal 16, 399-403 (2010); herein incorporated by reference in their entireties). What is needed in the field is an understanding of the molecular mechanisms that underlie the presence or absence of a spontaneous anti-tumor T cell response in subsets of cases, and therapeutic solutions for patients lacking a T cell infiltrate.

SUMMARY

Provided herein are compositions and methods for the treatment of cancer by inhibition of β-catenin or a β-catenin pathway. In particular, inhibitors of β-catenin and/or the Wnt/β-catenin signaling pathway are employed prevent or reverse evasion of immune response or immunotherapy by cancers.

In some embodiments, provided herein are methods for the treatment of cancer comprising administering a β-catenin inhibitor or a Wnt/β-catenin pathway inhibitor to a subject suffering from cancer. In some embodiments, the subject suffers from a solid tumor cancer. In some embodiments, the subject suffers from melanoma. In some embodiments, the subject has one or more tumors exhibiting tumor-intrinsic-β-catenin-signaling. In some embodiments, methods further comprise a step of testing the subject, tumor, or a tumor cell for β-catenin-signaling. In some embodiments, the subject has one or more tumors that exclude T-cell infiltration. In some embodiments, the β-catenin inhibitor or a Wnt/β-catenin pathway inhibitor is selected from a groups consisting of a small molecule, a peptide, a polypeptide, a nucleic acid, an antibody, and an antibody fragment. In some embodiments, methods further comprise co-administration of an additional therapeutic agent. In some embodiments, the additional therapeutic agent is a chemotherapeutic or an immunotherapeutic agent. In some embodiments, the additional therapeutic agent comprises anti-CTLA-4 monoclonal antibodies and/or anti-PD-L1 or anti-PD-1 monoclonal antibodies.

In some embodiments, provided herein are methods of treating a subject with an immunotherapeutic-resistant tumor, comprising: (a) testing tumor cells or tissue for one or more of: (i) tumor-intrinsic-β-catenin-signaling, (ii) exclusion of T cell infiltration, (iii) transcriptional repression of chemokine CCL4, (iv) defective recruitment of $CD103^+$ dermal dendritic cells, and (v) activation of $CD8^+$ T cells; and (b) co-administering to the subject a β-catenin inhibitor or a Wnt/β-catenin pathway inhibitor and an immunotherapeutic agent. In some embodiments, methods further comprise surgical, radiation, and/or chemotherapeutic cancer interventions.

In some embodiments, provided herein are methods of treating a subject with an immunotherapeutic-resistant tumor, comprising: (a) testing tumor cells or tissue for one or more of: (i) tumor-intrinsic-β-catenin-signaling, (ii) exclusion of T cell infiltration, (iii) transcriptional repression of chemokine CCL4, (iv) defective recruitment of $CD103^+$ dermal dendritic cells, and (v) activation of $CD8^+$ T cells; and (b) if the subject tests positive for at least one of (i) through (v), administering to the subject a β-catenin inhibitor or a Wnt/β-catenin pathway inhibitor. In some embodiments, methods further comprise (c) retesting the subject for one or more of (i) through (v). In some embodiments, if the subject tests negative in step (c) for one or more or (i) through (v) that were positive in step (a), an immunotherapeutic agent is administered to the subject. In some embodiments, methods further comprise testing the subject for one or more additional cancer biomarkers.

In some embodiments, provided herein are methods comprising: (a) testing sample cells from a cell population to determine whether Wnt/β-catenin signaling is active in said cell population; (b) administering an inhibitor of Wnt/β-catenin signaling to said cell population if said sample cells test positive for Wnt/β-catenin signaling. In some embodiments, the testing is performed in vitro. In some embodiments, the inhibitor of Wnt/β-catenin signaling is a β-catenin inhibitor or a Wnt/β-catenin pathway inhibitor. In some embodiments, methods further comprise administering an immunotherapeutic agent to said cell population. In some embodiments, the immunotherapeutic agent is an antibody. In some embodiments, the antibody is an anti-cancer or anti-tumor monoclonal antibody. In some embodiments, the antibody is an anti-PD-L1 or anti-PD-1 monoclonal antibody and/or an anti-CTLA-4 monoclonal antibody.

In some embodiments, provided herein are compositions comprising a β-catenin inhibitor and an immunotherapeutic agent, said composition formulated for therapeutic delivery to a subject. In some embodiments, provided herein are β-catenin inhibitors or a Wnt/β-catenin pathway inhibitors for use as a medicament in the inhibition of tumor-intrinsic β-catenin-signaling. In some embodiments, provided herein are β-catenin inhibitors or a Wnt/β-catenin pathway inhibitors for use as a medicament in the treatment of tumor exclusion of T cell infiltration.

In some embodiments, provided herein are methods of diagnosing a subject as having an immunotherapeutic-resistant tumor, comprising testing tumor cells or tissue for one or more of: (i) tumor-intrinsic β-catenin-signaling, (ii)

exclusion of T cell infiltration, (iii) transcriptional repression of chemokine CCL4, (iv) defective recruitment of CD103+ dendritic cells, and (v) activation of CD8+ T cells; wherein a positive indication for at least one of (i) through (v) indicates that the subject has an immunotherapeutic-resistant tumor. In some embodiments, methods further comprise testing the subject for one or more additional cancer biomarkers. In some embodiments, testing comprises contacting a sample from said tumor cells or tissue with one or more diagnostic reagents. In some embodiments, the sample is a processed sample. In some embodiments, diagnostic reagents comprise primers, probes, antibodies, antibody fragments, and/or aptamers. In some embodiments, an immunotherapeutic-resistant tumor is resistant to treatment with one or more of anti-CTLA-4, anti-PD-L1, and anti-PD-1 antibodies.

DEFINITIONS

Figure 1:
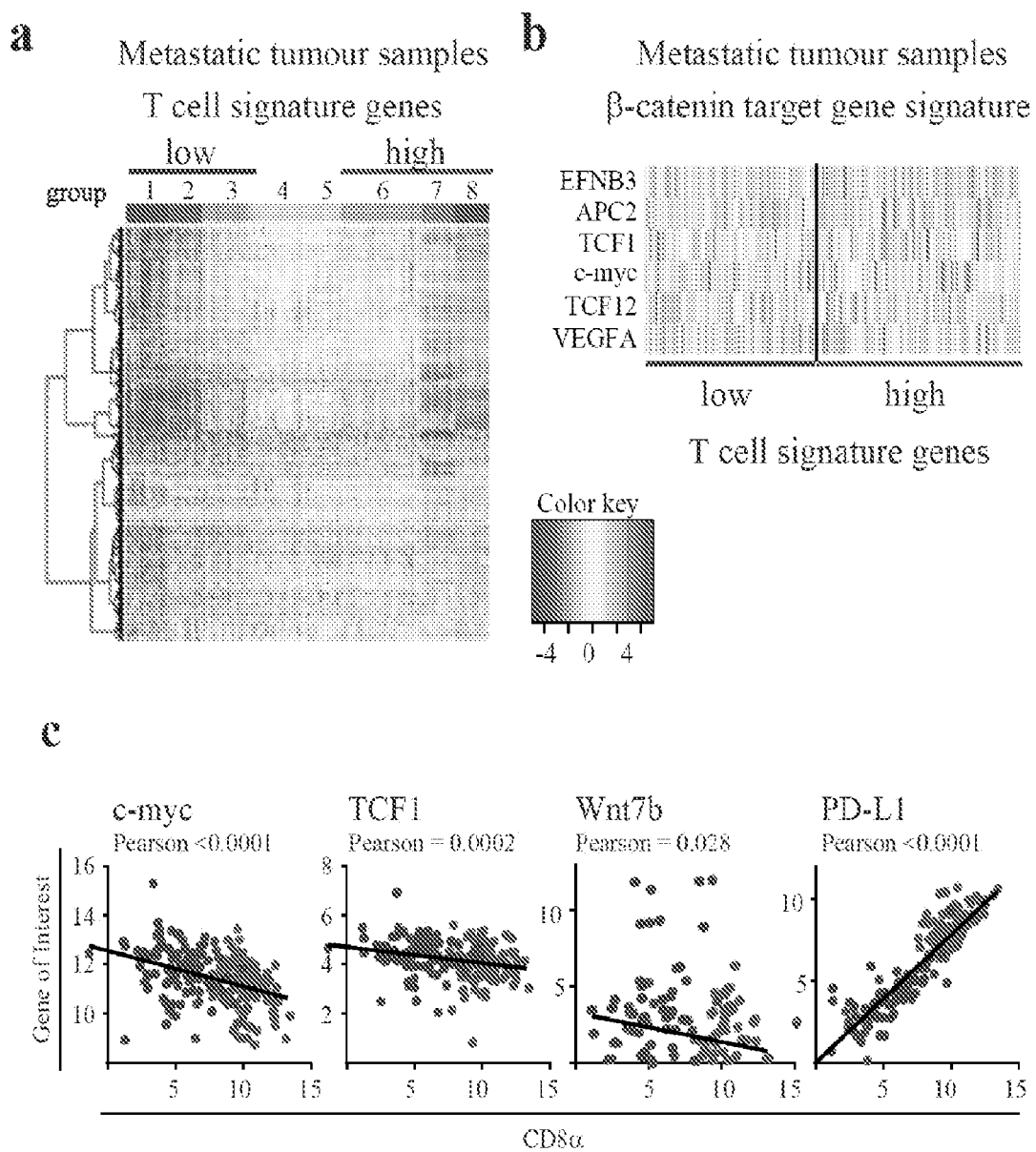
FIG. 1A-G. Melanoma-intrinsic β-catenin pathway activation correlates with T cell exclusion. (a) Heat-map of 266 metastatic human melanomas clustered in T cell-signature gene low versus high. (b) Heat-map of β-catenin target genes within the T cell-signature high and low cohorts. (c) Pearson-correlation of CD8α expression with c-myc, TCF1, Wnt7b. (d) Correlation between β-catenin staining and CD8 staining in biopsies from melanoma patients. (e) tumor incidence rates of GEMs (median time to tumor event): $Braf^{V600E}/PTEN^{-/-}$: 100%, 21 days; $Braf^{V600E}/CAT\text{-}STA$: 85%, 55.5 days; $Braf^{V600E}/PTEN^{-/-}/CAT\text{-}STA$: 100%, 26 days. (f) Amount of CD3+ T cells depicted as % living cells and absolute numbers/gram tumor. (g) Fluorescent immunohistochemistry staining against CD3+ T cells (scale bars 100 $\alpha\mu$).
Figure 1:
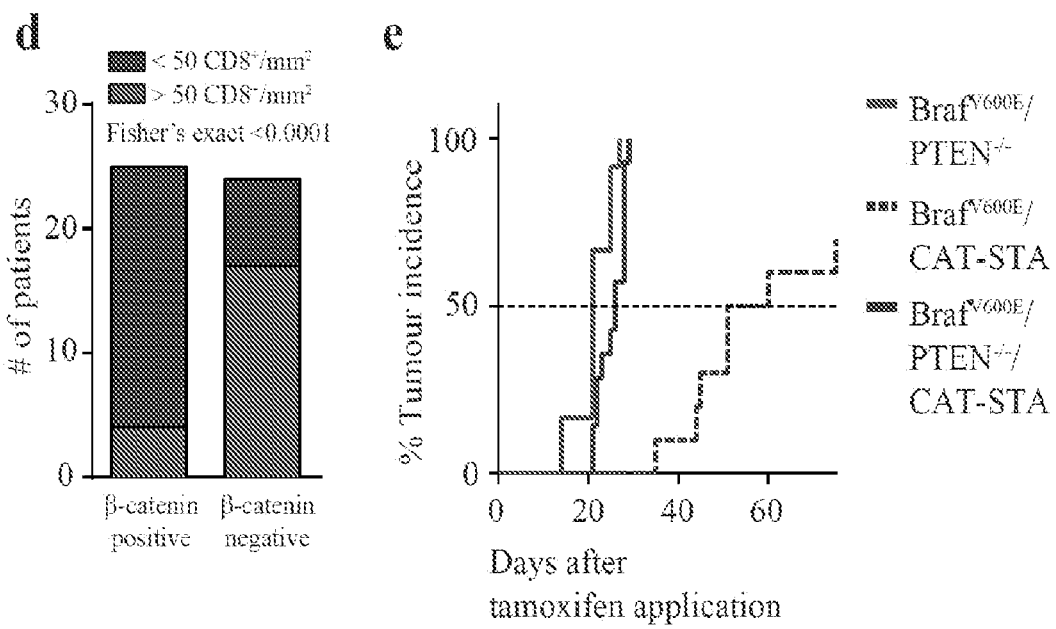
Figure 1:
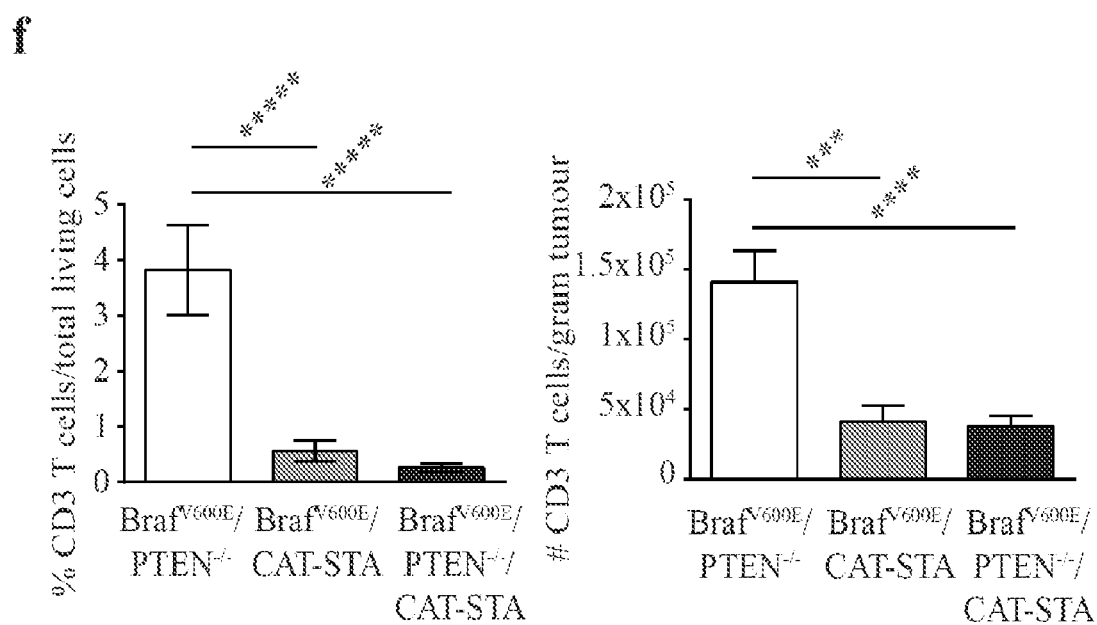
Figure 1:
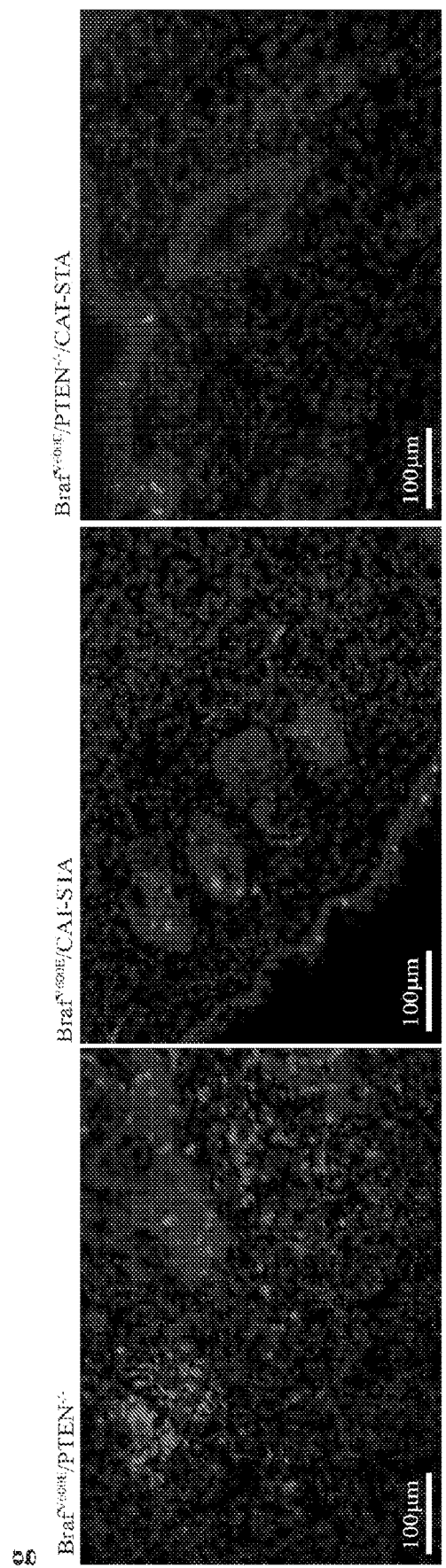

As used herein, the term "β-catenin inhibitor" refers to an agent (e.g., small molecule, peptide, antibody, antibody fragment, aptamer, nucleic acid, etc.) that prevents or reduced signal transduction by β-catenin. A β-catenin inhibitor may function by any suitable mechanism, including but not limited to reducing/inhibiting expression of β-catenin (e.g., RNAi, antisense RNA, etc.), sequestering β-catenin (e.g., antibody), preventing interaction of β-catenin with other components of the cadherin protein complex, preventing interaction of β-catenin with binding partners, activation, overexpression, or upregulation of the β-catenin destruction complex, etc.

As used herein, the term "β-catenin pathway" (or "Wnt/β-catenin pathway") refers to the any signal transduction pathways upstream or downstream of β-catenin (e.g., including the Wnt signaling pathway), the activation or inhibition of which would alter the effect of β-catenin on the biological system.

As used herein, the term "β-catenin pathway inhibitor" (or "Wnt/β-catenin pathway inhibitor") refers to an agent (e.g., small molecule, peptide, antibody, antibody fragment, aptamer, nucleic acid, etc.) that interacts with a component of a β-catenin pathway, resulting in reduction or inhibition of the effect of β-catenin on the biological system. An inhibitor of β-catenin is but one example of a β-catenin pathway inhibitor.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition (e.g., cancer, solid tumor cancer, non-T cell-infiltrated tumor cancer, etc.).

As used herein, an "immune response" refers to the action of a cell of the immune system (e.g., T lymphocytes, B lymphocytes, natural killer (NK) cells, macrophages, eosinophils, mast cells, dendritic cells, neutrophils, etc.) and soluble macromolecules produced by any of these cells or the liver (including antibodies, cytokines, and complement) that results in selective targeting, binding to, damage to, destruction of, and/or elimination from a subject of invading pathogens, cells or tissues infected with pathogens, or cancerous or other abnormal cells.

As used herein, the term "immunoregulator" refers to a substance, an agent, a signaling pathway or a component thereof that regulates an immune response. "Regulating," "modifying" or "modulating" an immune response refers to any alteration in a cell of the immune system or in the activity of such cell. Such regulation includes stimulation or suppression of the immune system which may be manifested by an increase or decrease in the number of various cell types, an increase or decrease in the activity of these cells, or any other changes which can occur within the immune system. Both inhibitory and stimulatory immunoregulators have been identified, some of which may have enhanced function in the cancer microenvironment.

As used herein, the term "immunotherapy" refers to the treatment or prevention of a disease or condition by a method comprising inducing, enhancing, suppressing or otherwise modifying an immune response.

As used herein, "potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

As used herein, the term "antibody" refers to a whole antibody molecule or a fragment thereof (e.g., fragments such as Fab, Fab', and F(ab')$_2$), it may be a polyclonal or monoclonal antibody, a chimeric antibody, a humanized antibody, a human antibody, etc.

A native antibody typically has a tetrameric structure. A tetramer typically comprises two identical pairs of polypeptide chains, each pair having one light chain (in certain embodiments, about 25 kDa) and one heavy chain (in certain embodiments, about 50-70 kDa). In a native antibody, a heavy chain comprises a variable region, $V_H$, and three constant regions, $C_{H1}$, $C_{H2}$, and $C_{H3}$. The $V_H$ domain is at the amino-terminus of the heavy chain, and the $C_{H3}$ domain is at the carboxy-terminus. In a native antibody, a light chain comprises a variable region, $V_L$, and a constant region, $C_L$. The variable region of the light chain is at the amino-terminus of the light chain. In a native antibody, the variable regions of each light/heavy chain pair typically form the antigen binding site. The constant regions are typically responsible for effector function.

In a native antibody, the variable regions typically exhibit the same general structure in which relatively conserved framework regions (FRs) are joined by three hypervariable regions, also called complementarity determining regions (CDRs). The CDRs from the two chains of each pair typically are aligned by the framework regions, which may enable binding to a specific epitope. From N-terminus to C-terminus, both light and heavy chain variable regions typically comprise the domains FR1, CDR1, FR2, CDR2, FR3, CDR3 and FR4. The CDRs on the heavy chain are referred to as H1, H2, and H3, while the CDRs on the light chain are referred to as L1, L2, and L3. Typically, CDR3 is the greatest source of molecular diversity within the antigen-binding site. H3, for example, in certain instances, can be as short as two amino acid residues or greater than 26. The assignment of amino acids to each domain is typically in accordance with the definitions of Kabat et al. (1991) Sequences of Proteins of Immunological Interest (National Institutes of Health, Publication No. 91-3242, vols. 1-3, Bethesda, Md.); Chothia, C., and Lesk, A. M. (1987) J. Mol. Biol. 196:901-917; or Chothia, C. et al. Nature 342:878-883 (1989). In the present application, the term "CDR" refers to a CDR from either the light or heavy chain, unless otherwise specified.

As used herein, the term "heavy chain" refers to a polypeptide comprising sufficient heavy chain variable region sequence to confer antigen specificity either alone or in combination with a light chain.

As used herein, the term "light chain" refers to a polypeptide comprising sufficient light chain variable region sequence to confer antigen specificity either alone or in combination with a heavy chain.

As used herein, when an antibody or other entity "specifically recognizes" or "specifically binds" an antigen or epitope, it preferentially recognizes the antigen in a complex mixture of proteins and/or macromolecules, and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant ($K_a$) of at least $10^7$ $M^{-1}$ (e.g., $>10^7 M^{-1}$, $>10^8 M^{-1}$, $>10^9 M^{-1}$, $>10^{10} M^{-1}$, $>10^{11} M^{-1}$, $>10^{12} M^{-1}$, $>10^{13} M^{-1}$, etc.). In certain such embodiments, an antibody is capable of binding different antigens so long as the different antigens comprise that particular epitope. In certain instances, for example, homologous proteins from different species may comprise the same epitope.

As used herein, the term "anti-β-catenin antibody" or "β-catenin antibody" refers to an antibody which specifically recognizes an antigen and/or epitope presented by β-catenin. Antibodies that recognize epitopes on other molecular entities may be referred to according to a similar scheme (e.g., anti-CTLA-4, anti-PD-L1, etc.).

As used herein, the term "monoclonal antibody" refers to an antibody which is a member of a substantially homogeneous population of antibodies that specifically bind to the same epitope. In certain embodiments, a monoclonal antibody is secreted by a hybridoma. In certain such embodiments, a hybridoma is produced according to certain methods known to those skilled in the art. See, e.g., Kohler and Milstein (1975) Nature 256: 495-499; herein incorporated by reference in its entirety. In certain embodiments, a monoclonal antibody is produced using recombinant DNA methods (see, e.g., U.S. Pat. No. 4,816,567). In certain embodiments, a monoclonal antibody refers to an antibody fragment isolated from a phage display library. See, e.g., Clackson et al. (1991) Nature 352: 624-628; and Marks et al. (1991) J. Mol. Biol. 222: 581-597; herein incorporated by reference in their entireties. The modifying word "monoclonal" indicates properties of antibodies obtained from a substantially-homogeneous population of antibodies, and does not limit a method of producing antibodies to a specific method. For various other monoclonal antibody production techniques, see, e.g., Harlow and Lane (1988) Antibodies: A Laboratory Manual (Cold Spring Harbor Laboratory, Cold Spring Harbor, N.Y.); herein incorporated by reference in its entirety.

As used herein, the term "antibody fragment" refers to a portion of a full-length antibody, including at least a portion antigen binding region or a variable region. Antibody fragments include, but are not limited to, Fab, Fab', F(ab')$_2$, Fv, scFv, Fd, diabodies, and other antibody fragments that retain at least a portion of the variable region of an intact antibody. See, e.g., Hudson et al. (2003) Nat. Med. 9:129-134; herein incorporated by reference in its entirety. In certain embodiments, antibody fragments are produced by enzymatic or chemical cleavage of intact antibodies (e.g., papain digestion and pepsin digestion of antibody) produced by recombinant DNA techniques, or chemical polypeptide synthesis.

For example, a "Fab" fragment comprises one light chain and the $C_{H1}$ and variable region of one heavy chain. The heavy chain of a Fab molecule cannot form a disulfide bond with another heavy chain molecule. A "Fab'" fragment comprises one light chain and one heavy chain that comprises additional constant region, extending between the $C_{H1}$ and $C_{H2}$ domains. An interchain disulfide bond can be formed between two heavy chains of a Fab' fragment to form a "F(ab')$_2$" molecule.

An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203; herein incorporated by reference in their entireties. In certain instances, a single variable region (e.g., a heavy chain variable region or a light chain variable region) may have the ability to recognize and bind antigen.

Other antibody fragments will be understood by skilled artisans.

As used herein, the term "chimeric antibody" refers to an antibody made up of components from at least two different sources. In certain embodiments, a chimeric antibody comprises a portion of an antibody derived from a first species fused to another molecule, e.g., a portion of an antibody derived from a second species. In certain such embodiments, a chimeric antibody comprises a portion of an antibody derived from a non-human animal fused to a portion of an antibody derived from a human. In certain such embodiments, a chimeric antibody comprises all or a portion of a variable region of an antibody derived from a non-human animal fused to a constant region of an antibody derived from a human.

A "humanized" antibody refers to a non-human antibody that has been modified so that it more closely matches (in amino acid sequence) a human antibody. A humanized antibody is thus a type of chimeric antibody. In certain embodiments, amino acid residues outside of the antigen binding residues of the variable region of the non-human antibody are modified. In certain embodiments, a humanized antibody is constructed by replacing all or a portion of a complementarity determining region (CDR) of a human antibody with all or a portion of a CDR from another antibody, such as a non-human antibody, having the desired antigen binding specificity. In certain embodiments, a humanized antibody comprises variable regions in which all or substantially all of the CDRs correspond to CDRs of a non-human antibody and all or substantially all of the framework regions (FRs) correspond to FRs of a human antibody. In certain such embodiments, a humanized antibody further comprises a constant region (Fc) of a human antibody.

The term "human antibody" refers to a monoclonal antibody that contains human antibody sequences and does not contain antibody sequences from a non-human animal. In certain embodiments, a human antibody may contain synthetic sequences not found in native antibodies. The term is not limited by the manner in which the antibodies are made. For example, in various embodiments, a human antibody may be made in a transgenic mouse, by phage display, by human B-lymphocytes, or by recombinant methods.

As used herein, the term "natural antibody" refers to an antibody in which the heavy and light chains of the antibody have been made and paired by the immune system of a multicellular organism. For example, the antibodies produced by the antibody-producing cells isolated from a first animal immunized with an antigen are natural antibodies. Natural antibodies contain naturally-paired heavy and light chains. The term "natural human antibody" refers to an antibody in which the heavy and light chains of the antibody have been made and paired by the immune system of a human subject.

Native human light chains are typically classified as kappa and lambda light chains. Native human heavy chains are typically classified as mu, delta, gamma, alpha, or epsilon, and define the antibody's isotype as IgM, IgD, IgG, IgA, and IgE, respectively. IgG has subclasses, including, but not limited to, IgG1, IgG2, IgG3, and IgG4. IgM has subclasses including, but not limited to, IgM1 and IgM2. IgA has subclasses including, but not limited to, IgA1 and IgA2. Within native human light and heavy chains, the variable and constant regions are typically joined by a "J" region of about 12 or more amino acids, with the heavy chain also including a "D" region of about 10 more amino acids. See, e.g., Fundamental Immunology (1989) Ch. 7 (Paul, W., ed., 2nd ed. Raven Press, N.Y.); herein incorporated by reference in its entirety.

The term "neutralizing antibody" or "antibody that neutralizes" refers to an antibody that reduces at least one activity of a polypeptide comprising the epitope to which the antibody specifically binds. In certain embodiments, a neutralizing antibody reduces an activity in vitro and/or In vivo. In some embodiments, by neutralizing the polypeptide comprising the epitope, the neutralizing antibody inhibits the capacity of the cell displaying the epitope. For example, a "β-catenin neutralizing antibody" may reduce the capacity of β-catenin to act as a signal transducer.

As used herein, the term "glycoengineered", as used herein, includes any manipulation of the glycosylation pattern of a naturally occurring or recombinant protein, polypeptide or a fragment thereof.

The term "antigen-binding site" refers to a portion of an antibody capable of specifically binding an antigen. In certain embodiments, an antigen-binding site is provided by one or more antibody variable regions.

The term "epitope" refers to any polypeptide determinant capable of specifically binding to an immunoglobulin or a T-cell or B-cell receptor. In certain embodiments, an epitope is a region of an antigen that is specifically bound by an antibody. In certain embodiments, an epitope may include chemically active surface groupings of molecules such as amino acids, sugar side chains, phosphoryl, or sulfonyl groups. In certain embodiments, an epitope may have specific three dimensional structural characteristics (e.g., a "conformational" epitope) and/or specific charge characteristics.

An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

A "conservative" amino acid substitution refers to the substitution of an amino acid in a polypeptide with another amino acid having similar properties, such as size or charge. In certain embodiments, a polypeptide comprising a conservative amino acid substitution maintains at least one activity of the unsubstituted polypeptide. A conservative amino acid substitution may encompass non-naturally occurring amino acid residues, which are typically incorporated by chemical peptide synthesis rather than by synthesis in biological systems. These include, but are not limited to, peptidomimetics and other reversed or inverted forms of amino acid moieties. Naturally occurring residues may be divided into classes based on common side chain properties, for example: hydrophobic: norleucine, Met, Ala, Val, Leu, and Ile; neutral hydrophilic: Cys, Ser, Thr, Asn, and Gln; acidic: Asp and Glu; basic: His, Lys, and Arg; residues that influence chain orientation: Gly and Pro; and aromatic: Trp, Tyr, and Phe. Non-conservative substitutions may involve the exchange of a member of one of these classes for a member from another class; whereas conservative substitutions may involve the exchange of a member of one of these classes for another member of that same class.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families (see above). The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

The term "effective dose" or "effective amount" refers to an amount of an agent, e.g., an antibody, that results in the reduction of symptoms in a patient or results in a desired biological outcome. In certain embodiments, an effective dose or effective amount is sufficient to treat or reduce symptoms of a disease or condition.

As used herein, the terms "administration" and "administering" refer to the act of giving a drug, prodrug, or other agent, or therapeutic to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

The term "treatment" encompasses both therapeutic and prophylactic/preventative measures unless otherwise indicated. Those in need of treatment include, but are not limited to, individuals already having a particular condition as well as individuals who are at risk of acquiring a particular condition or disorder (e.g., those having a genetic or epigenetic predisposition; based on age, gender, lifestyle, etc.). The term "treating" refers to administering an agent to a subject for therapeutic and/or prophylactic/preventative purposes.

A "therapeutic agent" refers to an agent that may be administered In vivo to bring about a therapeutic and/or prophylactic/preventative effect.

A "therapeutic antibody" refers to an antibody that may be administered In vivo to bring about a therapeutic and/or prophylactic/preventative effect.

As used herein, the terms "co-administration" and "co-administering" refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term pharmaceutical composition" refers to the combination of an active agent (e.g., binding agent) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

As used herein, a "diagnostic" or "diagnostic test" includes the detection, identification, or characterization of a disease state or condition of a subject. For example, a disease or condition may be characterized to determine the likelihood that a subject with a disease or condition will respond to a particular therapy, determine the prognosis of a subject with a disease or condition (or its likely progression or regression), determine the effect of a treatment on a subject with a disease or condition, or determine a future treatment course of action.

DETAILED DESCRIPTION

Provided herein are compositions and methods for the treatment of cancer by inhibition of β-catenin or a β-catenin pathway. In particular, inhibitors of β-catenin and/or the Wnt/β-catenin signaling pathway are employed to prevent or reverse evasion of immune response or immunotherapy by cancers.

Immune evasion is a strategy used by pathogenic organisms and cancer cells (e.g., tumors) to evade a subject's immune response to maximize their probability of replication or to continue growth. Some cancers, for example solid tumor cancers, evade immune response using molecular mechanisms that result in exclusion of the host's immune response from the tumor microenvironment. The mechanisms that mediate exclusion of a host T cell response from the tumor microenvironment in the majority of cancer patients are not known. Using an autochthonous mouse melanoma model, experiments conducted during development of embodiments described herein demonstrate a causal effect between tumor-intrinsic active β-catenin signaling and T cell exclusion. Mechanistic studies revealed a lack of T cell priming against tumor-associated antigens in the context of β-catenin-expressing tumors. Activated β-catenin signaling resulted in transcriptional repression of the chemokine CCL4, which contributed to defective recruitment of CD103+ dermal dendritic cells, a subset necessary for activation of CD8+ T cells. Experiments conducted during development of embodiments described herein demonstrate that tumors expressing active β-catenin are resistant to therapy with anti-CTLA-4/anti-PD-L1 antibodies. Experiments further demonstrate that tumor cell-intrinsic β-catenin signaling prevents effector T cell-dependent immune surveillance of tumor cells. Thus, an oncogenic pathway has been identified that causes immune evasion in cancer (e.g., solid tumor cancer (e.g., melanoma, etc.), etc.). Experiments indicate that, in some embodiments, administration of immunotherapies of T cells, without also reducing the B-catenin signaling, is ineffective in treating tumors.

Experiments conducted during development of embodiments herein used a murine model systems to interrogate whether tumor cell-intrinsic β-catenin signaling pathway facilitates T cell exclusion against, for example, a pre-existing, antigen-specific immunity, and whether this results in the inhibition of immune surveillance process, resulting in more immunogenic but non-T cell-inflamed tumors. Indeed, results demonstrate that activation of tumor cell-intrinsic β-catenin facilitates T cell exclusion even against a strong pre-existing immunity. This effect is caused by a lack of effector T cell recruitment into the tumor which is generated by CD103+ DC in T cell inflamed tumors. Intra-vital imaging technology demonstrates that effector T cells in T cell-inflamed tumor engage in close contact with tumor cell in order to mediate tumor eradication and selection, a process that was not observed in β-catenin-positive tumors.

Experiments conducted during development of embodiments herein demonstrate that tumor cell-intrinsic signaling, such as the activation of the Wnt/β-catenin pathway, mediates resistance to immune surveillance and thereby displays an extremely potent mechanism of immune escape. Further, data indicates that even in the presence of activated, antigen-specific T cells, tumor cell-intrinsic β-catenin signaling inhibits infiltration of such T cells. In addition, it was demonstrated that in β-catenin-negative tumors, T cells engage in close interaction with tumor cells, which is associated with tumor eradication and was not observed in mice with β-catenin positive tumors. Mechanistically, DC-dependent mechanisms of effector T cell immune exclusion mediated by activation of tumor cell-intrinsic β-catenin signaling were identified.

Experiments conducted during development of embodiments herein demonstrate that tumor infiltration is associated with expression of CXCR3 on infiltrated T cells. The expression of CXCR3 ligands, CXCL9 and CXCL10, is highly correlated with inflammation in numerous tissues, even in normally immune privileged regions, including the brain. Experiments conducted during development of embodiments herein using cell sorting technology determined that the predominant source of CXCR3-ligands in the T cell-inflamed tumor model was derived from CD103+ tumor residing DC. This observation indicates that in the tumor context, chemokine-producing DCs contribute not only to T cell recruitment but also to the maintenance of their functional capacities.

Experiments conducted during development of embodiments herein have identified CD103+ DC as the cellular source of effector T cell recruiting chemokines within the tumor microenvironment of melanoma. The recruitment of those DC is highly dependent on the signaling profile of the tumor cells themselves since β-catenin positive tumor lack this subset of DC. Exploiting this observation, experiments demonstrated that lack of effector T cell recruitment prevents a potent anti-tumor immune response as well as tumor immune surveillance from occurring. The lack of effector T cell recruitment also prevented a therapeutic effect of adoptive T cell transfer, indicating that patients with a non-T cell inflamed phenotype might not benefit from cellular therapies.

In some embodiments, cancer treatment methods described herein comprise administration (or co-administration with one or more additional therapies/therapeutics) of one or more β-catenin or β-catenin pathway inhibitors. In some embodiments, a β-catenin or β-catenin pathway inhibitor is administered to render cancer cells, tumor(s), and/or the tumor microenvironment accessible or susceptible to treatment with the additional therapies/therapeutics (e.g., immunotherapeutics). β-catenin and β-catenin pathway inhibitors that find use in embodiments described herein are not limited by their mechanism of action. Any molecular or macromolecular entities or agents that target β-catenin or components of a β-catenin pathway and reduce or eliminate tumor immunity evasion may find use in embodiments described herein. Inhibitors may be small molecules, peptide, polypeptides, proteins, nucleic acids (e.g., antisense, RNAi, etc.), antibodies, antibody fragments, etc. In some embodiments, β-catenin inhibitors result in clearance of β-catenin (e.g., from the local environment (e.g., tumor microenvironment)) or prevent β-catenin signaling.

In some embodiments, a β-catenin inhibitor may disrupt the interaction of β-catenin with transcription factor 4

(TCF4). Suitable compounds for eliciting such disruption include, but are not limited to ZTM000990, PKF118-310, PKF118-744, PKF115-584, PKF222-815, CGP049090; and are described in Lepourcelet et al. Cancer Cell: January 2004 vol. 5, 91-102; herein incorporated by reference in its entirety.

In some embodiments, antibodies targeting β-catenin pathway molecules, or fragments thereof, are provided. In some embodiments, such antibodies or antibody fragments inhibit β-catenin signaling and/or cause clearance of β-catenin from the tumor microenviroment. Such antibodies may be naked, deriving their effect by the binding to β-catenin, or may be conjugated to a functional moiety (e.g., drug, toxin, effector moiety, etc.) from which the inhibitory capacity is derived. In some embodiments, a β-catenin pathway antibody is a neutralizing antibody, a monoclonal antibody, a humanized antibody, and/or an antibody fragment.

In certain embodiments described herein as encompassing a β-catenin inhibitor, an agent is provided that acts on an upstream or downstream component or target of a β-catenin signaling pathway (e.g., Wnt/β-catenin signaling pathway). In such embodiments, β-catenin is inhibited indirectly by targeting an upstream or downstream component or target. In some embodiments, by targeting a component upstream or downstream of β-catenin, the effect of the inhibition and any potential side effects may be balanced.

In some embodiments, provided herein are agents that inhibit the action/signaling of β-catenin, inhibit a β-catenin pathway, inhibit the Wnt/β-catenin pathway, etc. Suitable inhibitors include, but are not limited to small molecules, peptides, antibodies, nucleic acids, etc. Inhibitors may act by inhibiting the activity of β-catenin or another member of a β-catenin pathway, or may inhibit the expression thereof. Exemplary inhibitors include, but are not limited to: nucleic acids (See, e.g., U.S. Pat. No. 8,815,825; incorporated by reference in its entirety); an alpha-helix mimetic β-catenin inhibitor compound (See, e.g., WO 2014/061828; incorporated by reference in its entirety); the small molecule compounds described in U.S. Pub. No. 2014/0288174 (incorporated by reference in its entirety); a benzamide derivative (See, e.g., U.S. Pub. No. 2013/0039998; incorporated by reference in its entirety); curcumin or a derivative thereof (See, e.g., CN 201210490539; incorporated by reference in its entirety); and/or an inhibitor of a Wnt/β-catenin pathway that targets (e.g., directly or indirectly) a Wnt ligand, Frizzled protein (FZD), low density lipoprotein receptor-related protein 5 (LRP5) or LRP6, Dishevelled protein (Dvl), axin, adenomatous polyposis coli (APC) tumor suppressor protein, glycogen synthase kinase 3β (GSK3), casein kinase 1 (CK1), protein phosphatase 2A (PP2A), tankyrase 1, tankyrase 2, porcupine, β-catenin, a member of the DNA-binding T cell factor/lymphoid enhancer factor (TCF/LEF) family protein, a β-catenin C-terminal co-activator, or a β-catenin N-terminal co-activator.

Many embodiments herein are described with reference to a β-catenin inhibitor. It is within the scope herein to utilize Wnt/β-catenin pathway or signaling inhibitor in place of a β-catenin inhibitor in certain embodiments herein. For example, in place of a β-catenin inhibitor, an agent that inhibit binding or Wnt ligands to their receptors may be employed.

In some embodiments, a subject is treated with one or more β-catenin inhibitors as well as one or more additional cancer therapies. Such therapies include chemotherapy, immunotherapy, radiation, surgery, etc. In some embodiments, β-catenin inhibitors are co-administered with one or more additional agents for the treatment of cancer.

In some embodiments, exemplary anticancer agents suitable for use in compositions and methods described herein (e.g., co-administered with a β-catenin inhibitor) include, but are not limited to: 1) alkaloids, including microtubule inhibitors (e.g., vincristine, vinblastine, and vindesine, etc.), microtubule stabilizers (e.g., paclitaxel (Taxol), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies (e.g., conjugated with anticancer drugs, toxins, and/or radionuclides, etc.; neutralizing antibodies; etc.); 9) biological response modifiers (e.g., interferons (e.g., IFN-.alpha., etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); and 22) modulators of p53 protein function.

In some embodiments, one or more β-catenin inhibitors or Wnt/β-catenin signaling inhibitors are administered to overcome immune invasion of the cancer cells, tumor, tumor microenvironment, etc. In some embodiments, one or more additional cancer immunotherapies are employed (e.g., concurrently or serially) to make use of the immune-responsiveness of the β-catenin-inhibitor-treated cells/tumor. Suitable immunotherapies may include, but are not limited to: cell-based therapies (e.g., dendritic cell or T cell therapy, etc.), monoclonal antibody (mAb) therapy (e.g., naked mAbs, conjugated mAbs), cytokine therapy (e.g., interferons, interleukins, etc.), adjuvant treatment (e.g., polysaccharide-K), etc.

In some embodiments, β-catenin inhibitors or Wnt/β-catenin signaling inhibitors are co-administered with agents (e.g., small molecules, peptides, antibodies, antibody fragments, etc.) that target one or more cancer cell or tumor) markers or components. In some embodiments, co-administration of the β-catenin pathway inhibitor renders the cancer cells, tumor, and/or tumor microenvironment susceptible and/or accessible to the treatment with the additional agent.

In some embodiments, agents for use in the methods and compositions described herein target and/or binds a cancer or tumor cell marker or component, selected from the group including but not limited to, epidermal growth factor receptor (EGFR, EGFR1, ErbB-1, HER1). ErbB-2 (HER2/neu), ErbB-3/HER3, ErbB-4/HER4, EGFR ligand family; insulin-like growth factor receptor (IGFR) family, IGF-binding proteins (IGFBPs), IGFR ligand family (IGF-1R); platelet derived growth factor receptor (PDGFR) family, PDGFR ligand family; fibroblast growth factor receptor (FGFR) family, FGFR ligand family, vascular endothelial growth factor receptor (VEGFR) family, VEGF family; HGF receptor family: TRK receptor family; ephrin (EPH) receptor family: AXL receptor family; leukocyte tyrosine kinase (LTK) receptor family; TIE receptor family, angiopoietin 1, 2; receptor tyrosine kinase-like orphan receptor (ROR) receptor family; discoidin domain receptor (DDR) family; RET receptor family; KLG receptor family; RYK receptor family; MuSK receptor family; Transforming growth factor alpha (TGF-α), TGF-α receptor; Transforming growth factor-beta (TGF-β), TGF-β receptor; Interleukin β receptor alpha2 chain (IL13Ralpha2), Interleukin-6 (IL-6), IL-6 receptor, interleukin-4, IL-4 receptor, Cytokine receptors, Class I (hematopoietin family) and Class II (interferon/IL-10 family) receptors, tumor necrosis factor (TNF) family, TNF-α, tumor necrosis factor (TNF) receptor superfamily (TNTRSF), death receptor family, TRAIL-receptor; cancer-testis (CT) antigens, lineage-specific antigens, differentiation antigens, alpha-actinin-4, ARTC1, breakpoint cluster region-Abelson (Bcr-abl) fusion products, B-RAF, caspase-5 (CASP-5), caspase-8 (CASP-8), beta-catenin (CTNNB1), cell division cycle 27 (CDC27), cyclin-dependent kinase 4 (CDK4), CDKN2A, COA-1, dek-can fusion protein, EFTUD-2, Elongation factor 2 (ELF2), Ets variant gene 6/acute myeloid leukemia 1 gene ETS (ETC6-AML1) fusion protein, fibronectin (FN), GPNMB, low density lipid receptor/GDP-L fucose: beta-Dgalactose 2-alpha-Lfucosyltraosferase (LDLR/FUT) fusion protein, HLA-A2, MLA-A11, heat shock protein 70-2 mutated (HSP70-2M), KIAA0205, MART2, melanoma ubiquitous mutated 1, 2, 3 (MUM-1, 2, 3), prostatic acid phosphatase (PAP), neo-PAP, Myosin class 1, NFYC, OGT, OS-9, pml-RARalpha fusion protein, PRDX5, PTPRK, K-ras (KRAS2), N-ras (NRAS), HRAS, RBAF600, SIRT12, SNRPD1, SYT-SSX1 or -SSX2 fusion protein, Triosephosphate Isomerase, BAGE, BAGE-1, BAGE-2, 3, 4, 5, GAGE-1, 2, 3, 4, 5, 6, 7, 8, GnT-V (aberrant N-acetyl glucosaminyl transferase V, MGATS), HERV-K MEL, KK-LC, LAGE, LAGE-1, CTL-recognized antigen on melanoma (CAMEL), MAGE-A1 (MAGE-1). MAGE-A2, MAGE-A3, MAGE-A4, MAGE-AS, MAGE-A6, MAGE-A8, MAGE-A9, MAGE-A10. MAGE-A11, MAGE-A12, MAGE-3, MAGE-B1, MAGE-B2, MAGE-B5. MAGE-B6, MAGE-C1, MAGE-C2, mucin 1 (MUC1), MART-1/Melan-A (MLANA), gp100, gp100/Pme117 (S1LV), tyrosinase (TYR), TRP-1, HAGE, NA-88, NY-ESO-1, NY-ESO-1/LAGE-2, SAGE, Sp17. SSX-1, 2, 3, 4, TRP2-1NT2, carcino-embryonic antigen (CEA), Kallikrein 4, mammaglobin-A, OA1 prostate specific antigen (PSA), prostate specific membrane antigen, TRP-1/, 75. TRP-2 adipophilin, interferon inducible protein absent in melanoma 2 (AIM-2). BING-4, CPSF, cyclin D1, epithelial cell adhesion molecule (Ep-CAM), EpbA3, fibroblast growth factor-5 (FGF-5), glycoprotein 250 (gp250intestinal carboxyl esterase (iCE), alpha-feto protein (AFP), M-CSF, mdm-2, MUCI, p53 (TP53), PBF, PRAME, PSMA, RAGE-1, RNF43, RU2AS, SOX10, STEAP1, survivin (BIRCS), human telomerase reverse transcriptase (hTERT), telomerase, Wilms' tumor gene (WT1), SYCP1, BRDT, SPANX, XAGE, ADAM2, PAGE-5, LIP1, CTAGE-1, CSAGE, MMA1, CAGE, BORIS, HOM-TES-85, AF15q14, HCA66I, LDHC, MORC, SGY-1, SPO11, TPX1, NY-SAR-35, FTHLI7, NXF2 TDRD1, TEX 15, FATE, TPTE, immunoglobulin idiotypes, Bence-Jones protein, estrogen receptors (ER), androgen receptors (AR), CD40, CD30, CD20, CD19, CD33, CD4, CD25, CD3, cancer antigen 72-4 (CA 72-4), cancer antigen 15-3 (CA 15-3), cancer antigen 27-29 (CA 27-29), cancer antigen 125 (CA 125), cancer antigen 19-9 (CA 19-9), beta-human chorionic gonadotropin, 1-2 microglobulin, squamous cell carcinoma antigen, neuron-specific enolase, heat shock protein gp96. GM2, sargramostim, CTLA-4, 707 alanine proline (707-AP), adenocarcinoma antigen recognized by T cells 4 (ART-4), carcinoembryogenic antigen peptide-1 (CAP-1), calcium-activated chloride channel-2 (CLCA2), cyclophilin B (Cyp-B), human signet ring tumor-2 (HST-2), etc.

Examples of antibodies which can be incorporated into compositions and methods disclosed herein include, but are not limited, to antibodies such as trastuzumab (anti-HER2/neu antibody); Pertuzumab (anti-HER2 mAb); cetuximab (chimeric monoclonal antibody to epidermal growth factor receptor EGFR); panitumumab (anti-EGFR antibody); nimotuzumab (anti-EGFR antibody); Zalutumumab (anti-EGFR mAb); Necitumumab (anti-EGFR mAb); MDX-210 (humanized anti-HER-2 bispecific antibody); MDX-210 (humanized anti-HER-2 bispecific antibody); MDX-447 (humanized anti-EGF receptor bispecific antibody); Rituximab (chimeric murine/human anti-CD20 mAb); Obinutuzumab (anti-CD20 mAb); Ofatumumab (anti-CD20 mAb); Tositumumab-1131 (anti-CD20 mAb); Ibritumomab tiuxetan (anti-CD20 mAb); Bevacizumab (anti-VEGF mAb); Ramucirumab (anti-VEGFR2 mAb); Ranibizumab (anti-VEGF mAb); Aflibercept (extracellular domains of VEGFR1 and VEGFR2 fused to IgG1 Fc); AMG386 (angiopoietin-1 and -2 binding peptide fused to IgG1 Fc); Dalotuzumab (anti-IGF-1R mAb); Gemtuzumab ozogamicin (anti-CD33 mAb); Alemtuzumab (anti-Campath-1/CD52 mAb); Brentuximab vedotin (anti-CD30 mAb): Catumaxomab (bispecific mAb that targets epithelial cell adhesion molecule and CD3); Naptumomab (anti-5T4 mAb); Girentuximab (anti-Carbonic anhydrase ix); or Farletuzumab (anti-folate receptor). Other examples include antibodies such as Panorex™ (17-1A) (murine monoclonal antibody); Panorex (@(17-1A)) (chimeric murine monoclonal antibody); BEC2 (ami-idiotypic mAb, mimics the GD epitope) (with BCG); Oncolym (Lym-1 monoclonal antibody); SMART M195 Ab, humanized 13' LYM-1 (Oncolym). Ovarex (B43.13, anti-idiotypic mouse mAb); 3622W94 mAb that binds to EGP40 (17-1A) pancarcinoma antigen on adenocarcinomas; Zenapax (SMART Anti-Tac (IL-2 receptor); SMART M195 Ab, humanized Ab, humanized); NovoMAb-G2 (pancarcinoma specific Ab); TNT (chimeric mAb to histone antigens); TNT (chimeric mAb to histone antigens); Gliomab-H (Monoclonals—Humanized Abs); GNI-250 Mab; EMD-72000 (chimeric-EGF antagonist); LymphoCide (humanized IL.L.2 antibody); and MDX-260 bispecific, targets GD-2, ANA Ab, SMART IDIO Ab, SMART ABL 364 Ab, or ImmuRAIT-CEA.

In some embodiments, the agent specifically binds a component of a regulatory T cell, myeloid suppressor cell, or dendritic cell. In another aspect, the targeting moiety specifically binds one of the following molecules: CD4; CD25 (IL-2α receptor; IL-2αR); cytotoxic T-lymphocyte antigen-4 (CTLA-4; CD152); Interleukin-10 (IL-10); Transforming growth factor-beta receptor (TGF-βR); Transforming growth factor-beta (TGF-β); Programmed Death-1 (PD-1); Programmed death-1 ligand (PD-L1 or PD-L2); Receptor activator of nuclear factor-κB (RANK); Receptor activator of nuclear factor-κB (RANK) ligand (RANKL); LAG-3; glucocorticoid-induced tumor necrosis factor receptor family-related gene (GITR; TNFRSF18); or Interleukin-4 receptor (IL-4R). In some embodiments, the agent is an agonist that increases the function of the targeted molecule. In other embodiments, the agent is an antagonist that inhibits the function of the targeted molecule.

In some embodiments, an agent binds a specific cytokine, cytokine receptor, co-stimulatory molecule, co-inhibitory molecule, or immunomodulatory receptor that modulates the immune system. In another aspect, the targeting moiety specifically binds one of the following molecules: tumor necrosis factor (TNF) superfamily; tumor necrosis factor-α (TNF-α); tumor necrosis factor receptor (TNFR) superfamily; Interleukin-12 (IL-12); IL-12 receptor; 4-1BB (CD137); 4-1BB ligand (4-1BBL; CD137L); OX40 (CD134; TNR4); OX40 ligand (OX40L; CD40; CD40 ligand (CD40L); CTLA-4; Programmed death-1 (PD-1); PD-1 ligand I (PD-L1: B7-H1); or PD-1 ligand 2 (PD-L2; B7-DC); B7 family; B7-1 (CD80); B7-2 (CD86); B7-H3; B7-H4; GITR/AITR: GITRL/AITRL; BTLA; CD70; CD27; LIGHT; HVEM: Toll-like receptor (TLR) (TLR 1, 2, 3, 4, 5, 6, 7, 8, 9, 10). In some embodiments, the agent is an agonist that increases the function of the targeted molecule. In other embodiments, the agent is an antagonist that inhibits the function of the targeted molecule.

In some embodiments, β-catenin inhibitors and/or additional agents (e.g., immunotherapeutics) are co-administered (e.g., serially or sequentially) with one or more adjuvants. Suitable adjuvants include, but are not limited to, one or more of: oil emulsions (e.g., Freund's adjuvant); saponin formulations; virosomes and viral-like particles; bacterial and microbial derivatives; immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

Adjuvants may also include immunomodulators such as cytokines, interleukins (e.g., IL-1, IL-2, IL-4, IL-5, IL-6, IL-7, IL-12, etc.), interferons (e.g., interferon-.gamma.), macrophage colony stimulating factor, and tumor necrosis factor. In addition to variant B7-DC polypeptides, other co-stimulatory molecules, including other polypeptides of the B7 family, may be administered. Proteinaceous adjuvants may be provided as the full-length polypeptide or an active fragment thereof, or in the form of DNA, such as plasmid DNA.

Pharmaceutical and immunotherapeutic compositions described herein may be delivered by any suitable route of administration (e.g., oral delivery, parenteral delivery, mucous membrane delivery, pulmonary delivery, intravenous delivery, etc.). Appropriate formulations for such delivery routes are understood in the field.

Non-limiting examples of cancers that may be treated with the compositions and methods described herein include, but are not limited to: melanoma (e.g., metastatic malignant melanoma), renal cancer (e.g. clear cell carcinoma), prostate cancer (e.g. hormone refractory prostate adenocarcinoma), pancreatic cancer (e.g., adenocarcinoma), breast cancer, colon cancer, lung cancer (e.g. non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies. In some embodiments, the cancer is a solid tumor cancer.

Some embodiments described herein are particularly useful for the treatment of tumors that do not otherwise respond to immunotherapeutic approaches. In some embodiments, provided herein is the treatment of cancers exhibiting tumor-intrinsic-β-catenin-signaling. In some embodiments, such tumors are non-responsive (or have a reduced response) to T cells (e.g., prevent infiltration of one or more T cell types (e.g., CD8$^+$ T cells) or antigen presenting cells (e.g., dendritic cells (e.g., CD103$^+$DCs, etc.), etc.). In some embodiments, compositions and methods described herein find use in the treatment of cancers in which T cells are not appropriately primed against tumor-associated antigens. In some embodiments, compositions and methods described herein find use in the treatment of cancers comprising tumors or cells that are defective in recruitment of dendritic cells (e.g., CD103$^+$ DCs, etc.). In some embodiments, compositions and methods described herein find use in the treatment of cancers comprising tumors or cells that are defective in production of the chemokine CCL4.

In some embodiments, methods are provided for testing sample (e.g., cell, tissue, population of cells, tumor, blood, urine, saliva, etc.) from a subject for one or more biomarkers (e.g., biomarkers of: β-catenin activation, tumor-intrinsic-β-catenin-signaling, Wnt/β-catenin signaling, exclusion of T cell infiltration, transcriptional repression of chemokine CCL4, defective recruitment of CD103$^+$ dermal dendritic cells, and/or activation of CD8$^+$ T cells). Such biomarkers may comprise nucleic acids, small molecules, proteins, peptides, etc., and may be detected using any suitable assay of technique. In some embodiments, provided herein are DNA-, RNA-, small molecule, and/or protein-based diagnostic methods that either directly or indirectly detect the biomarkers of the evasion of immune response or immunotherapy by cancer cells or tumors. The present invention also provides compositions, reagents, and kits for such diagnostic purposes.

In some embodiments, biomarkers are detected at the nucleic acid (e.g., RNA) level. For example, the presence or amount of biomarker nucleic acid (e.g., mRNA) in a sample is determined (e.g., to determine the presence or level of biomarker expression). Biomarker nucleic acid (e.g., RNA, amplified cDNA, etc.) may be detected/quantified using a variety of nucleic acid techniques known to those of ordinary skill in the art, including but not limited to nucleic acid sequencing, nucleic acid hybridization, nucleic acid amplification (e.g., by PCR, RT-PCR, qPCR, etc.), micorarray, Southern and Northern blotting, sequencing, etc. Non-amplified or amplified nucleic acids can be detected by any conventional means. For example, in some embodiments, nucleic acids are detected by hybridization with a detectably labeled probe and measurement of the resulting hybrids. Nucleic acid detection reagents may be labeled (e.g., fluorescently) or unlabeled, and may by free in solution or immobilized (e.g., on a bead, well, surface, chip, etc.).

In some embodiments, biomarkers are detected at the protein level. For example, the presence or amount of biomarker protein in a sample is determined (e.g., to determine the presence or level of biomarker expression or localization). In some embodiments, reagents are provided for the detection and/or quantification of biomarker proteins. Suitable reagents include primary antibodies (e.g., that bind to the biomarkers), secondary antibodies (e.g., that bind primary antibodies), antibody fragments, aptamers, etc. Protein detection reagents may be labeled (e.g., fluorescently) or unlabeled, and may by free in solution or immobilized (e.g., on a bead, well, surface, chip, etc.).

In some embodiments, biomarker capture reagents are provided to localize, concentrate, aggregate, etc. a biomarker. For example, in some embodiments a biomarker capture reagent that interacts with the biomarker is linked to a solid support (e.g., a bead, surface, resin, column, and the like) that allows manipulation by the user on a macroscopic scale. Often, the solid support allows the use of a mechanical means to isolate and purify the biomarker from a heterogeneous solution. For example, when linked to a bead, separation is achieved by removing the bead from the heterogeneous solution, e.g., by physical movement. In embodiments in which the bead is magnetic or paramagnetic, a magnetic field is used to achieve physical separation of the capture reagent (and thus the target) from the heterogeneous solution. Magnetic beads used to isolate targets are described in the art, e.g., as described in European Patent Application No. 87309308, incorporated herein in its entirety for all purposes.

Compositions for use in the diagnostic methods or testing steps described herein include, but are not limited to, probes, amplification oligonucleotides, and antibodies. Any of the detection and/or diagnostic reagents used in embodiments described herein may be provided alone or in combination with other compositions in the form of a kit. Kits may include any and all components necessary or sufficient for assays including, but not limited to, the detection reagents, buffers, control reagents (e.g., tissue samples, positive and negative control sample, etc.), solid supports, labels, written and/or pictorial instructions and product information, inhibitors, labeling and/or detection reagents, package environmental controls (e.g., ice, desiccants, etc.), and the like. In some embodiments, the kits provide a sub-set of the required components, wherein it is expected that the user will supply the remaining components. In some embodiments, the kits comprise two or more separate containers wherein each container houses a subset of the components to be delivered.

In some embodiments, a computer-based analysis program is used to translate the raw data generated by the detection assay (e.g., the presence, absence, or amount of expression a biomarker) into data of predictive value for a clinician (e.g., likelihood that a subject's cancer will evade immunotherapy). In some embodiments, computer analysis combines various data into a single score or value that is predictive and/or diagnostic. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject. Contemplated herein are any methods capable of receiving, processing, and transmitting the information to and from laboratories conducting the assays, information providers, medical personal, and subjects. For example, in some embodiments of the present invention, a sample (e.g., a biopsy, cell, or blood sample) is obtained from a subject and submitted to a profiling service (e.g., clinical lab at a medical facility, third-party testing service, genomic profiling business, etc. to generate raw data. Where the sample comprises a tissue or other biological sample, the subject may visit a medical center to have the sample obtained and sent to the profiling center, or subjects may collect the sample themselves and directly send it to a profiling center. In some embodiments, a report is generated (e.g., by a clinician, by a testing center, by a computer or other automated analysis system, etc.). A report may contain test results, diagnoses, and/or treatment recommendations (e.g., β-catenin inhibitor and immunotherapy co-administration, etc.).

EXPERIMENTAL

Example 1

Experimental Methods (Results in Example 2)

Analysis of TCGA Data Set Containing 266 Metastatic Skin Cutaneous Melanoma Patients Level 4 gene expression data and level 2 somatic mutation data were downloaded for skin cutaneous melanoma (SKCM) from TCGA, which were processed by Broad Institute's TCGA workgroup. The RNAseq level 4 gene expression data contains upper quartile normalized and log 2 transformed RSEM values summarized at gene level (Li & Dewey. *BMC bioinformatics* 12, 323 (2011).; herein incorporated by reference in its entirety). The whole exome sequencing (WXS) level 2 mutation data contains somatic mutation calls for each subject. A total of 266 metastatic SKCM samples were analyzed. For clustering of cold and hot tumors, genes expressed in less than 80% of the samples were removed. A total of 15,974 genes were kept for further analysis. Unsupervised hierarchical clustering of the genes was performed in primary tumors and metastasis samples separately using K-mean equal to 12 and Euclidean distance metrics. Clusters containing the thirteen known T cell signature transcripts (CD8A, CCL2, CCL3, CCL4, CXCL9, CXCL10, ICOS, GZMIC, IRF1, HLA-DMA, HLA-DMB, HLADOA, HLA-DOB) were selected for resampling-based hierarchical clustering of the samples using ConsensusClusterPlus v1.16.0 (Wilkerson & Hayes. Bioinformatics 26, 1572-1573 (2010); herein incorporated by reference in its entirety). This procedure was performed with 2,000 random selections of 80% of the samples and Euclidean distance metrics. Genes differentially expressed between cold and hot tumor groups were detected using ANOVA and filtered by false discovery rate (FDR) q-value <0.01 and fold change >2.0. Canonical pathways significantly enriched in the genes of interest were identified by Ingenuity Pathways Analysis (IPA) (Ingenuity® Systems) based on experimental evidence from the Ingenuity Knowledge Base. The somatic variants were converted to VCF format and annotated using ANNOVAR (Wang & Hakonarson. Nucleic acids research 38, e164 (2010); herein incorporated by reference in its entirety). Each variant was annotated with known genes, exonic functions, predicted amino acid changes, and minor allele frequencies derived from the 1000 Genomes Project and the NHLBI Exome Sequencing Project (ESP6500SI-V2-SSA137) (EVS) (Genomes Project, C. et al. Nature 491, 56-65 (2012); herein incorporated by reference in its entirety). Synonymous SNVs were excluded from further analysis. The variants were then summarized at gene level and patient level for comparison of mutation profiles between the cold and hot tumor groups. Interactions between proteins encoded by genes of interest were retrieved from STRING database based on high confidence evidence collected from co-expression data, experiments and databases (Jensen et al. Nucleic acids research 37, D412-416 (2009); herein incorporated by reference in its entirety). SNV located in selected genes were analyzed using the Variant Effect Prediction software in combination with Uniprot database. Calls of loss-of-function and gain-of-function were based on existing experimental data obtained from the Uniprot data base while harmful or tolerated effects on the protein structure were predicted using the SIFT prediction algorithm imbedded in the Variant Effect Predictions analysis. A continuous numerical score was generated using the six β-catenin target genes (EFNB3, APC2, TCF1, c-myc, TCF12, VEGFA) reads. The resulting score was used to align patients based on activity of the β-catenin pathway.

Mice, Tumor Induction and Generation of Tumor Cell Lines

The following mouse strains were used to generate the mouse models used in experiments conducted during development of embodiments described herein: Tyr:Cre-ER, loxP-Braf$^{V600E}$, loxP-PTEN, loxP-CAT-STA, loxP-rosa-SIY and loxP-rosa-YFP (strain 006148) reporter (Cheung et al. Cancer research 68, 9459-9468 (2008); Bosenberg et al. Genesis 44, 262-267 (2006); Dankort. et al. Genes & development 21, 379-384 (2007); Suzuki et al. Current biology: CB 8, 1169-1178 (1998); Gounari et al. Oncogene 21, 4099-4107 (2002); herein incorporated by reference in their entireties). As an initial cross, the Tyr:Cre-ER mice were crossed onto loxP-BrafV600E and subsequently crossed with the loxP-PTEN mouse strain. Those mice were maintained as Tyr:Cre-ER$^+$, loxP-Braf$^{V600E+/-}$, PTEN$^{fl/fl}$ and will be referred to as Braf$^{V600E}$/PTEN$^{-/-}$. Additionally Tyr:Cre-ER, loxP-Braf$^{V600E}$ mice were crossed to the loxP-CAT-STA mouse strain with subsequent crossing to the loxP-PTEN strain. Those mouse strains were maintained as Tyr:Cre-ER$^+$, loxP-Braf$^{V600E+/-}$loxP-CAT-STA$^{+/+}$ and Tyr:Cre-ER+, los P-Braf$^{V600E+/-}$, PTEN$^{fl/fl}$, loxP-CAT-STA$^{+/+}$ and will be referred to as Braf$^{V600E}$/CAT-STA or Braf$^{V600E}$/PTEN$^{-/-}$/CAT-STA, respectively. Additionally, the Braf$^{V600E}$/PTEN$^{-/-}$ and Braf$^{V600E}$/PTEN$^{-/-}$/CAT-STA were crossed to the loxP-rosa-SIY mouse and mice were maintained heterozygote for the rosa locus. Similarly, Braf$^{V600E}$/PTEN$^{-/-}$ were bred onto the loxP-rosa-YFP reporter strain which were also maintained with heterozygous breeders for this locus. Genotyping was performed as described earlier (Cheung et al. Cancer research 68, 9459-9468 (2008); Bosenberg et al. Genesis 44, 262-267 (2006); Dankort. et al. Genes & development 21, 379-384 (2007); Suzuki et al. Current biology: CB 8, 1169-1178 (1998); Gounari et al. Oncogene 21, 4099-4107 (2002); Jeong et al. Genes & development 18, 937-951 (2004); herein incorporated by reference in their entireties). For tumor induction, 6-10 week old mice were shaved on the back and 5 μl of 4-HO-Tamixifen (Sigma) at a concentration of 10 mg/ml (dissolved in acetone) were applied. Subsequently, mice were screened weekly for tumor induction and growth the with endpoint criteria of 4000 mm$^3$. For tumor cell line generation, a single cell suspension of the tumor tissue was generated as described below and used in its entirety for subcutaneous injections into Rag-KO mice (RAGN12-F; Taconic). Following tumor outgrowth, the tumor tissue was harvested and reinjected into Rag-KO mice, C57/BL6 mice (Taconic), and adapted to cell culture using DMEM (Gibco) with 10% FCS (Atlanta Biologics), 1×NEAA (Gibco) and 1×MOPS (Sigma). One cell line was derived from each genotype Braf$^{V600E}$/PTEN$^{-/-}$ and Braf$^{V600E}$/PTEN$^{-/-}$/CAT-STA, which are abbreviated with BP and BPC, respectively. Additionally, TCRTg 2C mice were maintained as T cell donors (Manning et al. Journal of immunology 159, 4665-4675 (1997); herein incorporated by reference in its entirety), actin:GFP mice were obtained from Jackson (strain ID 003291), Batf3$^{-/-}$ mice were maintained as bone marrow donors. All animal procedures were approved by the IACUC Committee of the University of Chicago. Human tumor cell lines were obtained from National Cancer Institute and maintained in RPMI medium supplemented with 10% FCS and 1×NEAA.

Tumor Growth, Tissue Harvest and Single Cell Suspensions

For tumor outgrowth experiments, mice were treated at the lower back with 4-OH-Tamoxifen at day 0. Following day 21, tumor masses were measured by assessing length, width and height of major tumor mass. Tumor volume was calculated: $T_v = T_L * T_W * T_H$. At the indicated experimental endpoint, tumor tissue was harvested, cleared from remaining skin and minced using razor blades. Subsequently, tumor pieces were digested using a human tumor digestion kit (Miltenyi) in combination with a tissue dissociater (Miltenyi). For flow cytometric analysis and cell sorting, living cells were separated using a Ficoll (GE) centrifugation step with subsequent washing of the obtained cells. For generation of tumor cell lines, the cell suspension was used directly after digestion and two washing steps.

Immunohistochemistry and Fluorescent Immunohistology

The immune-histology staining on human samples was performed by the Human Tissue Resource Center of the University of Chicago using biopsies from malignant melanoma patients. Staining was performed using a CD8-specific monoclonal antibody (CD8 (clone C8/144B, NeoMarkers), β-catenin (clone CAT-5H1, Life technologies) in combination with a secondary goat anti-mouse immunoglobulin G (IgG) conjugated to an alkaline phosphatase (Biocare Medical) was applied. Slides were scanned using a CRi Panoramic Scan Whole Slide Scanner. Positivity for β-catenin staining was obtained first and grading was based on the staining intensity. Subsequently, the number of CD8-positive T cells within one needle biopsy (2.5 mm diameter) was counted using ImageJ cell counter and calculated as #CD8/mm$^2$. Samples with less than 50 CD8+ T cells per mm$^2$ were considered T cell infiltrate low, while counts >50 per mm$^2$ were considered as T cell high, similar as described in$_{58}$. For mouse fluorescent immunohistology staining, formalin/paraffin-fixed tissues were used to obtain 5 μm sections for subsequent staining. Staining was performed using the following primary antibodies: anti-CD3 (clone SP7, 1:500, Abcam), anti-CD45R (clone RA3-6B2, 1:100, Abcam) and anti-Tyrpl (clone EPR13063, 1:500, Abcam) in combination with goat anti-rabbit 594 or goat anti-rat 488 (Jacksonlmmuno) and Hoechst counter stain. Slides were imaged using a Zeiss Axiovert 200 with a Hammatsu Orca ER firewire digital monochrome camera.

Flow Cytometry and Cell Sorting

For flow cytometric analysis, washed cells were resuspended in staining buffer (PBS with 10% FCS and 0.5 M EDTA (Ambion). Cells were incubated with live/dead staining dye (Invitrogen, wavelength 450) and Fc Block (clone 93; Biolegend) for 20 min on ice. Subsequently, specific antibodies were added and staining was continued for 40 min on ice. After a washing step, cells were either analyzed directly or fixed with 4% PFA (BD) solution for 30 min and stored in a 1 PFA solution until analysis. For staining of TCRTg 2C T cells a TCR specific-biotinylated mAb (1B2 clone) was obtained from the University of Chicago Monoclonal Core Facility. Subsequent to live/dead staining, TCR-specific mAb was added for 15 min on ice at a 1:100 dilution alone with surface Abs targeting other antigens added in for an additional 25 minutes thereafter. After a washing step, a 1:500 dilution of Streptavidin APC was added and incubated on ice for 20 minutes before cells were fixed in 4% PFA and stored in 1% PFA solution. Flow cytometry sample acquisition was performed on a LSR2B (BD), and analysis was performed using FlowJo software (TreeStar). For cell sorting, staining protocols were carried out similarly under sterile conditions. Cell sorting were performed using an ARIAIIIu (BD) and cells were collected in 100% FCS if further used for in vitro analysis or in TriZol Reagent (Invitrogen) if used for RNA isolation. Percent of T cells was calculated as followed [(100/amount of total living cells acquired)*amount $CD3^+$ T cells]; number/gram tumor was calculated as followed [number of acquired $CD3^+$ T cells/ tumor weight].

T Cell Stimulation $2.5\times10^4$ sorted T cells from spleen and/or tumor were either stimulated on plates coated with 1 μg/ml anti-CD3 antibody (145-2C11 clone; Biolegend) and 2 mg/ml anti-CD28 antibody (37.51 clone BD) in T cell medium (DMEM, 10% FCS, 1×NEAA, 1×MOPS, 500 μM β-mercapthoethanol (Sigma) or plated on tissue culture-treated uncoated plates for 8 h. Following incubation, cells were harvested and resuspended in TriZol Reagent (Invitrogen) for subsequent RNA isolation.

RNA Isolation and Quantitative Reverse Transcriptase-PCR

RNA isolation using TriZol was performed according to the manufacturer's instructions. In the case of RNA isolation from whole tumor tissue, a piece of tumor was snap frozen in TriZol at the time of tumor harvest. Before RNA isolation the tissue was thawed at room temperature and homogenization was achieved using a tissue homogenizer (GE) with homogenizer tips (USA scientific). Subsequent RNA isolation was performed according the manufacturer's instructions. Reverse transcriptase reaction was performed using High Capacity cDNA RTPCR Kit (Life Technologies) according to instructions and 1 μl was of the resulting copy-DNA was used for qPCR. qPCR reactions were carried out using Sybr Green or TaqMan master mix (Life technologies) and defined primer sets or primer/probe sets (probes were obtained from Roche), respectively. Reactions were run on a 7300 RT PCR system machine (Applied Biosystems) and expression level and fold change were calculated as following: $\Delta CT=CT_{gene\ of\ interest}-CT_{18S}$, expression level=$2^{-\Delta CT}$, fold change=$2^{-(\Delta CT_{reference\ sample}-\Delta CT_{tested\ sample})}$ (Schmittgen & Livak. Nature protocols 3, 1101-1108 (2008); herein incorporated by reference in its entirety).

Adoptive T Cell Transfer

For adoptive T cell transfer experiments, tumor development was induced and transfer of $1\times10^6$ T cells was performed when tumor reached near end point sizes (approx. 3-4 weeks after induction). Transferred T cells were isolated from gender-matched 2C donor mice using the Miltenyi $CD8^+$ enrichment Kit II for untouched $CD8^+$ T cell isolation. After isolation cells were stained with 1 μM CFSE-solution (eBioscience) for 8 min at 37° C. before intravenous injection. Tumor tissue, tumor-draining LNs, and spleen were harvested 5 days following adoptive transfer of T cells and used for flow cytometric analysis. For tumor tissues, the entirety of each sample was acquired and total number of $CD3^+CD8^+$ T cells and transferred 2C cells was assessed. The percentage 2C cells was calculated as [(100/$CD3^+$/$CD8^+$ T cells)*2C] and also the number of 2C cells per gram tumor.

Generation of Bone Marrow Chimeras

To condition host mice to generate bone marrow chimeras, indicated mouse strains were irradiated twice with a 3 h interval and a first irradiation does of 500 rad followed by 550 rad. 24 h after the second irradiation dose, bone marrow from gender-matched donor mice was isolated from femur and tibia of both legs, washed, and erythrocytes were lysed. Subsequent $3\times10_6$ bone marrow cells were injected intravenously to reconstitute the mice. 2-3 months after bone marrow transfer tumor development was induced as described previously.

Generation and Administration of Bone-Marrow Derived Dendritic Cells

For administration of bone-marrow derived DCs, bone marrow from C57/BL6 mice or GFP:actin mice was collected from the femurs and tibias of both legs. After washing and lysis of erythrocytes, bone marrow cells were cultured in RPMI (Gibco) complete medium (10% FCS, 1×NEAA, 500 μM β-ME) supplemented with 300 ng/ml Flt3 ligand (eBioscience) for 7 days at a concentration of $2.5\times10_6$ cells/ml. DCs were then activated for 24 h with polyI:C (Invivogen) at a final concentration of 5 μg/ml (pre-heated for 5 min at 95° C.). Activated Flt3 ligand DCs were frozen in aliquots of $5\times10_6$ cells in 90% FCS with 10% DMSO (Sigma) until use for in vivo administration. For each DC preparation, activation marker expression was analyzed using flow cytometry with the majority of cells being $CD11c^+$, $CD11b^+$, predominantly $CD8\alpha^+$ and after activation high expression of CD80, CD86, MHCII and CD40. Injection of DCs was initiated when first signs of tumor lesions were identified on mice (2-3 weeks after induction) and were given intra-dermal/intra-tumoral using a 27G (Braintree) needle twice per week at a dose of $1\times10^6$ DC per injection.

Gene Array Analysis of Mouse Tumor Tissue

For gene array analysis, RNA from whole tumor tissue was isolated. Subsequent experimental procedures were performed by the University of Chicago Genomics Core facility using the Illumina MouseWG-6 gene array chip (Illumina) according to manufacturer's instructions. Subsequent gene lists were analyzed from differentially expressed genes with a cut of for at least 2-fold change between the two analyzed cohorts. Significance was determined using a two-way Anova test.

Transwell Migration Assay

Dendritic cell populations were isolated from lymph nodes and skin of naïve 6 week-old C57BL/6 mice. For this purpose, skin tissue was digested in a similar way as tumor tissue and\ cells from skin and lymph node were stained using the previously described protocol for cell sorting. Subsequently, living, $CD45^+$, $CD11c^+$, $CD8\alpha^-$ or $CD8\alpha^+$ cells were isolated from the lymph node sample as well as living, $CD45^+$, $CD11c^+$, $CD103^+$ from skin samples. Migration assays were performed as described previously with minor adaptations using $5\times10_5$ cells/well and pre-treatment of DC with pertussis toxin (Sigma) at a final concentration of 20 ng/ml for 1.5 h in indicated (Spranger et al. Journal of immunology 185, 738-747 (2010); herein incorporated by reference in its entirety). As a migration stimulus, CCL4 (R&D) was added to RPMI complete medium at 500 ng/ml or 48 h conditioned media from BP or BPC cell lines were used. At the endpoint, cells from the lower compartment as well as the trans-well were harvested and counted using a standard Neubauer counting chamber. Percentage of migrated cells was calculated as followed: count lower-well/(count upper-well+ count lower-well)*100; with the sum of trans-well and lower well-being >90% of the input cell count.

ELISA

ELISA assays against murine and human CCL4 were performed using CCL4-specific ELISA kits (R&D) according to manufacturer's instructions.

siRNA Knock-Down

Target gene-specific and control siRNAs were obtained from Ambion. For knock-down, $3 \times 10^4$ tumor cells are plated in 96-well plates at a concentration of $3 \times 10^5$/ml. Opti-MEM (Gibco) was mixed with 1.2 pmol siRNA and 1.5% RNAiMAX reagent (Invitrogen) and added to the culture at a ratio of 1:5. Cells were incubated for 48 hours before supernatant was harvested for ELISA assays and cell were collected for RNA or protein extraction.

Western Blotting

Cell lysates were generated using RIPA buffer in combination with protein inhibitor (Invitrogen) and protein concentration was determined using Bradford protein assay (Biorad). Denaturated lysates were applied to a 10% SDS page and blotted using standard procedures. For protein detection, primary antibodies (β-catenin clone: D10A8, β-actin clone: 13E5, Cell Signaling) were incubated overnight and secondary antibodies (donkey anti-rabbit-HRP (GE Healthcare) for 2 h. Chemiluminescence was used to visualize the protein bands (GE Healthcare).

ChIP-Assay

For ChIP-assays, the two cell lines BP and BPC were grown to 80% confluence in a 10 cm petri dish. Cells were fixed with 1% formaldehyde solution for 30 min at 37° C. Subsequent steps were performed using the EpiTect ChIP kit (Qiagen) according to manufacturer's instructions with some minor adaptations. The formaldehyde was removed and cells were washed prior to harvesting using RIPA buffer. Sonication was performed using a water bath sonicator (GE) with the following cycle of 30 sec on/15 sec off at maximum voltage for 15 minutes, and this cycle repeated 3 times at 4° C. Chromatin-containing supernatants were incubated with an ATF3-specific antibody (mouse: polyclonal rabbit IgG, human: clone 44C3a, mouse IgG, Abcam) or rabbit/mouse IgG1 Isotype (cell signaling) for 3 h/overnight at a 1:50 dilution. Pulled down DNA was used as template for qPCR using Sybr green master mix and primers. Results were calculated as followed: $\Delta CT = (\Delta CT_{IP} - \Delta CT_{IP} - \log 2_{100})$, Fold enrichment = $2_{(\Delta CTiso - \Delta CTIP)}$.

Monoclonal Antibody Therapy

Therapy using monoclonal antibodies was initiated either when first tumor was palpable or seven days after DC injection was initiated. Mice were assigned to groups in a randomized fashion based on their ear tag number. Antibodies (CTLA-4 clone 9H10, PD-L1 clone 10F.9G2; BioXcell) were administered every other day throughout the experiment at a dose of 100 g/mouse/treatment.

Example 2

Experimental Results (Methods in Example 1)

Figure 6:
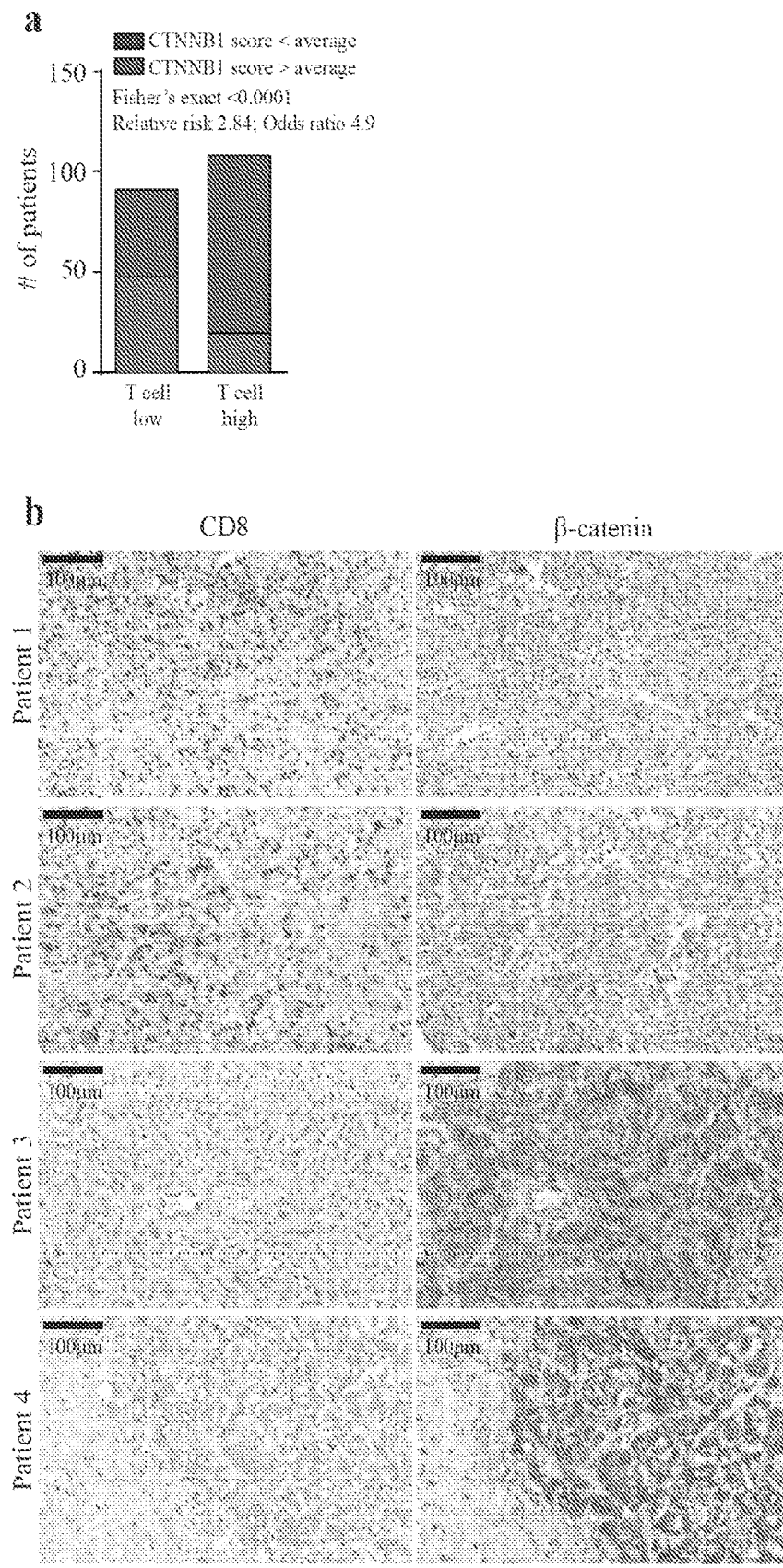
FIG. 6A-B. Correlation between active β-catenin and CD8 T cell infiltrate in human patients. (a) A continuous numerical score was generated using six β-catenin target genes (CTNNB1 score). Utilizing this score, patients from the TCGA data set were grouped in high or low CTNNB1 score (centered on the average score) (low 91; high 108 patients). Subsequent correlation analysis was performed using a Fisher's exact test. (b) Representative examples for CD8 and β-catenin staining in human needle biopsies used for analysis shown in FIG. 1d. A total of 49 samples (25 β-catenin positive and 24 β-catenin negative) was analysed for their degree of CD8+ T cell infiltration with greater than 50 CD8+ T cells/mm$^2$ being considered as T cell-inflamed.

In order to identify oncogenic pathways associated with the presence or absence of a T cell infiltrate, RNA-sequencing was analyzed from 266 metastatic human cutaneous melanomas from the TCGA database. Supervised hierarchical clustering, based on 13 genes previously linked with the presence of a T cell infiltrate, was used to categorize samples into those with low expression of T cell-signature genes (non-T cell-inflamed) versus high expression of T cell signature genes (T cell-inflamed)[7,12,13]. Samples with poor segregation were designated as intermediate and excluded from downstream analysis (FIG. 1a). A similar segregation was observed when hierarchical clustering was performed on primary melanoma samples from the TCGA data set (n=68, data not shown). Global gene expression profiling comparing the T cell inflamed versus the non-T cell-inflamed melanoma samples revealed 1755 genes to be expressed at significantly higher levels in the non-inflamed patient cohort (q<0.01) while 3178 genes were expressed at significantly lower levels. The majority of genes with reduced expression in the non-T cell-inflamed melanomas could be attributed to the lack of immune cells. However, genes expressed at higher levels were focused on in this subset, to gain information about molecular pathways preferentially activated in melanomas lacking a T cell infiltrate. Pathway analysis was performed comparing 91 non-T cell-inflamed to 106 T cell-inflamed patients, which gave evidence for active β-catenin-signaling (APC2, Sox2, Sox11 and Wnt7b expression; p=0.00116) as well as dermatan-sulfate-biosynthesis (HS6ST2 and NDST3 expression; p=0.00196) in the non-T cell-inflamed cohort. Previous reports have suggested that active β-catenin-signaling in malignant melanoma could be associated with a more aggressive Disease (Damsky et al. Cancer cell 20, 741-754 (2011).; Rimm et al. The American journal of pathology 154, 325-329 (1999); herein incorporated by reference in their entireties). To determine whether activation of the β-catenin pathway could be mediated by mutations in this signaling cascade, exome-sequencing data was analyzed for all 197 patients used previously in the pathway analysis. Indeed, seven tumor samples (7.7%) with the non-T cell-inflamed phenotype showed gain of function mutations in the β-catenin (CTNNB1) gene itself, versus one case in the T cell-infiltrated. In addition, loss of function mutations in negative regulators of the pathway (APC, Axin1, TCF1) were identified in 10 of the non-T cell-inflamed tumors (11%). To identify the total percentage of patients showing evidence for an active β-catenin pathway, the gene expression profile was assessed of six well-characterized and positively regulated β-catenin target genes, found to be upregulated in patients with activated CTNNB1 mutations (Herbst et al. BMC genomics 15, 74 (2014); herein incorporated by reference in its entirety). This analysis identified that 48.4 percent (44 patients) of the melanomas in the non-T cell-inflamed subset showing expression of at least five of the six β-catenin target genes versus 3.8 percent (4 patients) of the T cell-inflamed tumors (FIG. 1b). While several cases could be linked to the previously described mutations (CTNNB1 14%;

APC/Axin1/TCF1 23%) the majority (61%) of remaining cases showed increased expression of either a Wnt-ligand family member (Wnt7b, 29.5%; 13 patients) or a receptor family member (Fzd3, 20.5%; 9 patients) or β-catenin itself (11%; 5 patients). The sum of hallmarks leading to active Wnt/β-catenin signaling were higher within the T cell signature-low patient cohort (48% in T cell signature low vs 28% in T cell signature high, Fisher's exact test p=0.0002, odds ratio 3.71). Subsequently, a numerical continuous score was used, based on those six β-catenin target genes (CTNNB1 score), which enabled us to ask whether an active β-catenin signature would be a predictive marker for the presence of a CD8+ T cell infiltrate. By comparing the T cell signature-low and -high patient cohorts using a Fisher's exact test (p<0.0001), that an increased CTNNB1 score was predictive for the lack of T cells with an odds ratio of 4.9 was identified (FIG. 6a). A correlation analysis was performed between selected β-catenin target genes and CD8α transcript levels, which revealed that c-myc, TCF1, and Wnt7b were negatively correlated with CD8α expression (FIG. 1c). As a control, the positively associated relationship between PD-L1 and CD8α expression was tested (Spranger et al. Science translational medicine 5 (2013); herein incorporated by reference in its entirety) and a strong positive correlation was found between these two transcripts. Together these mutations accounted for 39 percent of patients (17 cases) with an active β-catenin signature. To further test the association biopsies from a different patient cohort were used and their status was determined for β-catenin as well as CD8+ T cell infiltration via immunohistology staining. A total of 49 samples (25 β-catenin positive and 24 β-catenin negative, examples FIG. 6b) was analyzed for their degree of CD8+ T cell infiltration with greater than 50 CD8+ T cells/mm² being considered as T cell-inflamed. It was found that the majority of β-catenin-positive tumors showed the non-T cell-inflamed phenotype (84%) while the β-catenin negative tumors were predominantly T cell-inflamed (71%) (FIG. 1d).

Figure 7:
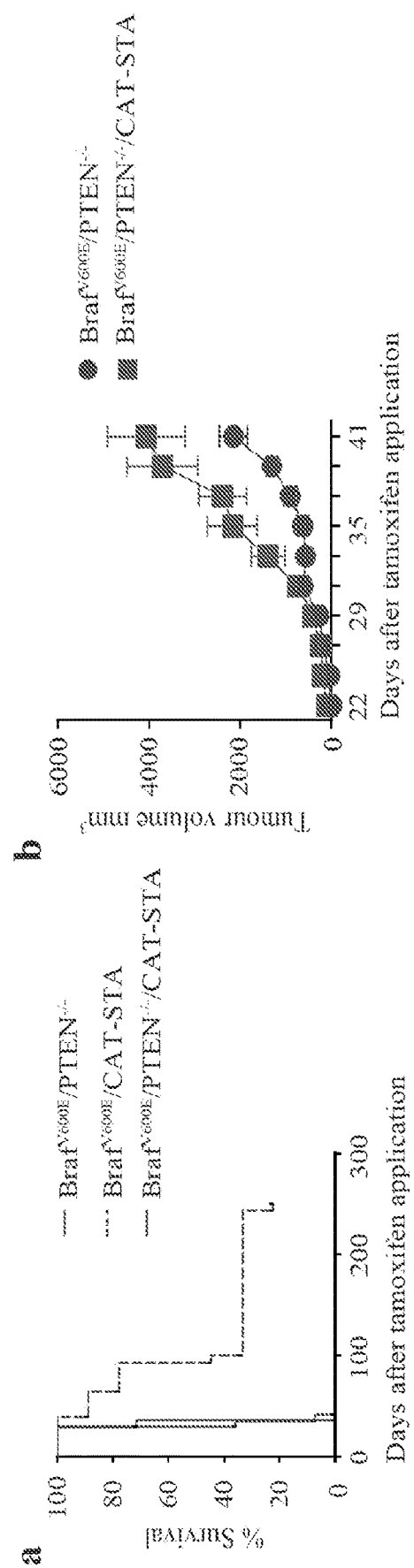
FIG. 7A-E. Tumor growth of genetically engineered mice. (a) Overall survival of all three models: $Braf^{V600E}/PTEN^{-/- with}$ 100% lethality and mean time to death of 31 days, $Braf^{V600E}/CAT\text{-}STA$ with 85% lethality and mean time to tumor event of 93 days and $Braf^{V600E}/PTEN^{-/-}/CAT\text{-}STA$ with 100% lethality and mean time to tumor event of 36 days. (b) Tumor outgrowth of $Braf^{V600E}/PTEN^{-/-}$ and $Braf^{V600E}/PTEN^{-/-}/CAT\text{-}STA$ tumors shown as mm$^3$ at days after TAM application. (c) Representative macroscopic pictures for tumor growth over time when TAM was applied on the lower back of the mouse. (d) Gene array analysis of tumors isolated from GEMs. (e) Histology slides showing representative examples for hematoxylin and eosin stain in all three mouse models (left panel 20x, scale bars indicates 100 $\alpha\mu$; right panel 100x, scale bar indicates 20 $\alpha\mu$).
Figure 7:
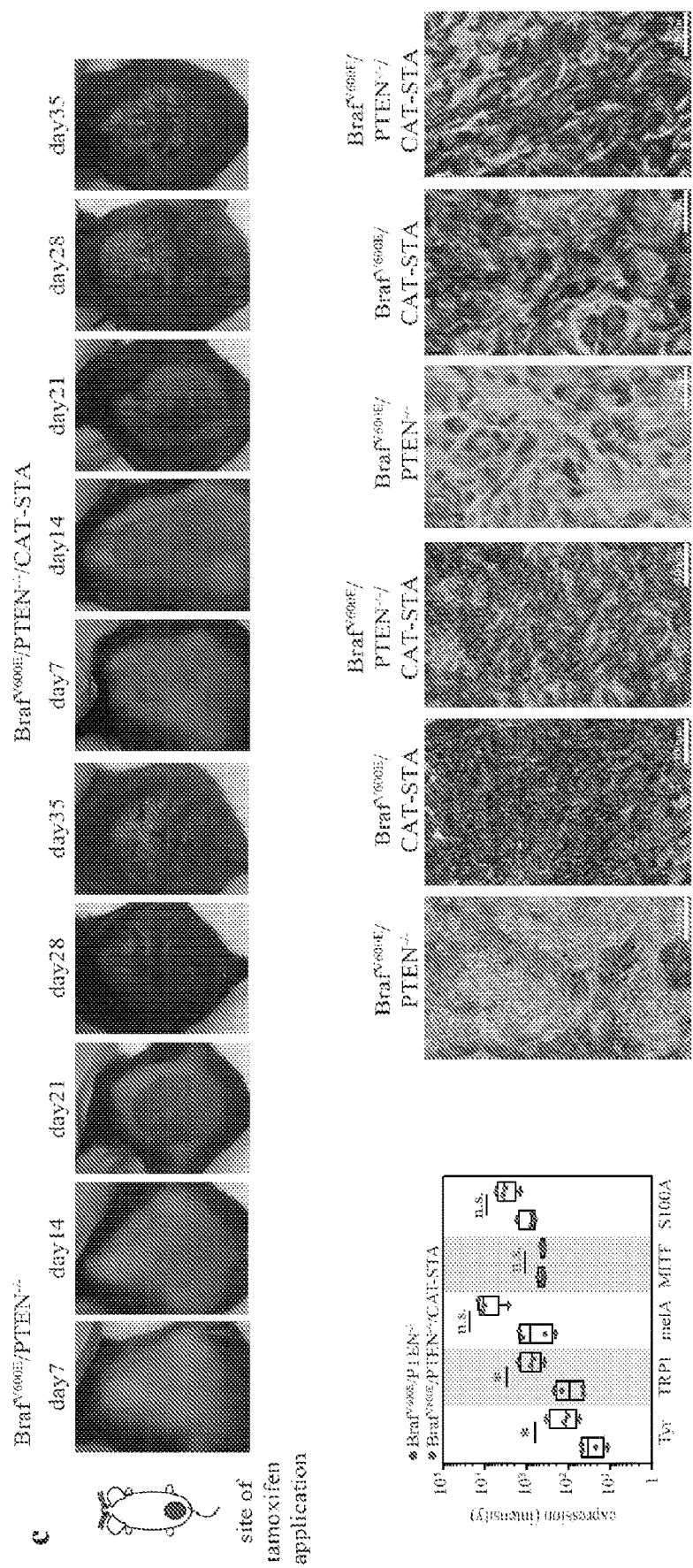
Figure 8:
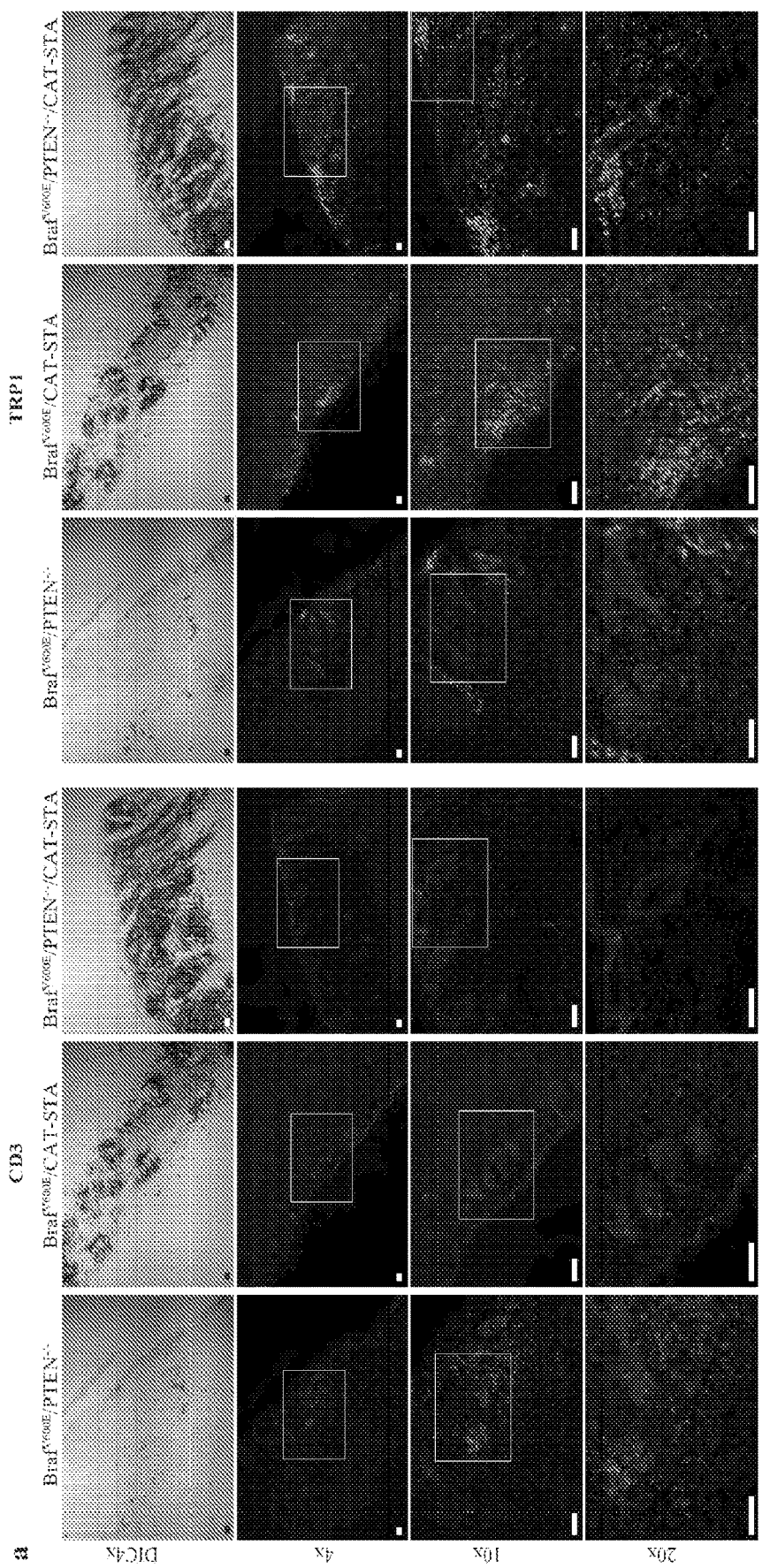
FIG. 8A-C. T cell infiltration of genetically engineered mice. (a) Representative images of immmunofluorescent staining against CD3 (left panel) and TRP1 (right panel) in all three tumor tissues (scale bar 100 $\alpha\mu$, 4x, 10x, 20x with 4xDIC on top; nuclei Hoechst 20x CD3 stain as shown in FIG. 1). (b) Representative immmunofluorescent staining against CD3 (left panel) and TRP1 (right panel) in a highly pigmented area of $Braf^{V600E}/PTEN^{-/-}$ tumor tissues (scale bar 100$\alpha\mu$, 10x, 20x with 10xDIC left) excluding that the lack of T cells is associated with increased pigmentation (nuclei Hoechst). (c) Numbers of CD3+ T cells were counted within 13 different fields (0.5 mm×1 mm) from two tumor samples. Mean of 12 T cell or 3.2 T cell per 0.5 mm$^2$ in $Braf^{V600E}/CAT\text{-}STA$ or $Braf^{V600E}/PTEN^{-/-}/CAT\text{-}STA$, respectively versus 100 T cells per 0.5 mm$^2$ in $Braf^{V600E}/PTEN^{-/-}$. Data are given as mean with min and max, as well as individual values. Statistical analysis was performed using Mann-Whitney U test.
Figure 8:
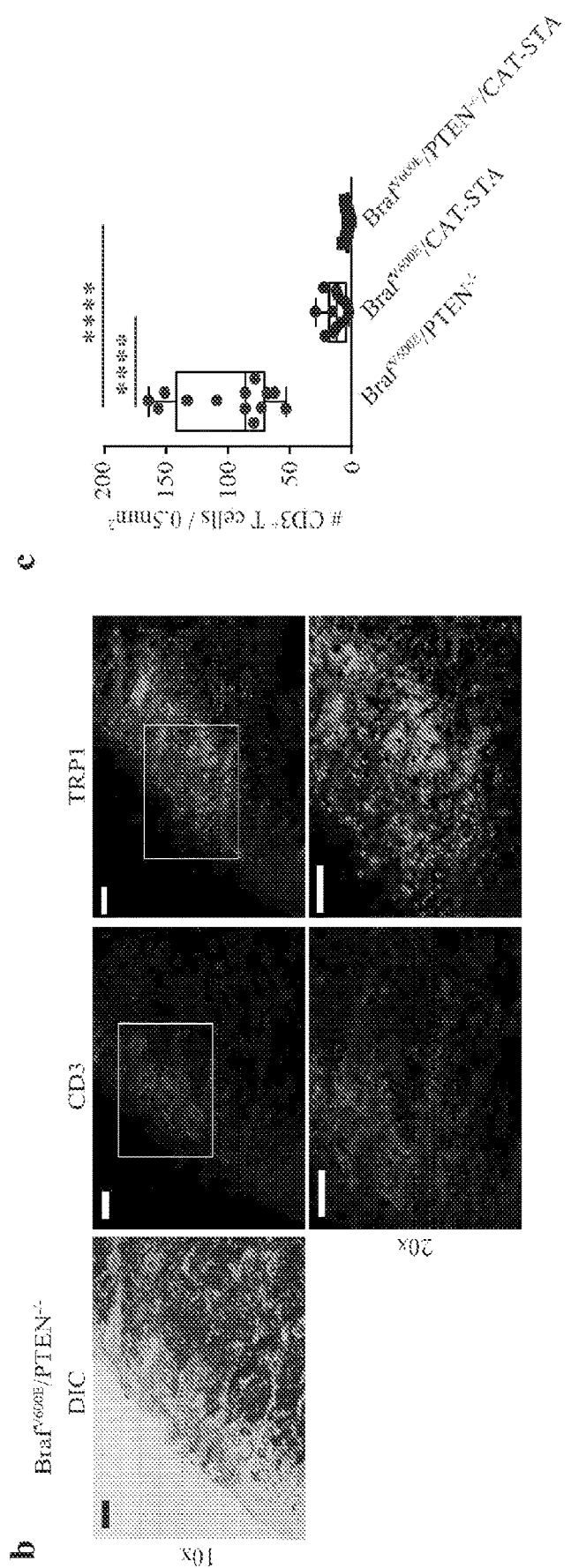

Based on these correlative observations, it was investigated directly whether active (β-catenin-signaling within tumor cells could adversely affect anti-tumor T cell responses and T cell-infiltration into the melanoma tumor-microenvironment using inducible autochthonous mouse models. Melanocyte-specific activation of Cre was achieved using transgenic mice expressing Cre-ER controlled by the tyrosinase promoter. These mice were interbred with mice contain a $Braf^{V600E}$ allele knocked-in to the endogenous locusts along with a LoxP-flanked insulator sequence, and also to conditional $PTEN_{-/-}$ mice. In this model, topical application of 4-OH-tamoxifen (TAM) results in development of melanoma in the region of the treated skin with 100% penetrance (Dankort et al. Nature genetics 41, 544-552 (2009); herein incorporated by reference in its entirety). To assess a functional role for tumor-intrinsic β-catenin, conditional $Braf^{V600E}$ knock-in mice were also interbred with mice bearing a conditional active β-catenin allele (Gounari, F. et al. Oncogene 21, 4099-4107 (2002); Harada et al. The EMBO journal 18, 5931-5942 (1999); herein incorporated by reference in their entireties), with or without homozygous conditional PTEN deletion. Mice bearing the $Braf^{V600E}/PTEN^{-/-}$ combination developed tumors after a median duration of 21 days, whereas those bearing the $Braf^{V600E}/CAT$-STA or $Braf^{V600E}PTEN^{-/-}/CAT$-STA permutation developed tumors after a median 55.5 days or 26 days, respectively (FIG. 1e and FIG. 7a-c). Further analysis focused on $Braf^{V600E}/PTEN^{-/-}$ and /$PTEN^{-/-}$/CAT-STA due to their similar rate of onset and growth curves (FIG. 7b-c). Using gene array analysis as well as histological analysis it was confirmed that the developing tumors were indeed melanoma FIG. 7d-e) (Dankort et al. Nature genetics 41, 544-552 (2009); Damsky et al. Cancer cell 20, 741-754 (2011).; herein incorporated by reference in their entireties). Consistent with the findings of Bosenberg and colleagues it was found that $Braf^{V600E}/PTEN_{-/-}$ tumors showed reduced pigmentation (accompanied by reduced TRP1 expression) compared to tumors with active β-catenin signaling FIG. 7d-e and 8a).

In order to determine whether tumor-intrinsic expression of active β-catenin adversely affected the accumulation of a T cell infiltrate, tumors were induced by TAM in mice bearing the above three genotype permutations, and when tumors reached a size of around 3000 mm³ they were analyzed by flow cytometry. $Braf^{V600E}/PTEN^{-/-}$ tumors indeed showed presence of CD3+ T cells. However, $Braf^{V600E}/CAT$-STA tumors as well as $Braf^{V600E}/PTEN^{-/-}/CAT$-STA tumors showed almost a complete absence of T cells in the tumor-microenvironment (FIG. 1f). Fluorescent immune-histology confirmed the absence of intratumoral CD3+ T cells in $Braf^{V600E}/PTEN^{-/-}/CAT$-STA tumors (mean of 12 T cell or 3.2 T cell per 0.5 mm² in $Braf^{V600E}/CAT$-STA or $Braf^{V600E}/PTEN^{-/-}/CAT$-STA versus 100 T cells per 0.5 mm² in $Braf^{V600E}/PTEN^{-/-}$) (FIGS. 1g and 8a-c) with only rare T cells observed in the epidermis. Additional immunohistochemistry of regions of higher pigmentation within $Braf^{V600E}/PTEN^{-/-}$ tumors indicated a similar degree of T cell infiltration indicating that pigmentation intensity itself did not correlate with absence of T cells (FIG. 7e).

Results indicate that tumor-intrinsic β-catenin pathway activation dominantly excludes T cell infiltration into the melanoma tumor-microenvironment.

Figure 2:
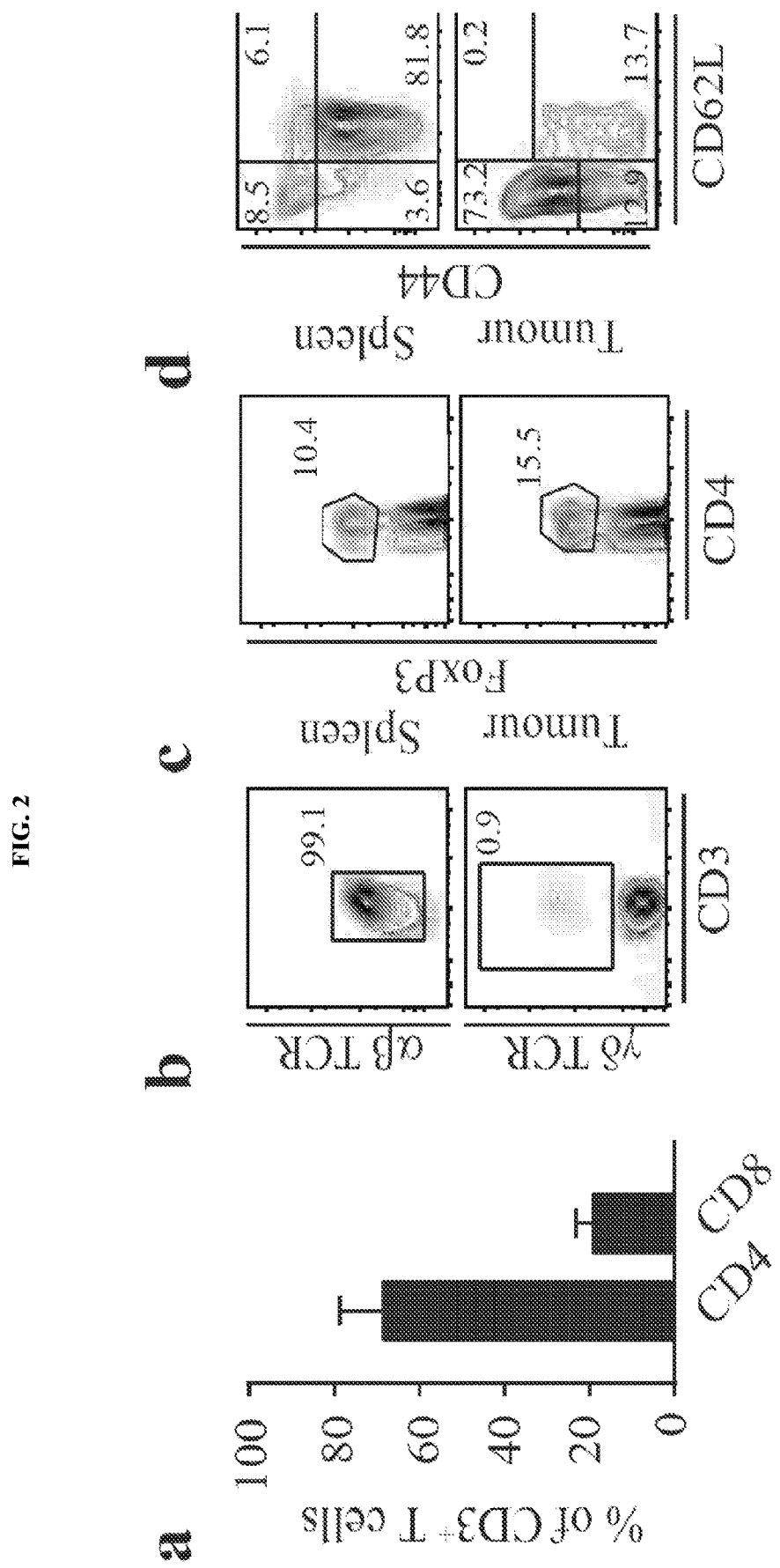
FIG. 2A-I. $Braf^{V600E}/PTEN^{-/-}/CAT\text{-}STA$ mice show impaired priming of anti-tumor T cells. (a) Distribution of T cell subsets in $Braf^{V600E}/PTEN-/-$ tumors. (b-e) Representative flow cytometry plots to discriminate (b) αβ-TCR T cells and αβ-TCR T cells, (c) FoxP3+ T regulatory cells, (d) naïve (CD62L+CD44−) and effector (CD62L−CD44+) T cells (pre-gated on CD3+CD8+ T cells) and (e) PD-1 and Lag3 positive T cells (pre-gated on CD3+CD8+ T cells). (f) Quantification of PD-1/Lag3 double-positive T cells. (g) IL-2-transcripts present in sorted CD3+ T cells. (h) Abundance and proliferation (CFSE dilution) of 2C-TCRTg T cells. Depicted are representative examples pre-gated on alive, CD45+CD3+CD8+. (i) Statistical analysis of (h).
Figure 2:
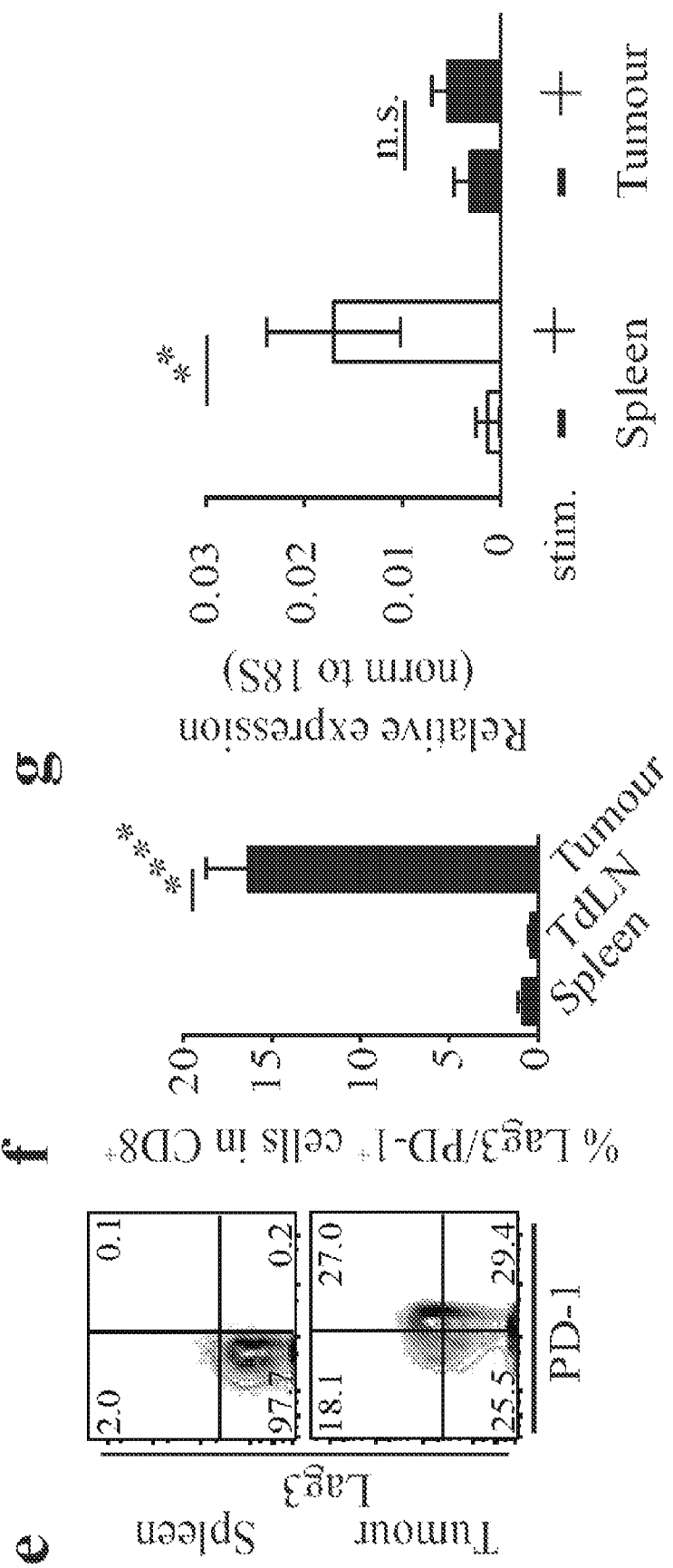
Figure 2:
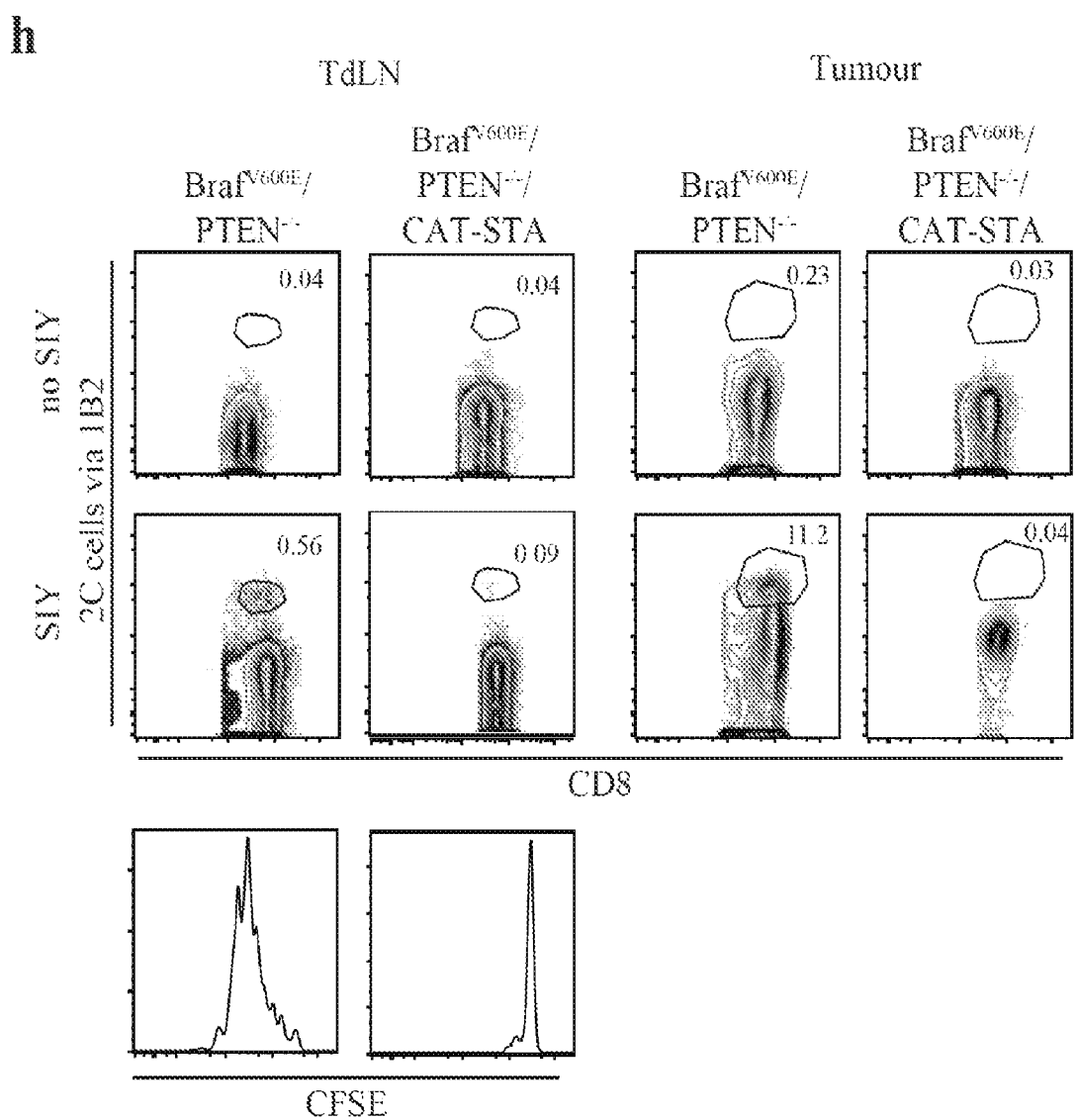
Figure 2:
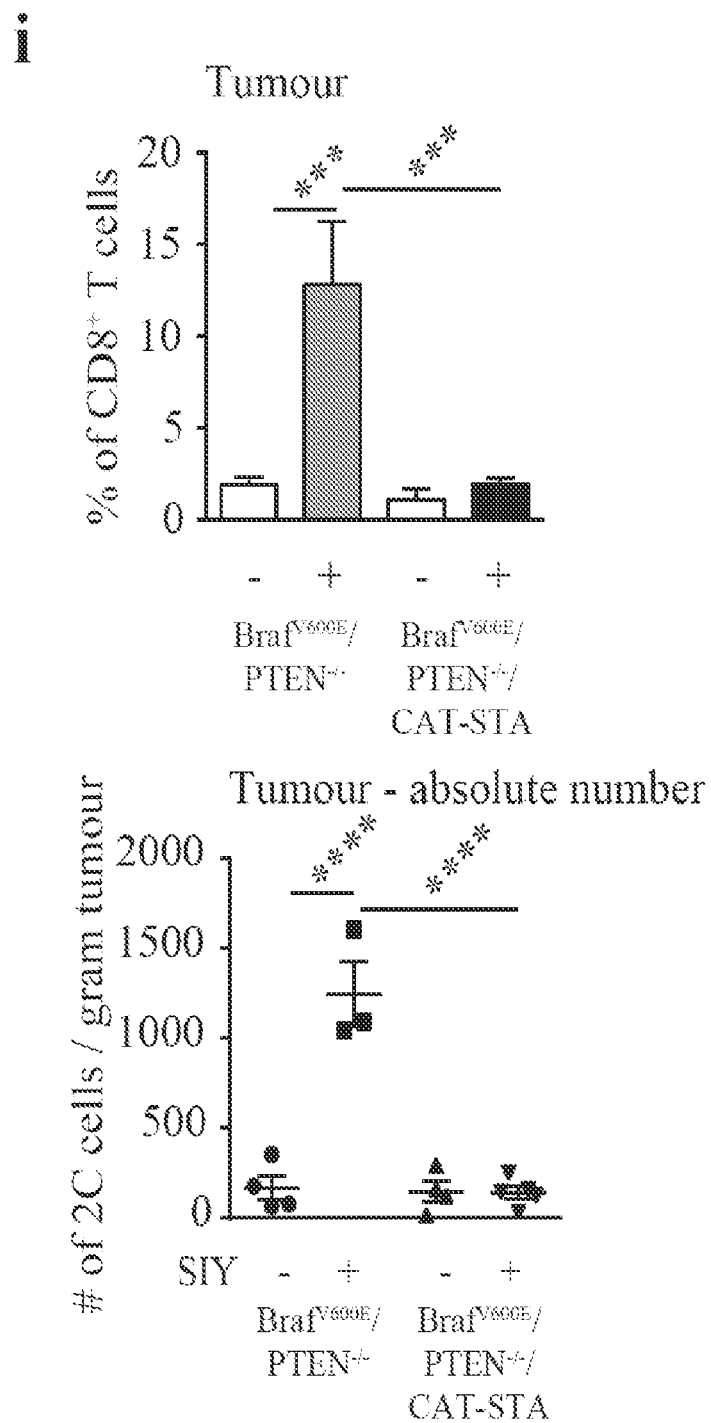
Figure 9:
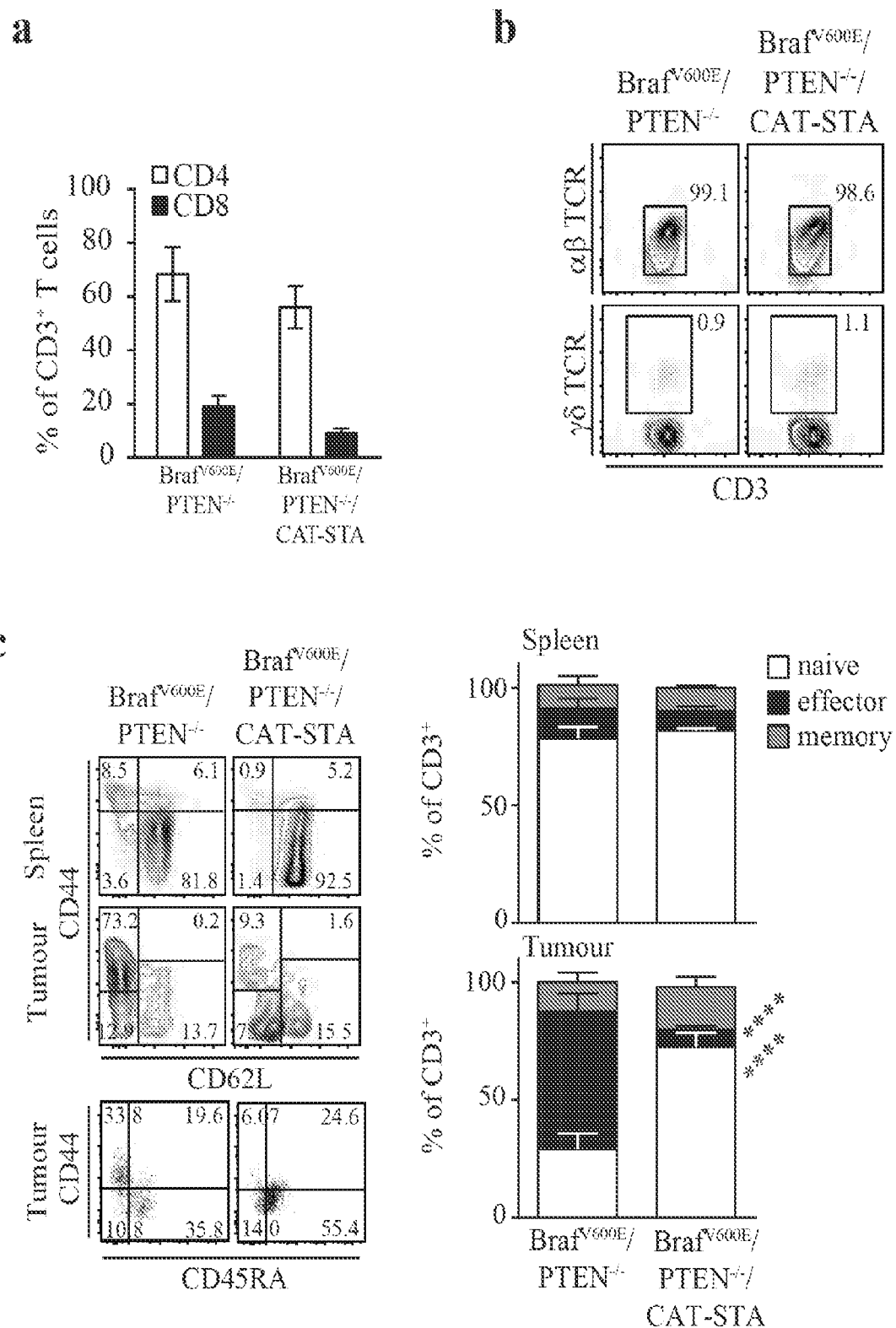
FIG. 9A-K. Characterization of the T cell infiltrate in $Braf^{V600E}/PTEN^{-/-}/CAT\text{-}STA$ mice. (a) Distribution of T cell subsets in $Braf^{V600E}/PTEN^{-/-}$ and $Braf^{V600E}/PTEN^{-/-}/CAT\text{-}STA$ tumors. (b-c) Representative flow cytometry plots to discriminate (b) αβ-TCR T cells and γδ-TCR T cells, (c) naïve (CD62L+CD44−) and effector (CD62L−CD44+) T cells (pre-gated on CD3$^+$CD8$^+$ T cells) and one representative example of CD44/CD45RA staining. Quantification of naïve (CD62L$^+$CD44$^-$CD45RA$^+$), effector (CD62L$^-$CD44$^+$CD45RA$^-$) and memory (CD62L$^+$CD44$^+$CD45RA$^-$) is indicated on the right. (d) Representative flow cytometry plots of FoxP3$^+$ T regulatory cells. (e) Quantification and comparison to Braf$^{V600E}$/PTEN$^{-/-}$ of PD-1/Lag3 double-positive T cells (n=12). (f) Representative flow cytometry ploPD-1 and Lag3 positive T cells (pre-gated on CD3$^+$CD8$^+$ T cells) in Braf$^{V600E}$/PTEN$^{-/-}$ tumors. (g) IL-2-transcripts present in sorted CD3$^+$ T cells from Braf$^{V600E}$/PTEN$^{-/-}$ tumors and spleen. (h) IFN-Γ transcripts present in sorted CD3$^+$ T cells from Braf$^{V600E}$/PTEN$^{-/-}$ and Braf$^{V600E}$/PTEN$^{-/-}$/CAT-STA mice. (i) Expression level of PD-L1 in whole tumor tissue from both mouse models assessed by qRT-PCR. (j) Flow cytometric analysis of PD-L1 expression of non-hematopoietic tumor cells (CD45$^-$), CD45$^+$CD11c$^+$DC and CD45$^+$CD3$^+$ T cells. Shown is a representative example as histogram with Mean Fluorescent Intensity given each histogram. (k) Percentage of Gr1$^+$ cells within the CD11b$^+$ fraction of the tumor immune cell infiltrate (absolute numbers Braf$^{V600E}$/PTEN$^{-/-}$: 1047±418 cell/gram tumor to Braf$^{V600E}$/PTEN$^{-/-}$/CAT-STA: 739±185 cell/gram tumor).
Figure 9:
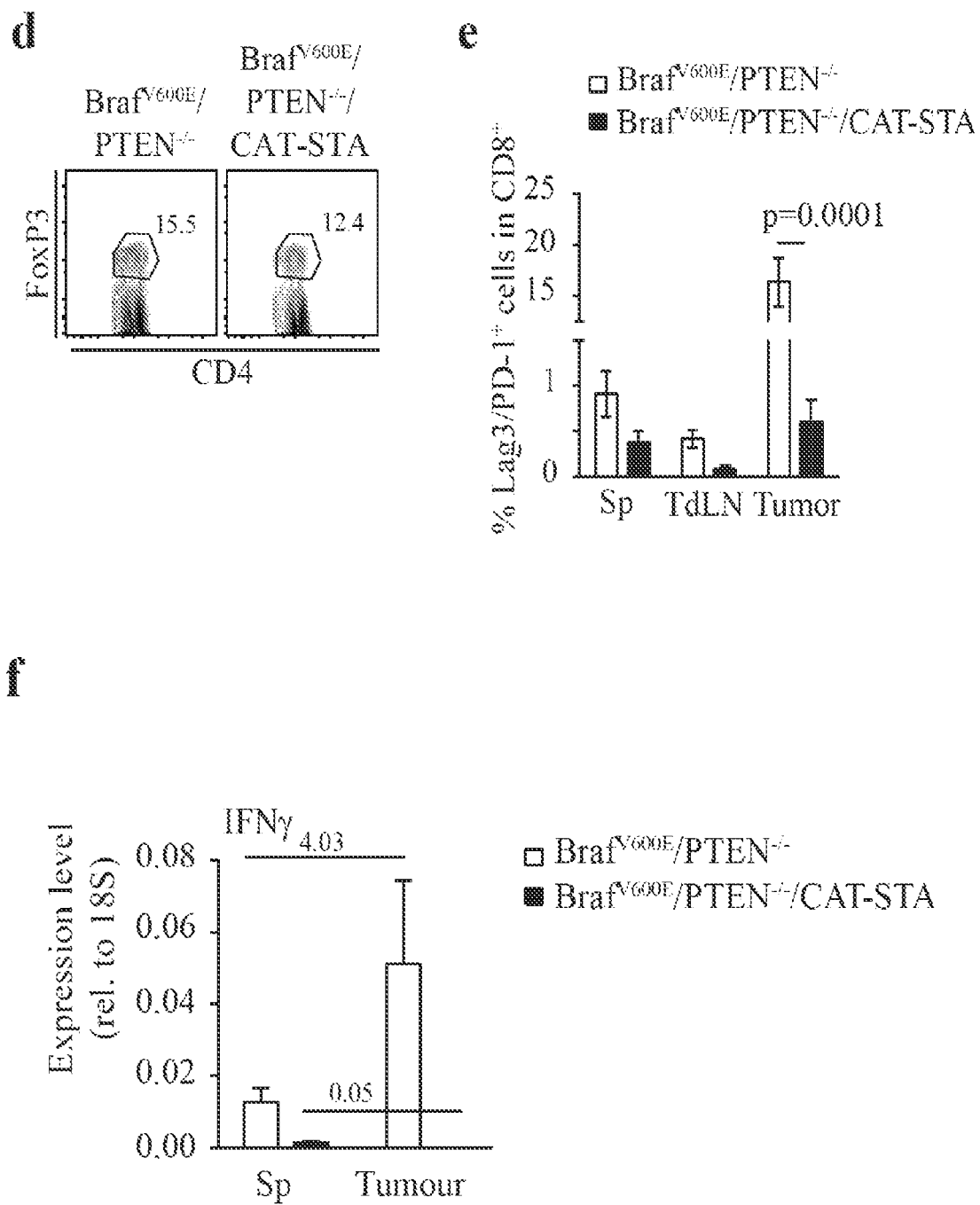
Figure 9:
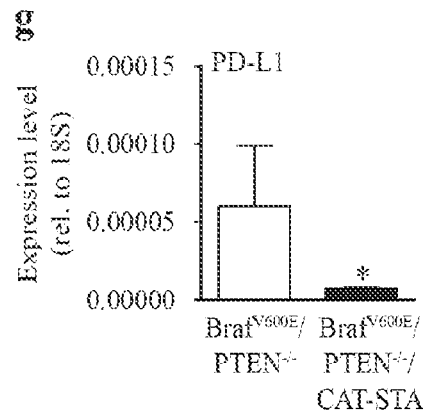
Figure 9:
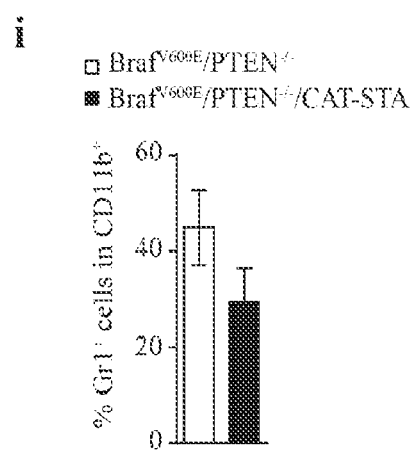
Figure 9:
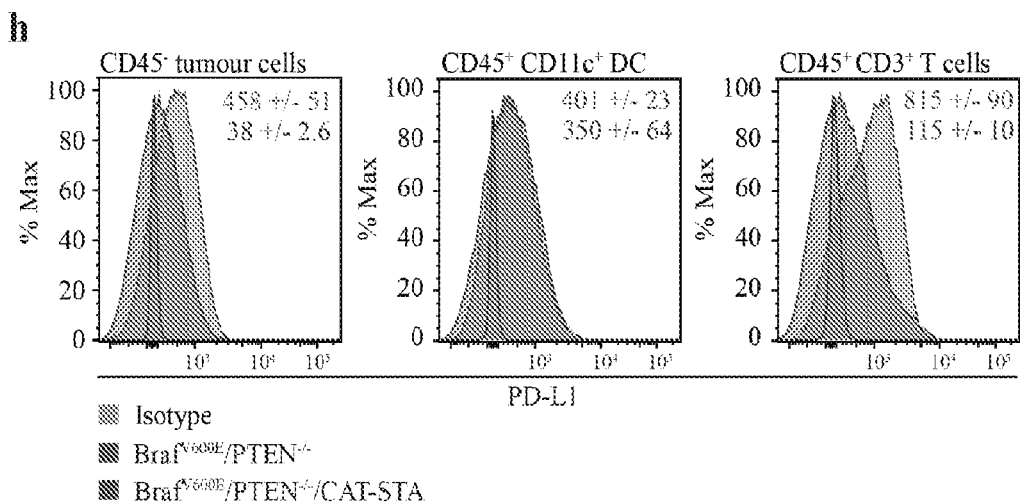

The T cell infiltrate in $Braf^{V600E}/PTEN^{-/-}$ tumors was analyzed further phenotypically and contained of both CD4+ and CD8+ T cells with the vast majority of them expressing the αβ-TCR and not the αβ-TCR, the T cell subset mainly found in healthy skin (FIG. 2a-b). The majority of the T cells present were $CD44_{hi}/CD62L_{lo}/CD45RA_{lo}$, suggesting an activated phenotype (FIGS. 2d and 9c) and 6% FoxP3+ regulatory T cells were also detected, comparable to levels detected in peripheral lymphoid organs (FIG. 2c). Additionally, CD8+ T cells from $Braf^{V600E}/PTEN^{-/-}$ tumors showed expression of PD-1 and Lag3 (FIG. 2e-f), indicating an acquired phenotype of T cell dysfunction previously reported in transplantable tumor models (Woo et al. Cancer Res 72, 917-927 (2012); herein incorporated by reference in its entirety). Consistent with this surface phenotype, sorted CD3+ tumor-infiltrating T cells from $Braf^{V600E}/PTEN^{-/-}$ tumor showed defective IL-2-production compared to T cells sorted from spleen upon stimulation (FIG. 2g). Comparable studies on the few T cells isolated from $Braf^{V600E}/PTEN^{-/-}/CAT$-STA tumors showed predominantly a naïve, non-activated phenotype (FIG. 9a-e). Consistent with those findings increased IFN-γ production was observed in tumor-infiltrated T cells from $Braf^{V600E}/PTEN^{-/-}$ mice compared to splenic T cells while the few T cells isolated from $Braf^{V600E}/PTEN^{-/-}/CAT$-STA tumors did not show increased IFN-γexpression (FIG. 9f). Corresponding with these observations, it was also observed an increase in PD-L1 mRNA expression in $Braf^{V600E}/PTEN^{-/-}$ tumors, which by flow cytometry was identified on CD45-tumor cells and also on T cells, consistent with work linking PD-L1 expression with the presence of CD8+ T cells at the tumor site (FIG. 9g-h) (Spranger et al. Science translational medicine 5 (2013); herein incorporated by reference in its entirety). Models have suggested that increased immune responses against melanoma were associated with reduced differentiation of tumor cells as well as increase inflammation with myeloid-derived suppressor cells (MDSC, CD11b+ Gr1+) (Landsberg, J. et al. Nature 490, 412-416 (2012); Soudja, S. M. et al. Cancer research 70, 3515-3525 (2010); herein incorporated by reference in their entireties). However, significant differences in the percentages or numbers of MDSCs were not detected between the tumor genotypes (Braf$^{V600E}$/PTEN$^{-/-}$:1047±418 cell/gram tumor to Braf$^{V600E}$/PTEN$^{-/-}$/CAT-STA: 739±185 cell/gram tumor; p=0.7429 (FIG. 9i).

Both genetic mouse models were crossed to an additional engineered mouse strain expressing the model antigen SIYRYYGL (SIY) (SEQ ID NO: 7) conditionally in a Cre-dependent manner (Cheung et al. Cancer research 68, 9459-9468 (2008); DuPage, M. et al. Cancer cell 19, 72-85 (2011).; herein incorporated by reference in their entireties). It was investigated whether lack of T cell infiltration into the Braf$^{V600E}$/PTEN$^{-/-}$/CAT-STA tumors was secondary to lack of initial T cell priming against tumor-associated antigen. After tumors were induced by TAM in Braf$^{V600E}$/PTEN$^{-/-}$ and Braf$^{V600E}$/PTEN$^{-/-}$/CAT-STA mice, both±conditional SIY expression, CFSE-labelled SIY-specific TCR transgenic 2C T cells were transferred intravenously. Five days later, accumulation of those adoptively transferred cells and antigen-induced proliferation (CFSE dilution) were assessed in secondary lymphoid organs and within the tumor microenvironment. This short time frame was chosen to avoid the reported leakiness of the SIY transgene that has been associated with partial T cell activation within the spleen. While SIY negative mice failed to accumulate 2C T cells within the tumor-draining lymph nodes (TdLN) or the tumor site, SIY-positive mice showed detectable 2C T cells in the TdLN in both genetic models. However, no proliferation of 2C T cells was identified within the TdLN in the Braf$^{V600E}$/PTEN$^{-/-}$/CAT-STA/SIY$^+$ model while activation of T cells within TdLN of Braf$^{V600E}$/PTEN$^{-/-}$ was brisk (FIG. 2h-i). Consistent with this differential level of activation and expansion, the presence of proliferated 2C T cells was observed at the tumor site exclusively in Braf$^{V600E}$/PTEN$^{-/-}$ mice (FIG. 2h-i). These data indicate that tumor-intrinsic β-catenin-signaling prevents the early steps of T cell priming against tumor-associated antigens in melanoma.

Figure 3:
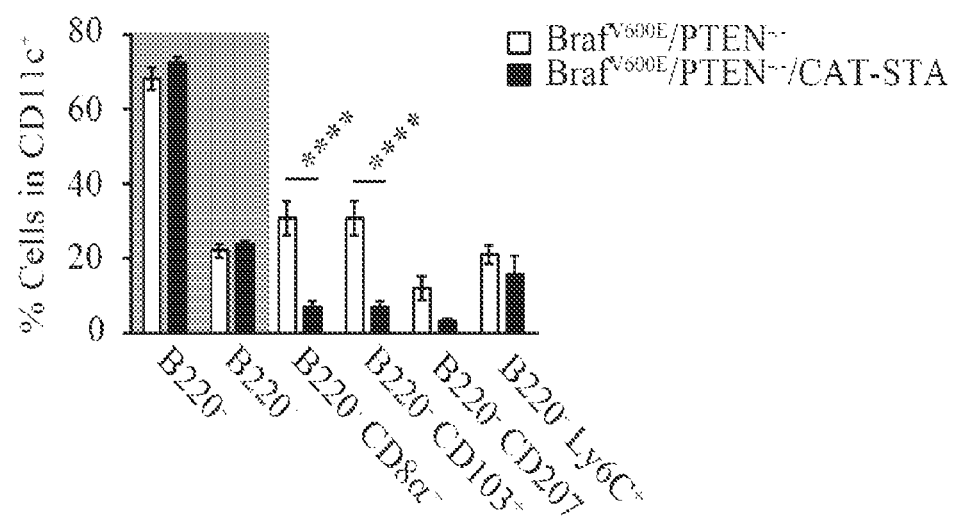
FIG. 3. CD103+ dermal DCs are required for the induction of melanoma-reactive T cells. (a) Percentages of DC subsets within $Braf^{V600E}/PTEN^{-/-}$ and $Braf^{V600E}/PTEN^{-/-}/CAT\text{-}STA$ tumors. (b) Representative example of CD103/CD8α staining (gated CD45+MHCII$_{hi}$CD11c+) (c) Quantification of CD103+ DCs. (d) Amount of CD3+ T cell and CD103+ DC infiltration in $Braf^{V600E}/PTEN^{-/-}$ reconstituted with control (actin:GFP) or $Batf3^{-/-}$ bone marrow and (e) Intratumoral injection of Flt3 ligand-derived DCs into $Braf^{V600E}/PTEN^{-/-}CAT\text{-}STA$ tumors (PBS served as control).
Figure 3:
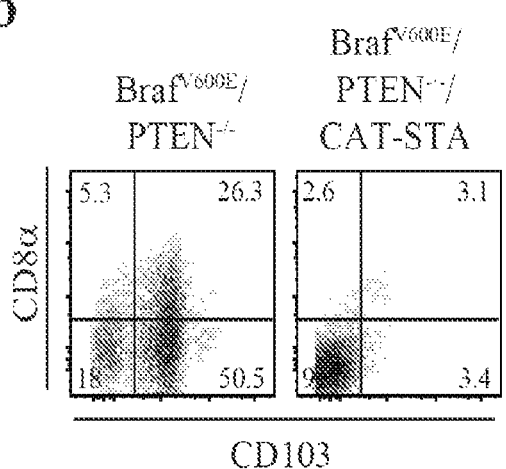
Figure 3:
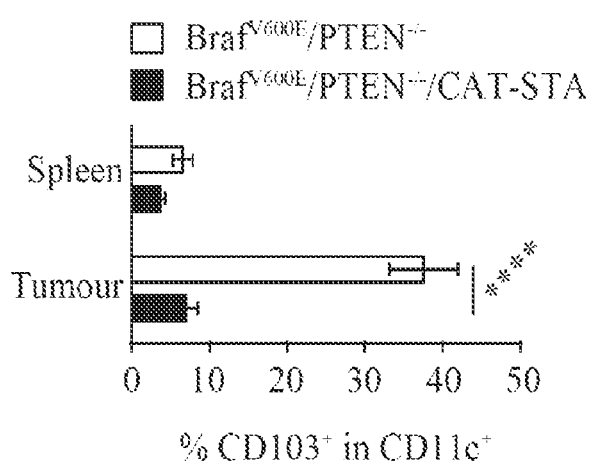
Figure 3:
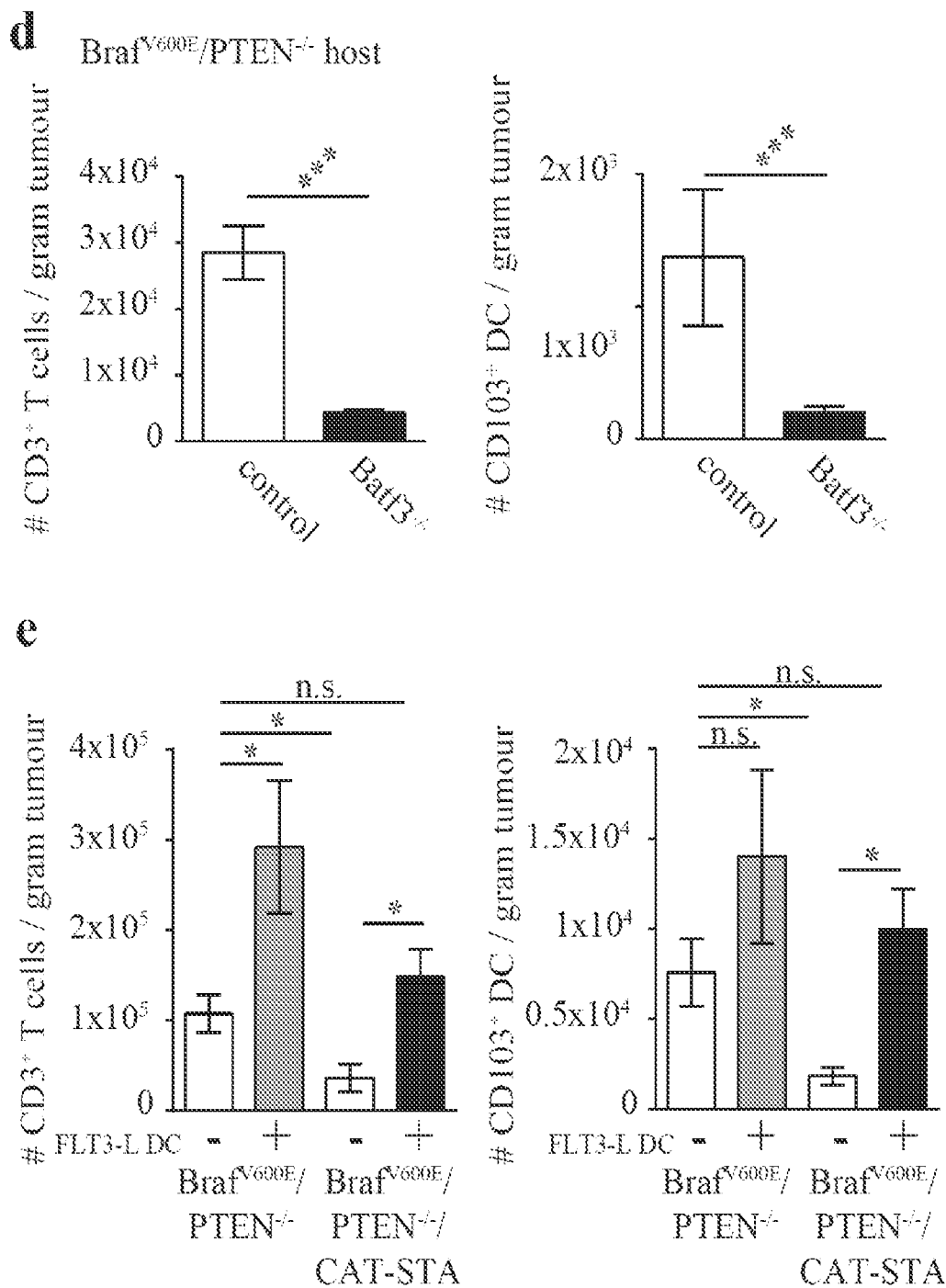
Figure 10:
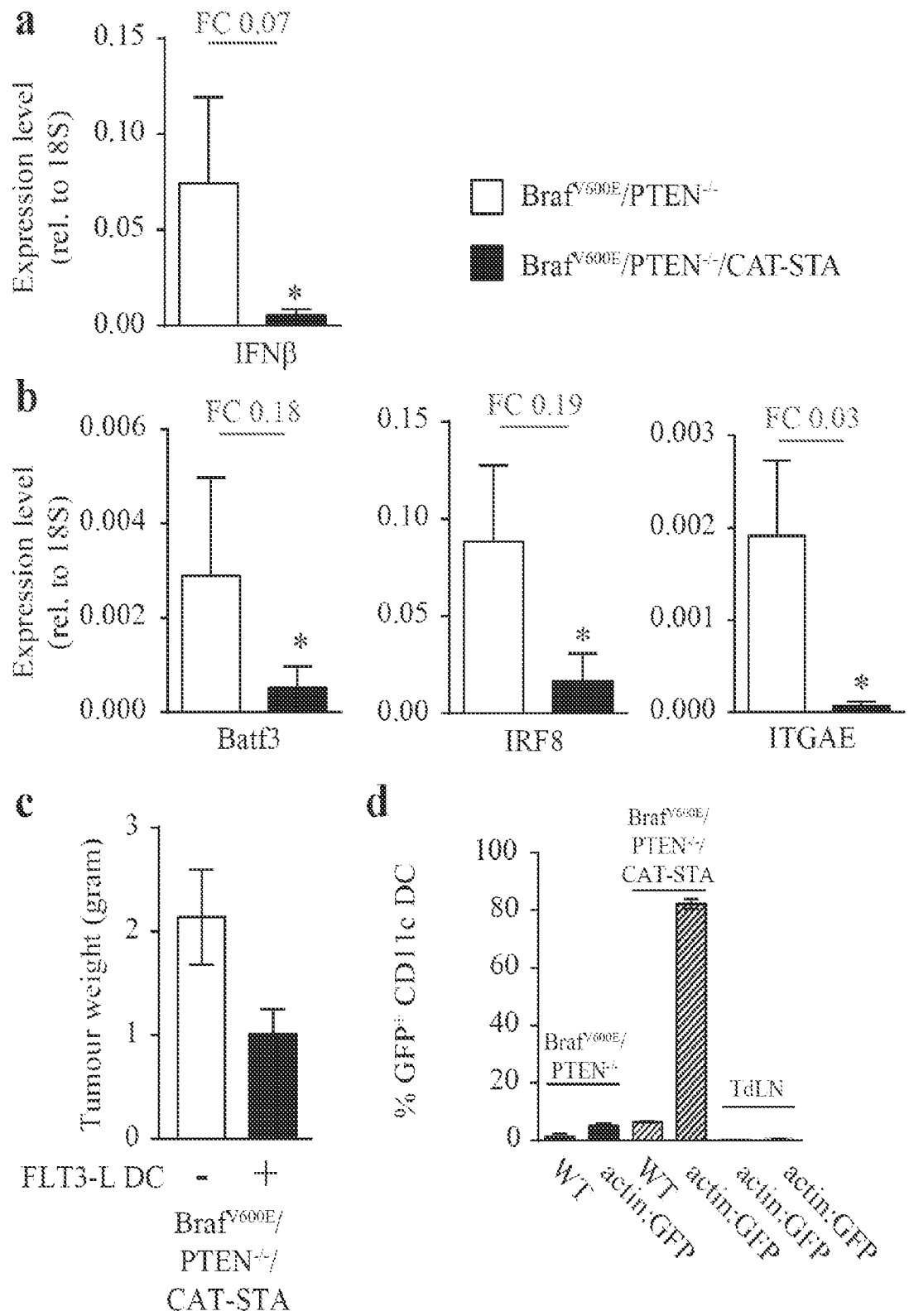
FIG. 10A-D. Injection of Flt3 ligand-derived DCs into tumors of Braf$^{V600E}$/PTEN$^{-/-}$/CAT-STA mice is sufficient to overcome the lack of CD103$^+$ dermal DCs. (a) Expression level of IFN-β in CD45$^+$CD11c$^+$ sorted DC from tumors from Braf$^{V600E}$/PTEN$^{-/-}$ (open) and Braf$^{V600E}$/PTEN$^{-/-}$/CAT-STA (filled) mice. (b) Expression level of Batf3, IRF8 and ITGAE in sorted DCs. Fold-change is indicated in each graph. (c) Mean (±SEM) tumor weight of Braf$^{V600E}$/PTEN$^{-/-}$/CAT-STA assessed at the endpoint of the experiment depicted in FIG. 3e, following intratumoral injection of DCs. (d) Percent of GFP$^+$CD11c$^+$ present at the tumor site after injections of Flt3 ligand-derived DCs from actin:GFP mice. Depicted are the percentages detected in the tumor of both genotypes injected with either WT or actin:GFP DC as well as the TdLN for the actin:GFP injected mice.

The absence of early T cell priming in Braf$^{V600E}$/PTEN$^{-/-}$/CAT-STA tumor-bearing mice suggested a defect at the level of the antigen-presenting cell compartment. Previous work using transplantable tumor models has indicated that the critical antigen-presenting cells subset of cross-priming of tumor antigens to CD8$^+$ T cells was the lineage of DCs driven by the transcriptional regulator Batf3 (Fuertes, M. B. et al. The Journal of experimental medicine 208, 2005-2016 (2011).; Hildner, K. et al. Science 322, 1097-1100 (2008); Engelhardt, J. J. et al. Cancer cell 21, 402-417 (2012); Bedoui, S. et al. Nature immunology 10, 488-495 (2009); herein incorporated by reference in their entireties). The major population of these DCs phenotypically expresses CD8α, but within the skin an additional Batf3-dependent DC subset has been described that expresses CD103 (Edelson, B. T. et al. The Journal of experimental medicine 207, 823-836 (2010); herein incorporated by reference in its entirety). Subsets of DCs (CD45$^+$ MHCII$^+$CD11c$^+$) were phenotypically analyzed within the tumor-microenvironment. Few or no differences were observed in the number of conventional DCs (B220$^-$), plasmacytoid DCs (B220$^1$), monocytes (B220-Ly6C$^+$), or Langerhans DCs (B220$^-$CD207$^+$). Strikingly, the CD8A$^+$ and CD103$^+$DC populations were nearly completely absent from Braf$_{V600E}$/PTEN$^{-/-}$/CAT-STA tumors compared to tumors from Braf$^{V600E}$/PTEN$^{-/-}$ mice (FIG. 3a-c). In particular CD103$^+$ DCs were reduced in the tumors and TdLN from Braf$^{V600E}$/PTEN$^{-/-}$/CAT-STA mice, while they were preserved in the spleen (FIG. 3b-c). Expression of transcripts that have been associated with this DC phenotype was assessed. Sorted tumor-infiltrating CD45$^+$CD11c$^+$ DCs from Braf$^{V600E}$/PTEN$^{-/-}$/CAT-STA and Braf$^{V600E}$/PTEN$^{-/-}$ mice were analyzed by qRT-PCR for expression of Batf3, IRF8, and the integrin ITGAE. Expression of these genes was markedly reduced among DCs from Braf$^{V600E}$/PTEN$^{-/-}$/CAT-STA tumors (FIG. 10a-b). Work using transplantable tumor models had indicated that production of IFN-β was a necessary step upstream from CD8A$^+$ DC activation. In DCs from Braf$^{V600E}$/PTEN$^{-/-}$/CAT-STA tumors, a marked reduction in IFN-β transcripts was also found compared to DCs from Braf$^{V600E}$/PTEN$^{-/-}$ tumors (FIG. 10a). These results indicate that the failed T cell priming against tumor-associated antigen in Braf$^{V600E}$/PTEN$^{-/-}$/CAT-STA tumors is secondary to defective recruitment and activation of Batf3-lineage DCs.

To determine whether T cell-infiltration into Braf$^{V600E}$/PTEN$^{-/-}$ tumors was dependent on CD103$^+$ DCs, bone marrow chimeras with Batf3$^{-/-}$ or control (actin:GFP) bone marrow were generated prior to tumor induction in Braf$^{V600E}$/PTEN$^{-/-}$ mice. Indeed, Braf$^{V600E}$/PTEN$^{-/-}$ tumors from mice reconstituted with Batf3__ bone marrow failed to develop T cell infiltration, which corresponded with absence of CD103$^+$ DCs in the tumor-microenvironment (FIG. 3d). To assess whether poor DC recruitment and activation were indeed the major functional barriers in Braf$^{V600E}$/PTEN$^{-/-}$/CAT-STA tumors, Flt3 ligand-derived bone marrow DC activated with poly I:C were generated, which approximate the CD8A/CD103$^+$ dermal-DC lineage (Mollah, S. A. et al. The Journal of investigative dermatology 134, 1265-1275 (2014); herein incorporated by reference in its entirety). These were introduced by intratumoral administration (twice per week) into tumors of Braf$_{V600E}$/PTEN$^{-/-}$ CAT-STA mice. While other studies have shown a therapeutic efficacy of poly I:C injections alone in an setting where DCs are present at the tumor site, experiments herein used poly I:C activated DC as a surrogate for DCs found in T cell-inflamed tumors which have an existing type I interferon signature FIG. 10a). DC injections were sufficient to restore T cell infiltration in Braf$^{V600E}$/PTEN$^{-/-}$/CAT-STA mice up to similar level as observed in PBS-treated Braf$^{V600E}$/PTEN$^{-/-}$ tumors (FIG. 3e). This effect was associated with a modest reduction in tumor weight in Braf$^{V600E}$/PTEN$^{-/-}$/CAT-STA mice FIG. 10c). Using DCs generated from actin:GFP transgenic mice, it was observed that injected DCs were retained within the tumor-microenvironment of Braf$^{V600E}$/PTEN$^{-/-}$/CAT-STA mice during the time frame of the experiment FIG. 10d). These results indicate that a major immunologic defect in the context of melanomas expressing tumor-intrinsic β-catenin-signaling is defective recruitment of CD103$^+$ dermal DCs.

To elucidate mechanisms that explain failed CD103$^+$ dermal DC recruitment into the tumor-microenvironment (although the present invention is not limited to any particular mechanism of action and an understanding of the mechanism of action is not necessary to practice the present invention), gene expression profiling was performed from tumors obtained from Braf$^{V600E}$/PTEN$^{-/-}$ versus Braf$^{V600E}$/PTEN$^{-/-}$/CAT-STA mice. Because recruitment of inflammatory cells into tissue sites is largely driven by chemokine gradients, experiments focused on chemokine expression (Malissen et al. Nature reviews. Immunology 14, 417-428 (2014); herein incorporated by reference in its entirety). Five chemokines were differentially expressed between the tumor genotypes, with four of these (CCL3, CXCL1, CXCL2, and CCL4) being expressed at a lower levels in Braf$^{V600E}$/

Figure 11:
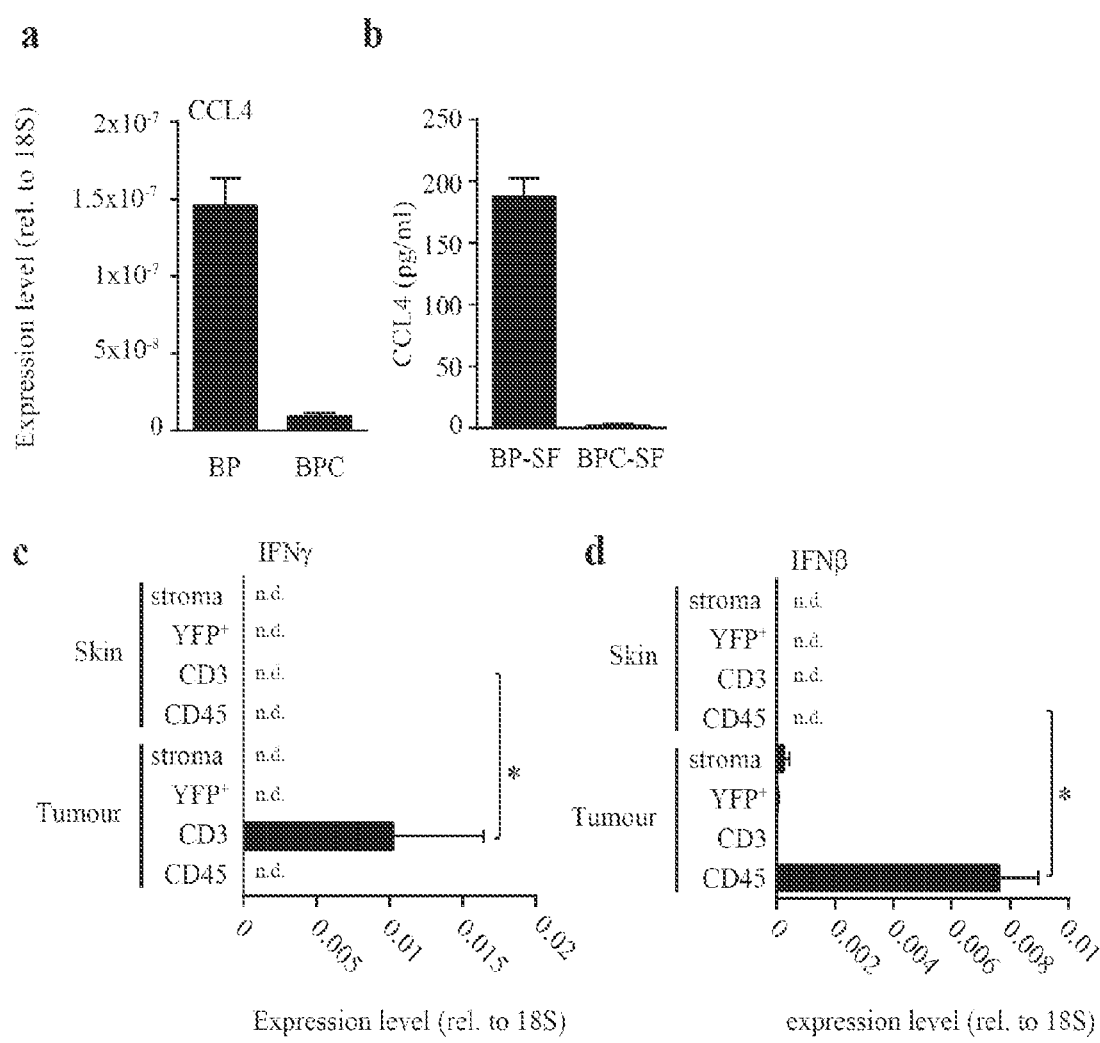
FIG. 11A-D. Chemokine expression patterns indicate that CCL4 expression from tumor cells is directly inhibited by active β-catenin-signalling. (a) Expression of CCL4 mRNA in established tumor cell lines BP and BPC. (b) Amount of secreted CCL4 in 48 h conditioned BP and BPC tumor cell supernatants, assessed by ELISA. (c-d) Control qRT-PCR for the experiment shown in FIG. 4e with (c) IFN-β expression and (d) IFN-Γ expression.

PTEN$^{-/-}$/CAT-STA tumors (FIG. 4a). Quantitative PCR confirmed the reduced expression levels in Braf$^{V600E}$/PTEN$^{-/-}$/CAT-STA tumors for all four chemokines, with the most significant differences detected in CCL4, CXCL1 and CXCL2 (FIG. 4b). To evaluate the tumor cell-intrinsic chemokine production in vivo Braf$^{V600E}$/PTEN$^{-/-}$ mice were crossed with YFP-reporter mice, which allowed identification of transformed, YFP$^+$ cells within the tumor mass. CD45-YFP$^+$ cells were sorted from early lesions 7 days after TAM application. Indeed, CCL4 transcripts were detected exclusively in the YPF$^+$ cell population from Braf$^{V600E}$/PTEN$^{-/-}$ mice, while control sorted YFP$^+$ cells from Braf$^{WT}$/PTEN$^{-/-}$ mice or YFP-cells showed no detectable expression of CCL4 (FIG. 4c). A similar expression pattern was observed for CXCL1, while CCL3 was found to be predominantly expressed by normal melanocytes (YFP$^+$ populations from both skin and tumor) and CXCL2 was only detected in YFP-stromal cells (FIG. 4c). As a sorting control, CD45$^+$CD3$^+$ and CD45$^+$CD3$^-$ cells were isolated and the expected patterns of IFN-β and IFN-γ expression was confirmed (FIG. 11c-d). To narrow a focus between CCL4 and CXCL1, the expression levels corresponding to chemokine receptors on DC (sorted CD45$^+$CD11c$^+$ cells) isolated from the tumor-microenvironment of Braf$^{V600E}$/PTEN$^{-/-}$/CAT-STA and Braf$_{V600E}$/PTEN$^{-/-}$ tumors was assessed. Significantly higher expression of CCR5 (the receptor for CCL4) was observed in DCs from Braf$^{V600E}$/PTEN$^{-/-}$ tumors compared to Braf$^{V600E}$/PTEN$_{-/-}$/CAT-STA tumors (FIG. 4d). CCR5 has previously been linked with the migratory capacity of CD8α$^+$DCs (Aliberti, J. et al. Nature immunology 1, 83-87 (2000); herein incorporated by reference in its entirety). Tumor cell lines generated from Braf$_{V600E}$/PTEN$^{-/-}$/CAT-STA and Braf$^{V600E}$/PTEN$^{-/-}$ mice exhibited increased expression of CCL4 by Braf$^{V600E}$/PTEN$^{-/-}$ (BP) tumor cells compared to Braf$^{V600E}$/PTEN$^{-/-}$/CAT-STA (BPC) tumor cells, which was also confirmed by ELISA at the level of protein secretion (FIG. 11a-b). To strengthen a functional role for CCL4 in the CD103$^+$ dermal-DC population, an in vitro migration assay in response to recombinant murine CCL4 was utilized (FIG. 4e). Indeed, skin-derived CD11c$^+$CD103$^+$DCs migrated in response to CCL4 to a comparable extent as lymph node-derived, CD11c$^+$CD8A$^+$DCs, which was eliminated upon pretreatment with pertussis toxin to block chemokine receptor activity. As an additional control, conditioned medium from generated tumor cell lines BP and BPC revealed DC migration only with supernatants from Braf$^{V600E}$/PTEN$^{-/-}$-derived tumor cells (FIG. 4e). Together, these results indicate that failed recruitment of CD103$^+$ DCs into the tumor-microenvironment of Braf$^{V600E}$/PTEN$^{-/-}$/CAT-STA tumors was due to defective production of the critical chemokine CCL4.

Figure 4:
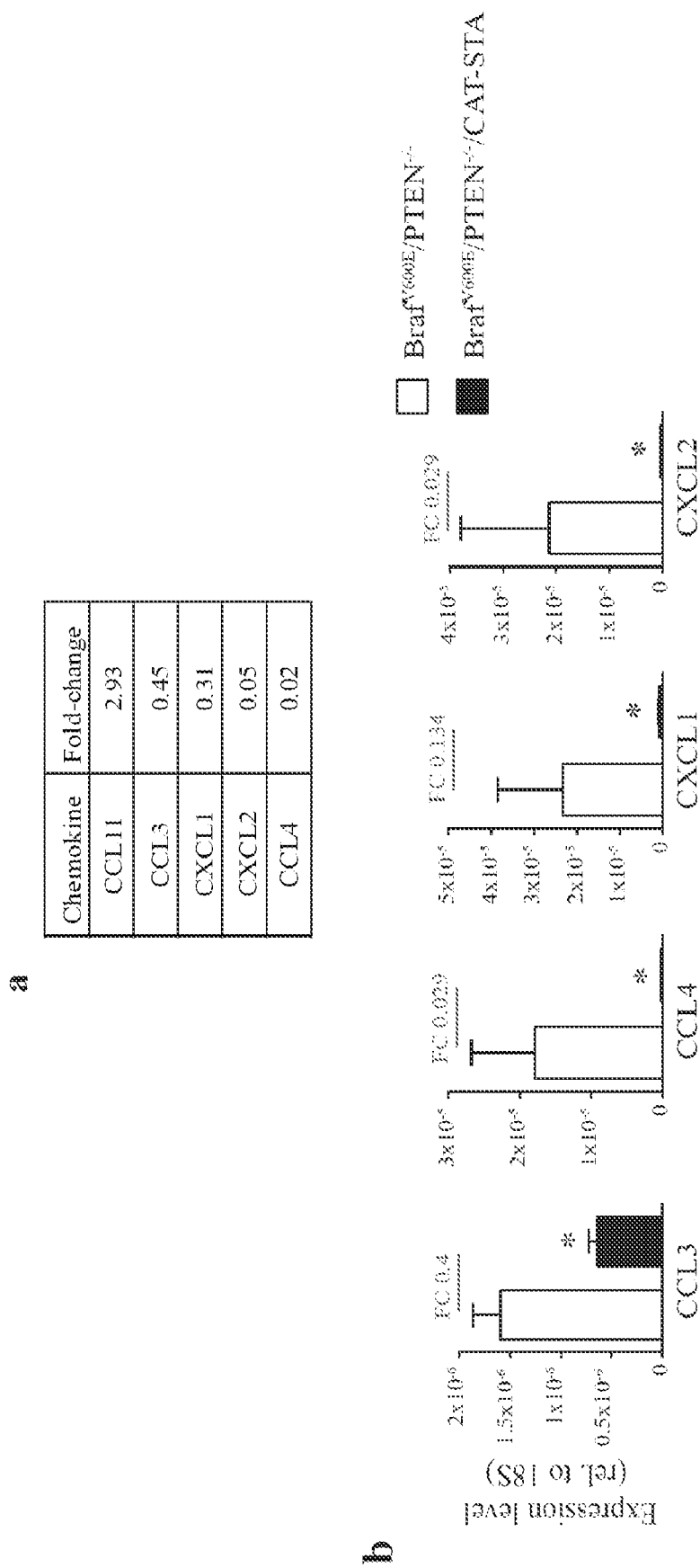
FIG. 4A-H. Active β-catenin-signalling within tumor cells suppresses the recruitment of CD103+ DCs. (a) Chemokine expression in $Braf^{V600E}/PTEN^{-/-}$ and $Braf^{V600E}/PTEN^{-/-}/CAT\text{-}STA$ tumors assessed via gene array analysis and (b) confirmatory qRT-PCR (fold change (FC) depicted on top). (c) Transcript levels of CCL3, CCL4, CXCL1 and CXCL2 assessed from YFP+ tumor cells and CD45− YFP− stroma cells from $Braf^{V600E}/PTEN^{-/-}/YFP^+$ tumors. (d) Expression level of CCR5 in sorted CD45+ CD11c+ DCs. (e) Migration assay of sorted DC subsets towards rmCCL4 or conditioned medium (SF). (f) ATF3 transcripts were assessed in tumor tissues. (g) ATF3-specific ChIP assay in BP and BPC cell lines for CCL4 and CCL2. (h) Amount of secreted CCL4 in 48 h conditioned siRNA-treated tumor cell BP and BPC supernatants, assessed by ELISA and ATF3 expression at the at the endpoint detected by qRT-PCR.
Figure 4:
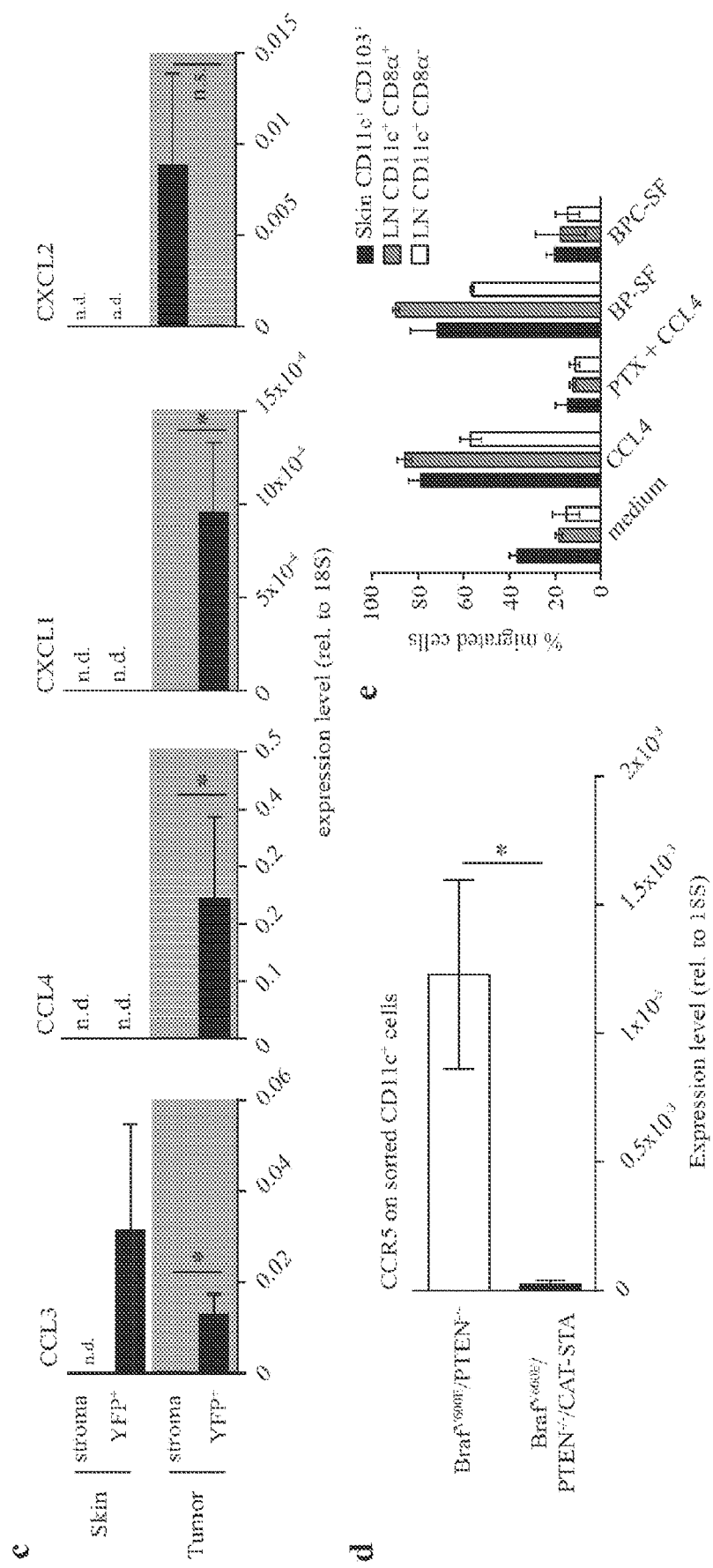
Figure 4:
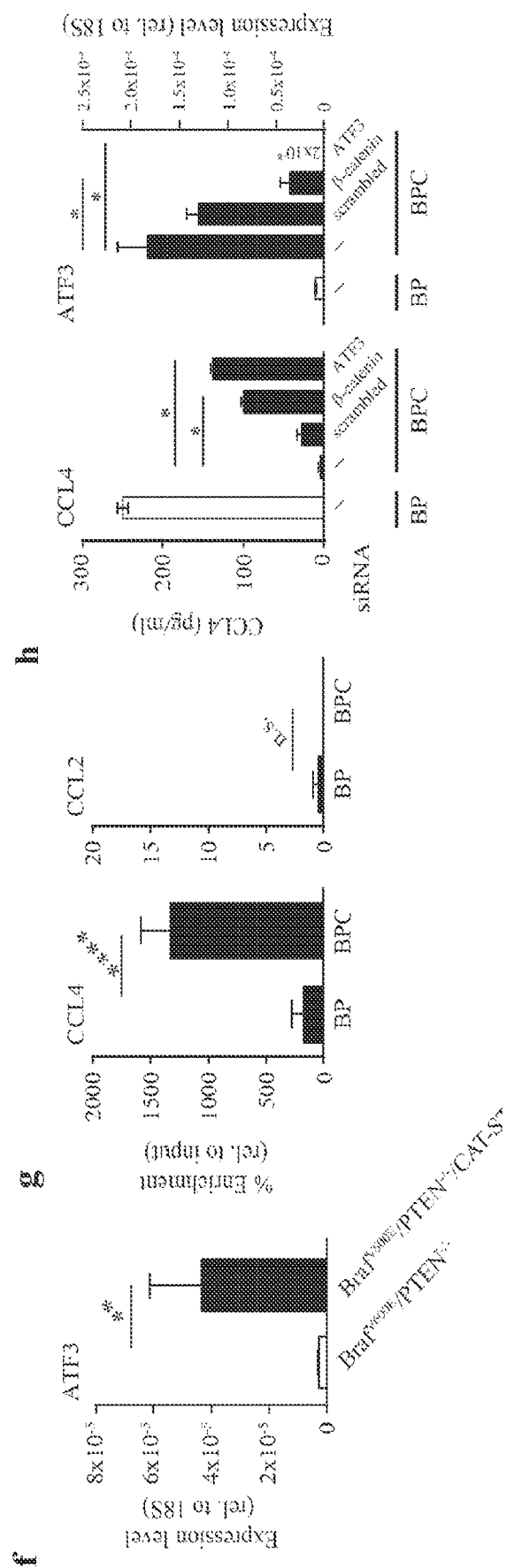
Figure 12:
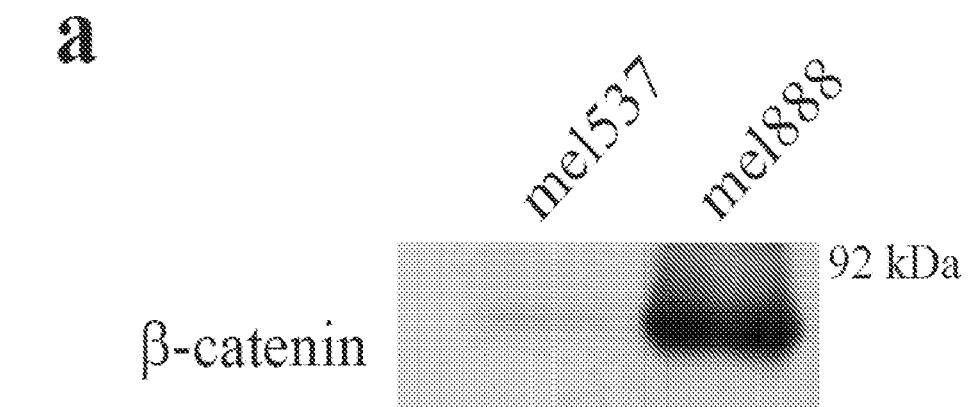
FIG. 12A-E. Active β-catenin signalling blocks CCL4 production in human melanoma cell lines. (a) Western blot on mel537 and mel888 showing stabilized β-catenin expression. (b) Expression level of human ATF3 and human CCL4 in mel537 and mel888. (c) Expression level of β-catenin target genes in mel537 and mel888. (d) ATF3-specific ChIP assay in mel537 and mel888 cell lines for the CCL4 gene locus. (e) CCL4 secretion (left) and ATF3 transcription levels (right) after siRNA mediated knock-down of β-catenin and ATF3 in mel537 and mel888 assessed by ELISA or qRT-PCR, respectively.
Figure 12:
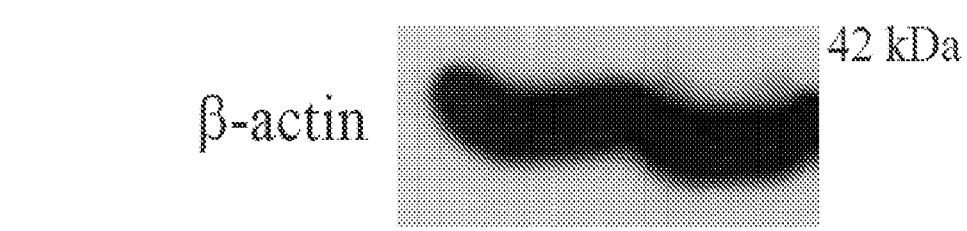
Figure 12:
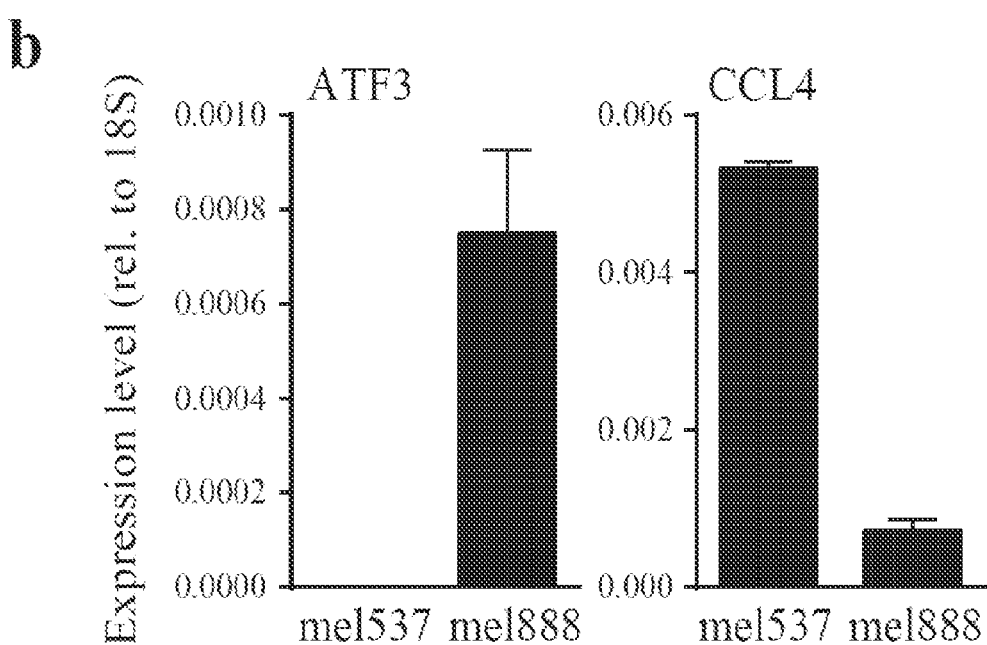
Figure 12:
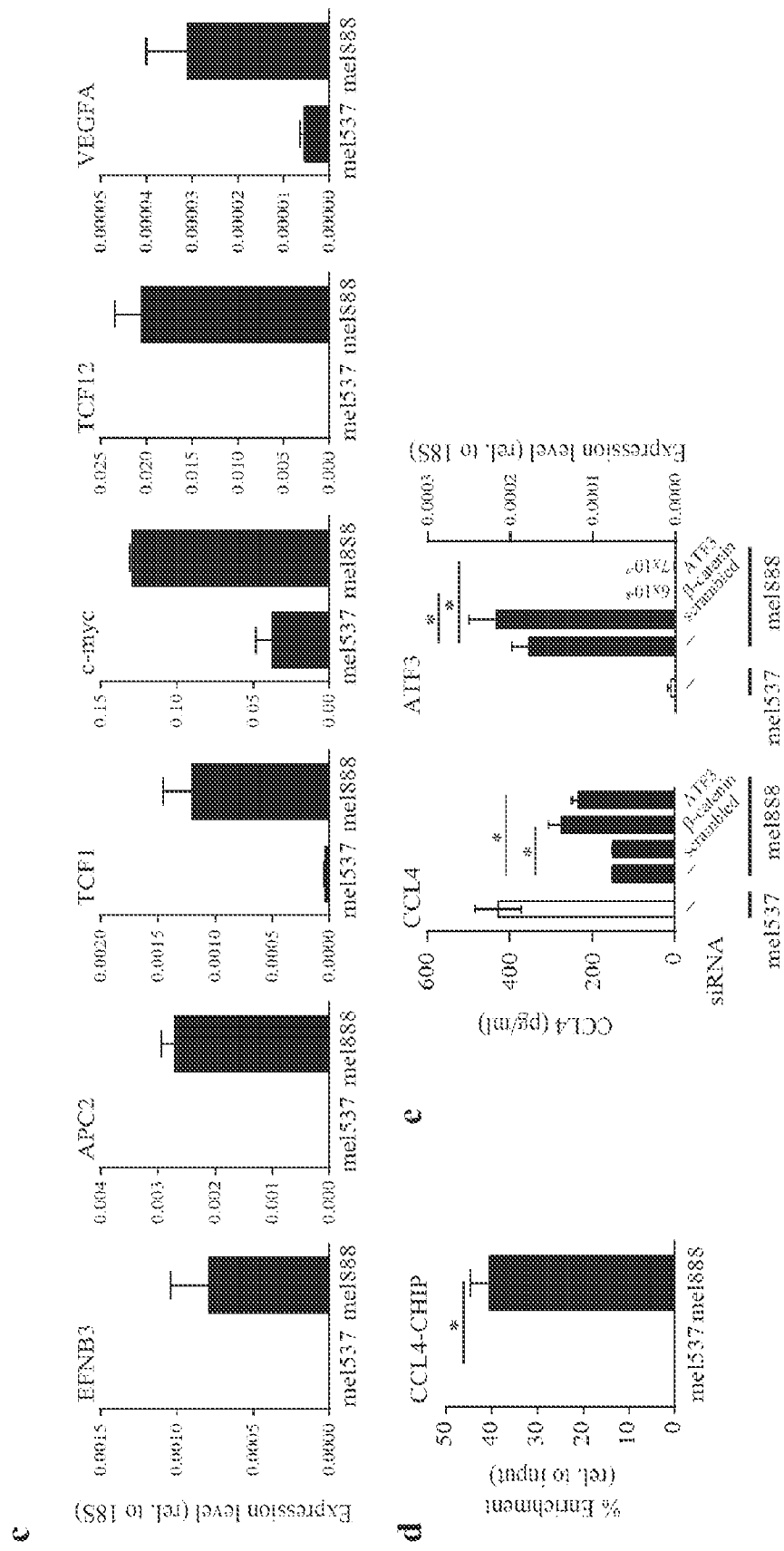

Experiments were conducted during development of embodiments described herein to determine a mechanism by which β-catenin activation prevents CCL4 gene expression (although the present invention is not limited to any particular mechanism of action and an understanding of the mechanism of action is not necessary to practice the present invention), since CCL4 has also been reported to be associated with a T cell infiltrate in human melanoma tumors (Salerno et al. Journal international du cancer 134, 563-574 (2014); Peng, W. et al. Cancer research 72, 5209-5218 (2012); herein incorporated by reference in their entireties). Previous reports had suggested that Wnt/β-catenin-signaling might induce expression of the transcriptional repressor ATF3 (Li, Y. et al. The Journal of biological chemistry 286, 32289-32299 (2011).; herein incorporated by reference in its entirety). In addition, ATF3 has been shown to suppress expression of CCL4$_{40}$. It was found that ATF3 was expressed at substantially higher levels in primary tumors as well as tumor cell lines from Braf$^{V600E}$/PTEN$^{-/-}$/CAT-STA mice (FIG. 4f). To assess whether a molecular association between ATF3 and the CCL4 gene could be observed, a ChIP-assay was performed using the established tumor cell lines. Indeed, a strong binding of ATF3 to the CCL4 promoter region was observed in the Braf$^{V600E}$/PTEN$^{-/-}$/CAT-STA tumor cell line while no binding was observed for CCL2, a chemokine lacking an ATF3 binding site (FIG. 4g). To assess a functional role for ATF3, siRNA mediated knock-down of ATF3 and also of β-catenin in BPC tumor cells resulted in restored CCL4 production (FIG.4 h, knockdown of β-catenin was additionally controlled by western blot). To examine this relationship in human melanoma, two melanoma cell lines were analyzed, mel537 and mel888, which show low or high β-catenin expression, respectively (FIGS. 12a and 12c). Consistent with the observations in the murine cell lines, increased ATF3 and decreased CCL4 expression and secretion were observed in the β-catenin positive mel888 compared to mel537 (FIGS. 12b and 12e). Furthermore, increased binding of ATF3 to the CCL4 promotor region in the β-catenin positive mel888 cell line compared to mel537 was observed (FIG. 12d). siRNA-mediated knock-down experiments targeting ATF3 and β-catenin in mel888 cells resulted in a significant restoration of the CCL4 expression and secretion, indicating a key inhibitory role of both factors (FIG. 12e).

It was additionally investigated whether decreased presence of Batf3-lineage DCs in T cell signature-low tumors was associated with active β-catenin signaling in human melanoma metastases. A Pearson correlation analysis using the TCGA data set for expression of THBD (CD141, a marker for human Batf3-lineage DCs p<0.0001), Batf3 (p=0.0336), and IRF8 (p<

Figure 13:
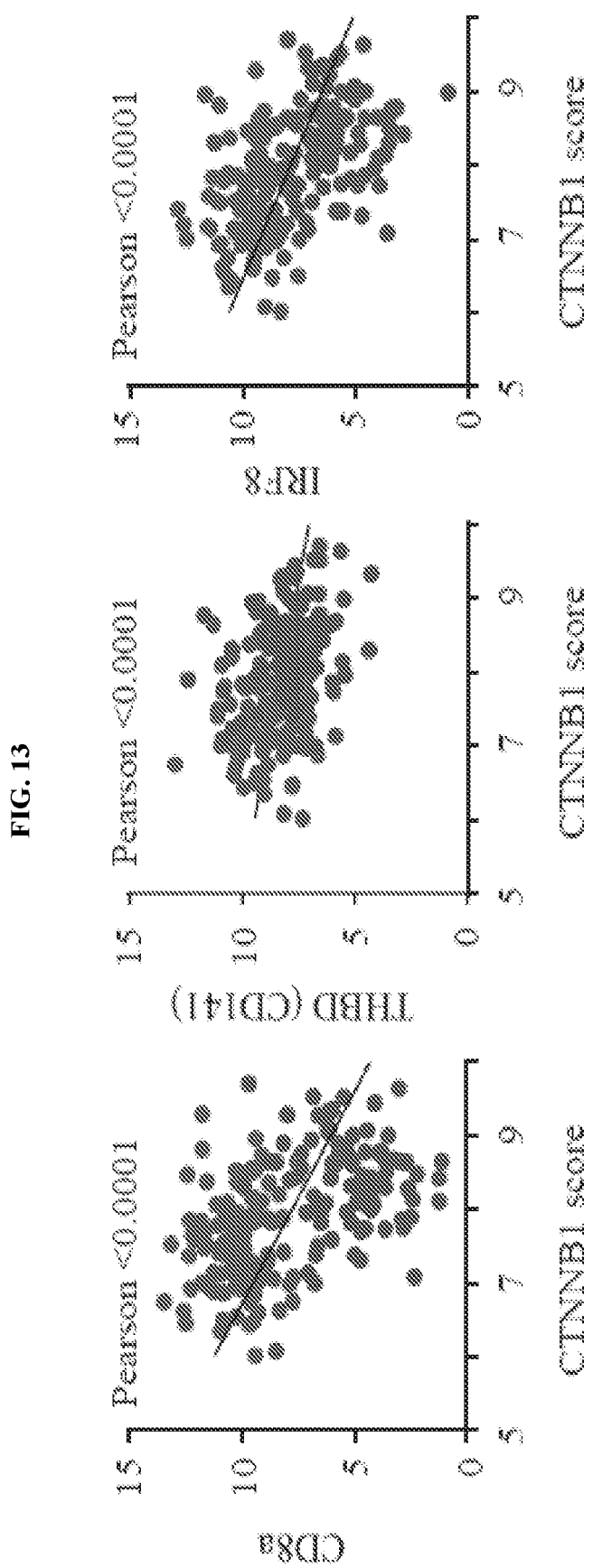
FIG. 13. β-catenin target gene expression correlates inversely with markers for human Batf3-lineage dendritic cells and T cells. Pearson-correlation of CTNNB1 score with CD8α ($R^2$=0.214), THBD ($R^2$=0.109) and IRF8 ($R^2$=0.2374).
Figure 14:
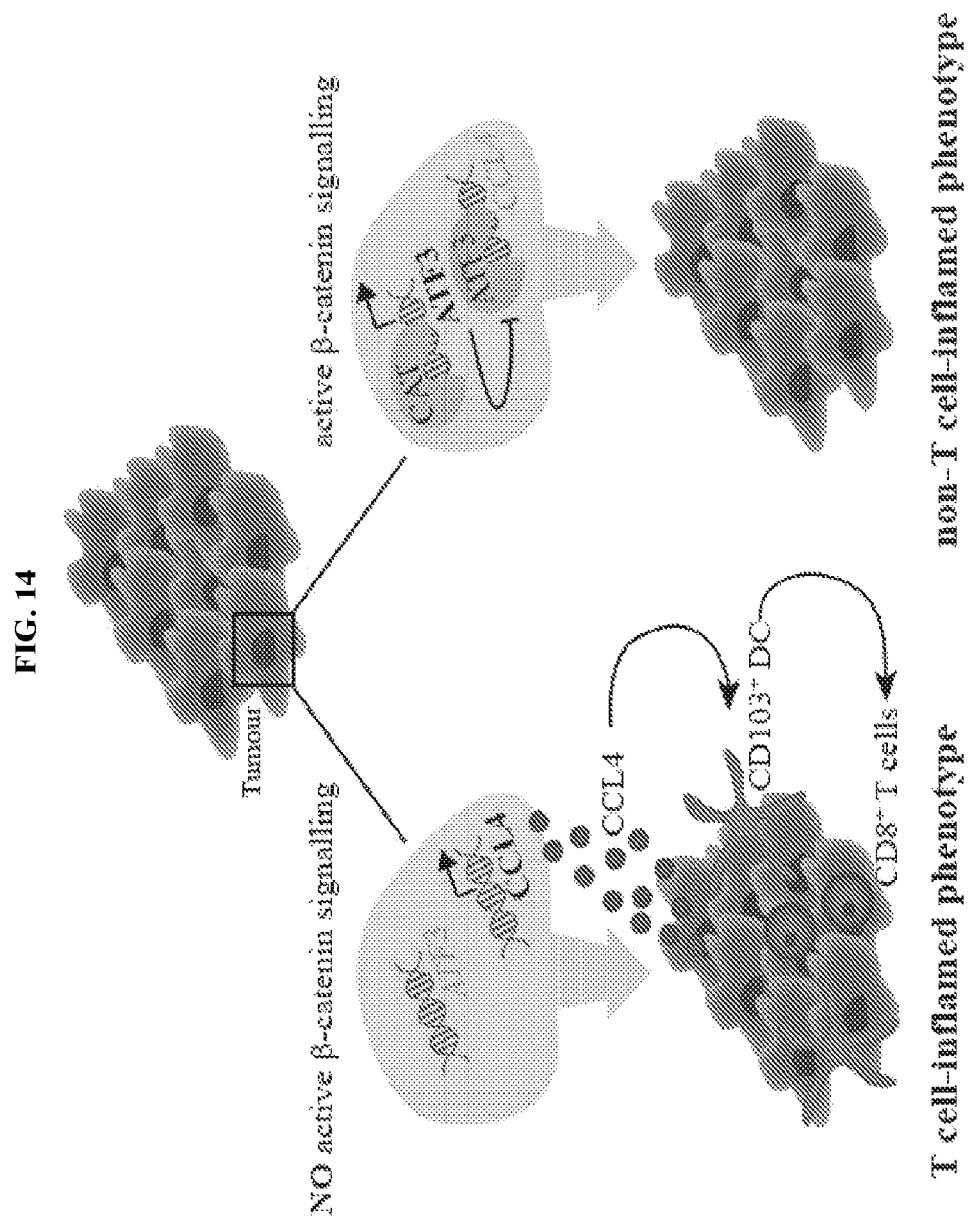
FIG. 14. Graphical summary. Left: tumor without active β-catenin signalling in which ATF3 transcription is not induced and thus CCL4 is transcribed and secreted. Downstream CD103$^+$ DCs are attracted and subsequent activation of CD8$^+$ T cells is enabled. Right: tumor with active β-catenin signalling, which leads to induction of ATF3 transcription, which in turn leads, amongst others effects, to suppression of CCL4 transcription. This leads to an active escape from the anti-tumor immune response since DC recruitment is insufficient.

0.0001) revealed a negative association with the CTNNB1 score (FIG. 13). Furthermore, CCL4 had already been observed to positively correlate with T cell transcripts in T cell-inflamed tumors. Taken together, experiments conducted during development of embodiments described herein demonstrate that β-catenin activation within melanoma cells results in decreased CCL4 gene expression partly mediated through ATF3-dependent transcriptional repression (FIG.14).

Figure 5:
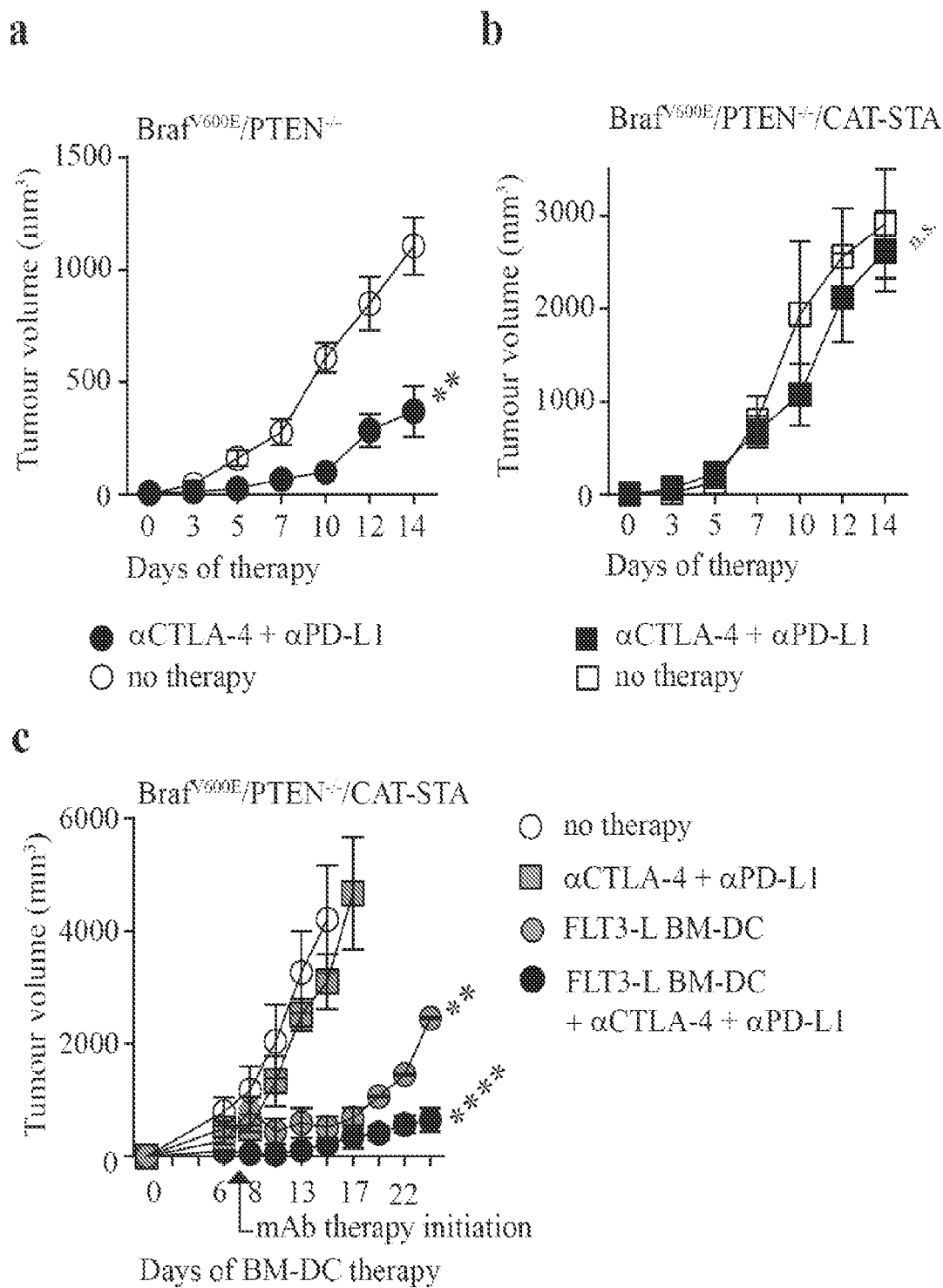
FIG. 5A-B. Reconstitution with Flt3 ligand DCs reverses resistance towards immunotherapy. (a-b) Tumor growth in $Braf^{V600E}/PTEN^{-/-}$ (a) and $Braf^{V600E}/PTEN^{-/-}/CAT\text{-}STA$ (b) mice untreated or treated with αCTLA-4 and αPD-L1 therapy. (c) Tumor growth of $Braf^{V600E}/PTEN^{-/-}/CAT\text{-}STA$ tumor-bearing mice untreated, αCTLA-4 and αPD-L1 therapy, intratumoral Flt3 ligand-DC injections, or combination therapy.

To explore therapeutic relevance of the lack of T cell-infiltration in this genetic tumor model, Braf$^{V600E}$/PTEN$^{-/-}$ and Braf$^{V600E}$/PTEN$^{-/-}$/CAT-STA mice were treated with a combination of αCTLA-4 and αPD-L1 mAbs, 3 weeks after TAM application (Wolchok, J. D. et al. The New England journal of medicine 369, 122-133 (2013); Spranger, S. et al. Journal of ImmunoTherapy of Cancer 2 (2014); herein incorporated by reference in their entireties). While treatment of Braf$^{V600E}$/PTEN$^{-/-}$ mice resulted in a significant delay in tumor outgrowth, no therapeutic effect was detected in Braf$^{V600E}$/PTEN$^{-/-}$/CAT-STA mice (FIG. 5a-b) To evaluate whether restoration of intratumoral DCs could restore immunotherapy responsiveness, Flt3 ligand induced bone marrow DCs, activated with polyI:C, were injected intratumorally into Braf$^{V600E}$/PTEN$^{-/-}$/CAT-STA tumors. Indeed, introduction of DCs tumors showed a partial therapeutic effect alone, which was improved significantly with the additional administration of αCTLA-4+αPD-L1 mAbs (FIG. 5c).

Experiments were conducted during development of embodiments described herein demonstrate that melanoma cell-intrinsic activation of the oncogenic β-catenin-signaling pathway result in exclusion of the host immune response, including absence of a T cell infiltrate within the tumor-microenvironment. Experiments indicate that inhibitors of this β-catenin-signaling are immune-potentiating. Experiments indicate that the T cell-inflamed tumor microenvironment phenotype is predictive of clinical response to multiple immune-based therapies, including effective cancer vaccines, anti-CTLA-4 mAb, anti-PD-1 and anti-PD-L1 mAbs, TIL-based adoptive T cell transfer, and high dose IL-2. Immune escape among this subset appears to be a consequence of dominant effects of negative regulatory pathways within the tumor-microenvironment, arguing that clinical activity of immunotherapeutic interventions is tipping the balance in favor of an ongoing attempt at immune-mediated tumor regression by the host. Experiments conducted during development of embodiments described herein demonstrate that tumor intrinsic β-catenin activation represents a mechanism of primary resistance to these therapies.

Example 3

Experimental Methods (Results in Example 4)

Mice and Cell Lines.

The following mouse strains were used to generate the mouse models: Tyr:Cre-ER, loxP-Braf$^{V600E}$, loxP-PTEN, loxP-CAT-STA, loxP-rosa-SIY and loxP-rosa-YFP (Jackson Laboratories, strain 006148) reporter. Genotyping was performed. Additionally, TCR-Tg 2C mice were maintained as T cell donors and RAGN12-F were obtained as hosts for tumor cell lines.

All animal procedures were approved by the IACUC Committee of the University of Chicago. For vaccination 1×10$^6$ MC57-SIY cells were injected subcutaneously on the flank of the GEMs (6-10 weeks of age).

Autochthonous Tumor Induction, Tissue Harvest and Generation of Cell Line.

For induction of the autochthonous tumor mice, which rejected the MC57-SIY tumor, were shaved on the back and 5 µl of 4-OH-Tamixifen (Sigma) at a concentration of 10 µg/ml (dissolved in acetone) was applied, two months after complete rejection. As controls, mice of similar age were housed for the entire duration of the experiment before treated with 4-OH-tamoxifen. Subsequently, mice were screened weekly for tumor induction. For tumor outgrowth experiments, mice were treated at the lower back with 4-OH-Tamoxifen at day 0. Following day 24, tumor masses were measured by assessing length, width and height of major tumor mass using a digital caliper. Measuring the height was a critical parameter to assess tumor growth, since width and length were mainly influenced given by the spread of the TAM solution. Tumor volume was calculated: $T^V=T^L*T^W*T^H$, since the tumor shape was rectangular and flat, rather than spherical. The maximum tumor size was reached when the tumor mass reached approximately 10% of the body weight. At the indicated experimental endpoint, tumor tissue was harvested and single cell a suspension was prepared. For tumor cell line generation, a single cell suspension of the tumor tissue was generated and used in its entirety for subcutaneous injections into Rag-KO mice (RAGN12-F; Taconic). Following tumor outgrowth, the tumor tissue was harvested and reinjection into Rag-KO mice and adapted to cell culture using DMEM (Gibco) with 10% FCS (Atlanta Biologics), 1×NEAA (Gibco) and 1×MOPS (Sigma). Prior to MHC-class-I staining cells were cultured for 24 h in the presence of 100 µg/ml IFN-γ (Biolegend).

IFN-γ ELISpot.

Splenocytes from naïve, tumor-challenged non-treated or treated mice were harvested on day 7 or day 14 after tumor inoculation. Single cell suspensions were prepared and 1×10$^6$ splenocytes were assayed per well. Cells were either left un-stimulated or stimulated with 160 nM SIY-peptide (SIYRYYGL) (SEQ ID NO: 7) or PMA 100 ng/ml and Ionomycin 1 µg/ml as positive control. After a 24 h culture period, detection of INF-γ production was performed according to manufacturer's instructions.

Flow Cytometry.

For flow cytometric analysis, washed cells were resuspended in staining buffer (PBS with 10% FCS and 0.5 M EDTA (Ambion). Cells were incubated with live/dead staining dye (Invitrogen, wavelength 450) and Fc Block (clone 93; Biolegend) for 20 min on ice. Subsequently, specific antibodies were added (Table 1) and staining was continued for 40 min on ice. After a washing step, cells were either analyzed directly or fixed with 4% PFA (BD) solution for 30 min and stored in a 1% PFA solution until analysis. Staining of SIY-specific cells was performed using the SIYRYYGL-pentamer (Proimmune) (SEQ ID NO: 7), conjugated with Phycoerythrin (PE), or as a non-specific control with the SIINFEKL-pentamer (SEQ ID NO: 8). For staining, pentamers were diluted 1:50 in PBS+10% FCS and incubated for 20 minutes at room temperature (RT). Following a washing step, cells were stained with specific antibodies for 30 minutes on ice prior to fixation in 4% PFA. For staining of TCRTg 2C T cells a TCR specific-biotinylated mAb (1B2 clone) was obtained from the University of Chicago Monoclonal Core Facility. Subsequent to live/dead staining, TCR-specific mAb was added for 15 min on ice at a 1:100 dilution alone with surface Abs targeting other antigens added in for an additional 25 minutes thereafter. After a washing step, a 1:500 dilution of Streptavidin APC was added and incubated on ice for 20 minutes before cells were fixed in 4% PFA and stored in 1% PFA solution. Flow cytometry sample acquisition was performed on a LSR2B (BD), and analysis was performed using FlowJo software (TreeStar). For cell sorting, staining protocols were carried out similarly under sterile conditions.

TABLE 1

List of antibodies.

| Antigen | Fluorophore | clone | dilution | vendor |
|---|---|---|---|---|
| CD19 | PB | eBio1D3 | 1/200 | ebioscience |
| CD3 | AX700 | 17A2 | 1/200 | eBio |
| CD3e | Ef450 | 145-2C11 | 1/200 | ebioscience |
| CD4 | PerCP-Cy5.5 | RM4-5 | 1/200 | BioLeg |
| CD45 | AX488 | 30-F11 | 1/200 | BioLeg |
| CD8a | APC-CY7 | 53-6.7 | 1/200 | BioLeg |
| CD8a | PE | 53-6.7 | 1/200 | PharMingen |
| CD8a | PerCP | 53-6.7 | 1/200 | BD |
| FC BLOCK | | 93 | 1/200 | BioLeg |
| Fixable Viability | eFlour 450 | Amine-reactive | 1/200 | eBio |
| Streptavidin | APC | | 1/500 | BD |

Functional Antigen-Detection Assay.

Established cell lines from BP-SIY, BPC-SIY and MC57-SIY immunized mice were co-cultured with CFSE-labeled 2C TCR-transgenic T cells for 72 hours at a ratio of 1 tumor cell (4000 cells) to 10 T cells (40000 cells). Therefore, CD8$^+$ T cells from 2C donor mice were isolated using the Miltenyi CD8$^+$ enrichment Kit II for untouched CD8$^+$ T cell isolation. After isolation cells were stained with 1 µm CFSE-solution (eBioscience) for 8 min at 37° C. For positive control tumor cells were pulsed with 100 mM SIY peptide for 1 h prior to co-culture. Additionally, BP and BPC tumor cells derived from Braf$^{V600E}$/PTEN$^{-/-}$ and Braf$^{V600E}$/PTEN$^{-/-}$/CAT-STA mice, respectively, were transduced with a retroviral vector containing a SIY-GFP fusion protein facilitating expression of the antigen as previously described. Following co-culture cells were harvested, stained with a live/dead dye as well as for CD3 and CD8 and subsequently analyzed for dilution of CFSE.

Molecular Antigen-Detection Assay.

To assay for the presence of antigen within tumor cells, RNA was isolated and cDNA generated. PCR was performed using primers specific for the luciferase gene in case of BP-SIY and BPC-SIY derived cell lines or GFP for in vitro transduced cell lines with amplicons of 183 base pairs and 182 base pairs, respectively. PCR on 18S was used for quality control of the produced cDNA. Primer sequences: LUC-SIY &&& 5'agcgaaggttgtggatctgg (SEQ ID NO: 1) and 3'tgttcgtcttcgtcccagt (SEQ ID NO: 2); GFP-SIY 5'gtgaagttcgagggcgaca (SEQ ID NO: 3) and 3'tcgatgttgtggcggatctt (SEQ ID NO: 4); 18S 5'cggctaccacatccaaggaa (SEQ ID NO: 5) and 3'gctggaattaccgcggct (SEQ ID NO: 6).

Adoptive T Cell Transfer.

For adoptive T cell transfer experiments, tumor development was induced and transfer of 1×10$^6$ or 10×10$^6$ T cells was performed when tumors reached 600-1000 mm$^3$ (approx. 5-6 weeks after induction). Transferred T cells were isolated from gender-matched 2C donor mice using the Miltenyi CD8$^+$ enrichment Kit II for untouched CD8$^+$ T cell isolation. After isolation, cells were activated for three days through plate-bound CD3 (0.2 µg/ml; 145-2C11 clone; Biolegend) and CD28 (0.5 µg/ml; 37.51 clone; BD) antibodies. Following activation, T cells were stained with 1 µm CFSE-solution (eBioscience) for 8 min at 37° C. before intravenous injection. Tumor tissue, tumor-draining LNs, and spleen were harvested 3 days following adoptive transfer of T cells and used for flow cytometric analysis. This short time frame was chosen to avoid the reported leakiness of the SIY-transgene that has been associated with partial T cell activation within the spleen and to assure no additional proliferation would take place. For tumor tissues, the entirety of each sample was acquired and total number of CD3$^+$CD8$^+$ T cells and transferred 2C cells was assessed. The percentage 2C cells was calculated as [(100/CD3$^+$/CD8$^+$ T cells)*2C] and also the number of 2C cells per gram tumor. For therapeutic adoptive transfer experiments, T cell medium was supplemented with huIL-2, muIL-7 and muIL-15 at 5 ng/ml final concentration (Peprotech) and cells were cultured for 7 days prior to transfer. T cells for adoptive transfer prior to intravital imaging were cultured only in the presence of huIL-2 for 5 days and labeled with CellTracker Deep Red (ThermoFisher) prior to adoptive transfer.

Intra-Vital Imaging and Analysis.

Tumors were induced via application of 4-OH-tamoxifen on the flank of the mice. 21 days post tumor induction, effector T cells labelled with cell tracker deep red (Life technologies), were adoptively transferred through intravenous injection. 24 h post adoptive transfer implanted window chambers onto the induced tumor moles and initiated imaging 24 h later. For imaging, mice were anesthetized using isoflurane inhalation. The window was fastened to the main stage of the microscope using a custom-made holder. A motorized microscope XY scanning stage and Leica LAS-AF software allowed recording of individual 3-dimensional positions per field-of-view and returning to them later with high precision (stated accuracy +/− 3 µm; reproducibility <1.0 µm). Confocal images were captured with a Leica SP5 II TCS Tandem scanner spectral confocal with 4× and 25×/0.45 LWD IR objectives from Olympus. The optical penetration of tissue ranged between 90-150 µm with the average of 120-150 µm. The 488 nm and 633 nm excitation laser lines were used. All images were acquired with a 4.12 sec exposure time. Analysis was done using ImageJ (NIH) and MtrackJ plug-in software (E. Meijering, O. Dzyubachyk, I. Smal Methods for Cell and Particle Tracking Methods in Enzymology, vol. 504, February 2012, pp. 183-200; incorporated by reference in its entirety). MtrackJ software enabled assessment of velocity as well as displacement for each of the analyzed T cells. Further spider plots were obtained from single time point analysis assessed through this software. Net-displacement was calculated as $\sqrt{[(X_{end})^2+(Y_{end})^2]}-\sqrt{[(X_{start})^2+(Y_{start})^2]}$. Distance between T cell (center) and tumor cell (nearest edge) was assessed using ImageJ ROI manager.

Example 4

Experimental Results (Methods in Example 3)

Figure 15:
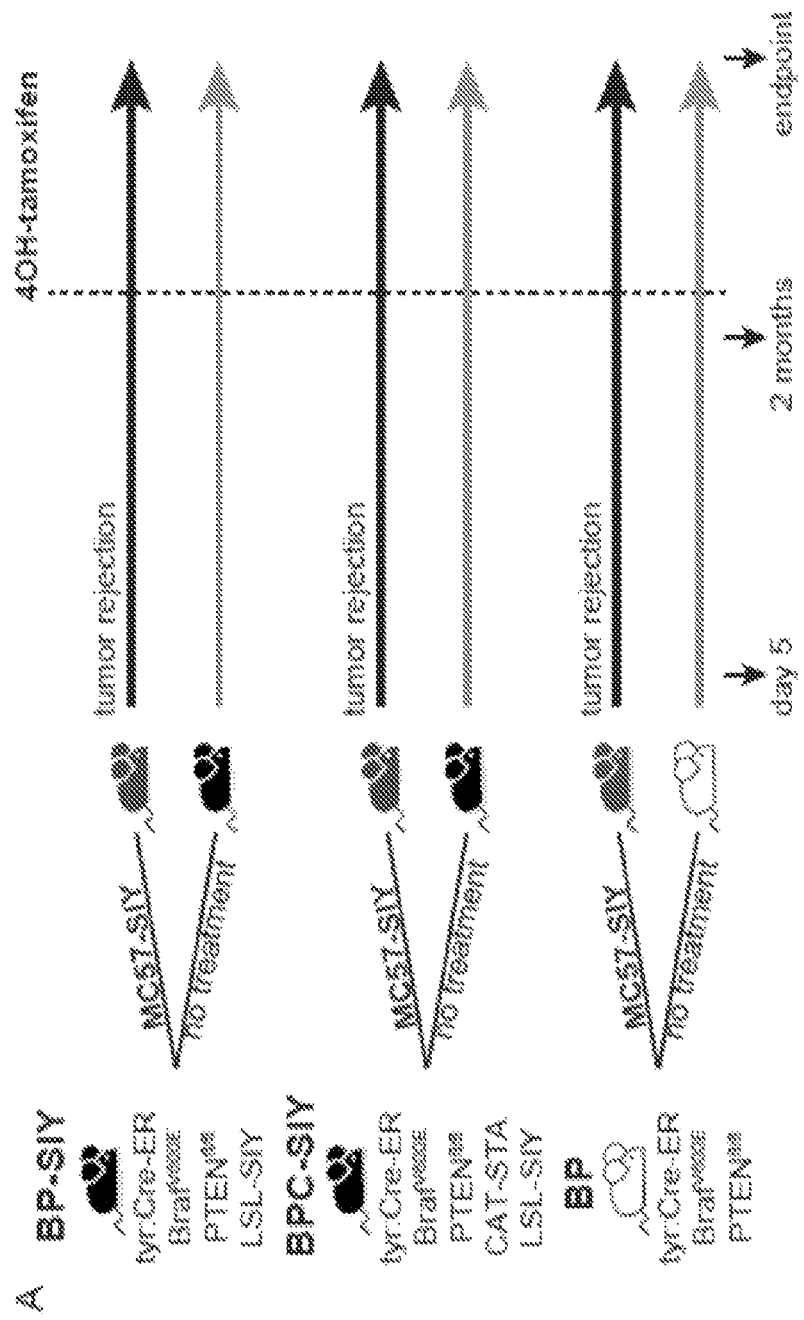
FIG. 15. BPC-SIY tumor lack T cell infiltration compared to BP-SIY mice. (A) Schematic of experimental procedure to induce immunological memory against tumor-derived SIY. All mice were housed for equal times and were 6-8 weeks at the beginning of the experiment. (B) BP-SIY and BPC-SIY tumors were analyzed for the degree of T cell infiltration 6-8 weeks after tumor induction. Depicted is amount of CD3$^+$ infiltrated T cells per gram of tumor. (C) SIY-specific immune response was measured by IFN-γ ELISpot in BP-SIY and BPC-SIY mice inoculated with MC57. SIY 5 day or 60 days prior to the assay. As a control, littermates not injected with MC57. SIY were used.
Figure 15:
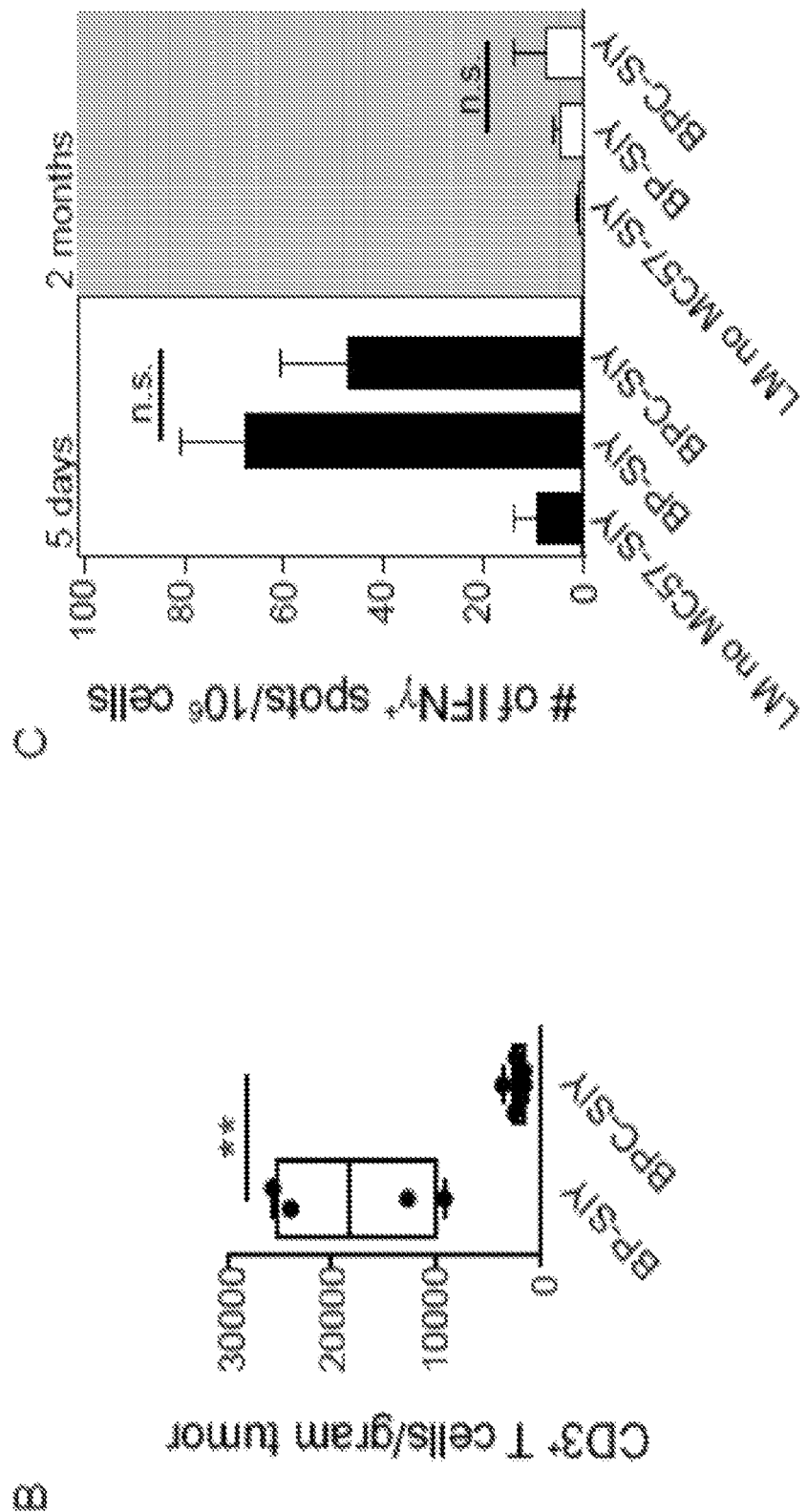
Figure 16:
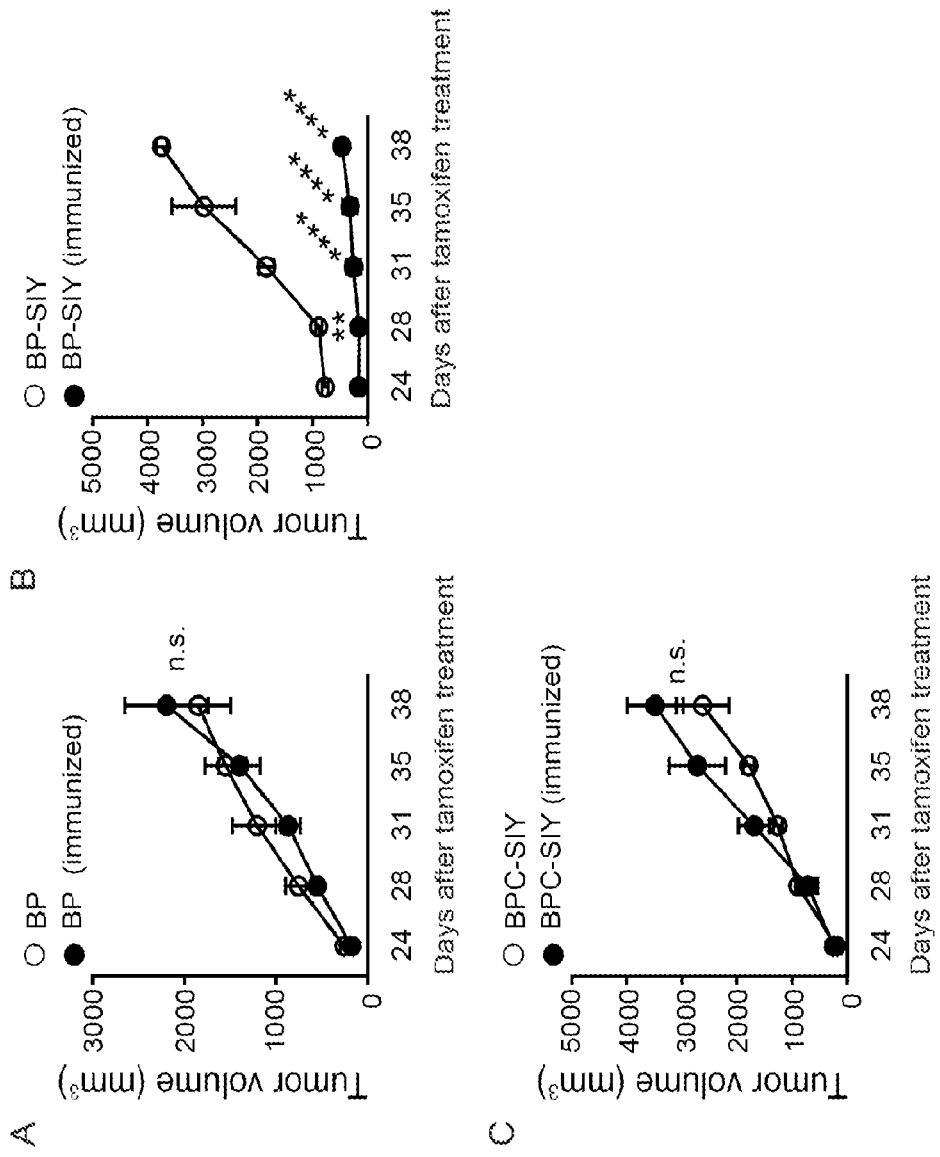
FIG. 16. Pre-existing immunological memory increases tumor control in BP-SIY mice but not in BPC-SIY mice in an antigen-dependent manner. Mice were treated with 4-OH-tamoxifen 2 months after complete rejection of the primary MC57-SIY tumor. Following day 24-post tamoxifen-treatment tumor growth of the autochthonous tumor was assessed until the experimental endpoint was reached. (A) Depicts mice of the BP strain (B) of the BP-SIY strain and (C) of the BPC-SIY strain with filled symbols representing MC57-SIY immunized mice and open symbols naïve mice.

Tumor Cell-Intrinsic Activation of β-Catenin Allows Autochthonous Tumors to Escape from a Potent Antigen-Specific Memory Response In order to induce a spontaneous antigen-specific antitumor immune response against a primary T cell-inflamed tumor, the sarcoma cell line MC57, genetically engineered to express the model antigen SIY (SIYRYYGL (SEQ ID NO: 7)), was used. The cell line, on C57/BL6 background, is spontaneously rejected when implanted into immune-competent mice within ten days post implantation. Genetically engineered mice harboring the following genotypes were used as hosts: Tyr:CreER, Braf-LSL-V600E, PTEN FL/FL (BP); Tyr:CreER, Braf-LSL-V600E, PTEN FL/FL, R26-LSL-SIY-Luc (BP-SIY) and Tyr:CreER, Braf-LSL-V600E, PTEN FL/FL, LSL-CAT-STA, R26-LSL-SIY-Luc (BPC-SIY). Un-injected, age and gender-matched, littermate controls were used. Following complete tumor rejection, mice were housed for an additional two months to allow the establishment of a memory response, before 4OH-tamoxifen was applied topically to induce Cre-activation and thereby the development of autochthonous tumors (FIG. 15A). As a control, it was confirmed that the observation that BP-SIY tumors contain CD3$^+$ T cells, while BPC-SIY positive tumors lack the infiltration of endogenous T cells in unperturbed non-immunized mice (FIG. 15B). Next, it was assessed if both BP-SIY as well as BPC-SIY mice were capable to reject MC57-SIY tumor cells as well as if the induced acute as well as memory immune responses were comparable. Indeed, all mice tested (BP-SIY 17/17, BPC-SIY 17/17) showed complete rejection of the transplanted tumor and the detected acute and memory immune responses against the SIY-peptide were similar (FIG. 15C). To assess if tumor cell-intrinsic β-catenin signaling can mediated resistance against an existing immune response, autochthonous tumors were induced on naïve or MC57-SIY-immunized BP-SIY, BPC-SIY and BP mice. BP mice served as a control for an antigen-specific memory response since no tumor-associated antigens are shared between BP tumors and MC57-SIY. Tumor growth was assessed once the tumors were palpable. As expected, a delay in tumor growth was not observed between naïve and immunized BP mice since the secondary tumor lacks the dominant antigen (SIY) (FIG. 16A). In contrast, when comparing the tumor growth of naïve and immunized BP-SIY a strong and significant delay in tumor outgrowth was observed in the presence on a pre-existing SIY-specific memory response (FIG. 16B). This result indicates that the existing memory response against the SIY peptide is sufficient to control tumor growth in the context of a T cell-inflamed tumor microenvironment. Comparing immunized and naïve tumor bearing BPC-SIY mice indicates that the existing immunity is not protective against tumor growth of β-catenin-positive tumors (FIG. 16C). These data indicate that activation of tumor cell-intrinsic β-catenin signaling prevents immune surveillance and thereby mediated delay in tumor growth.

Figure 17:
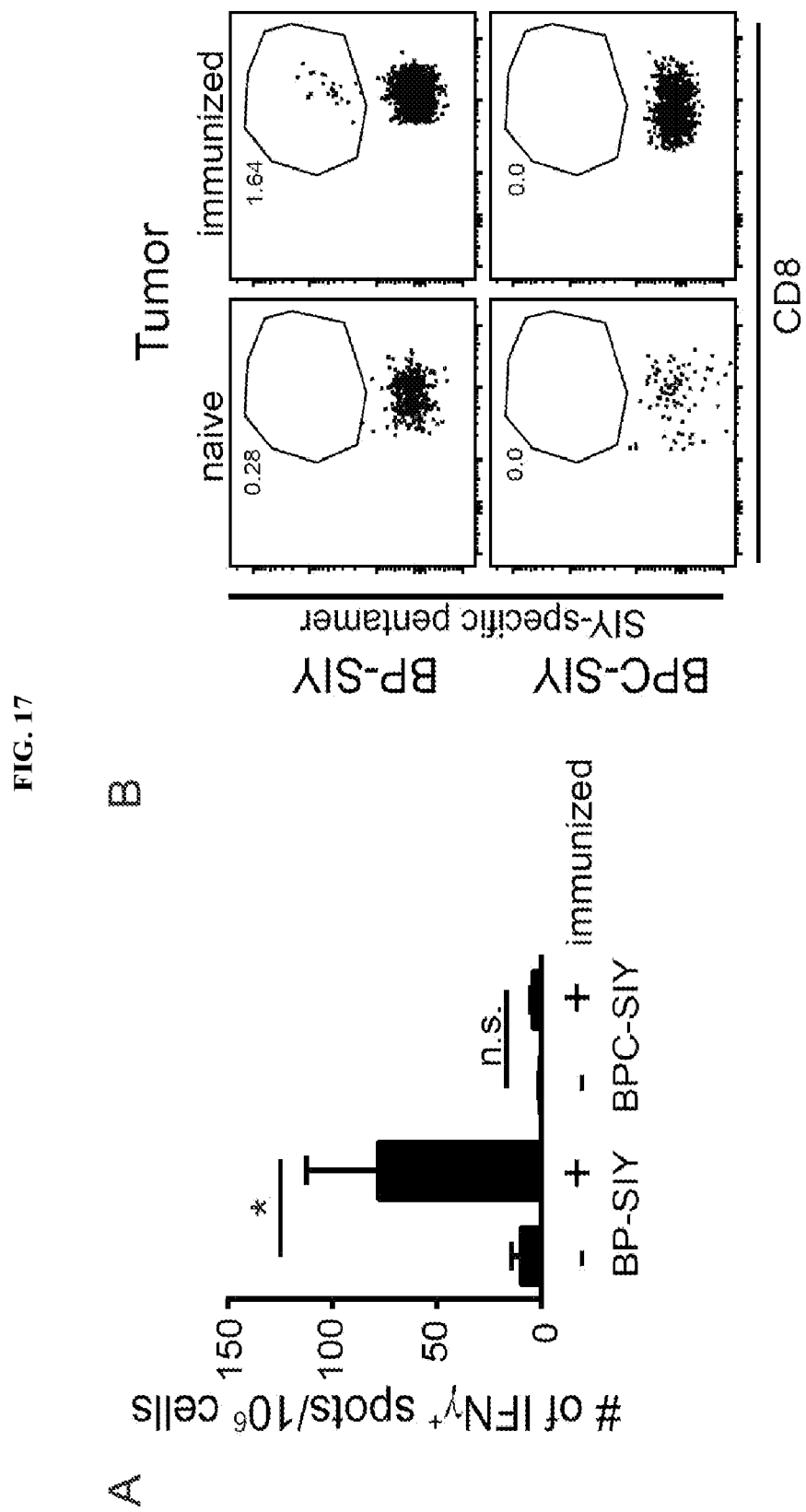
FIG. 17. Increased tumor control in BP-SIY tumor is mediated through reactivation peripheral anti-tumor memory response and increased infiltration of antigen specific T cells into the tumor microenvironment. (A) Depicted is an IFN-γ ELISpot assessing the number of SIY-specific IFN-γ production by splenocytes isolated at the end point of the experiment shown in FIG. 16. (B-D) Shows the amount of antigen-specific cells within the tumor microenvironment assessed though SIY-specific pentamer staining. The analyzed tumors were from immunized and non-immunized BP-SIY and BPC-SIY tumors at the endpoint of the experiment with (B) depicting a representative example of the pentamer staining, (C) showing the percent within the CD8 T cell compartment and (D) the absolute number of SIY-reactive T cells per gram tumor.
Figure 17:
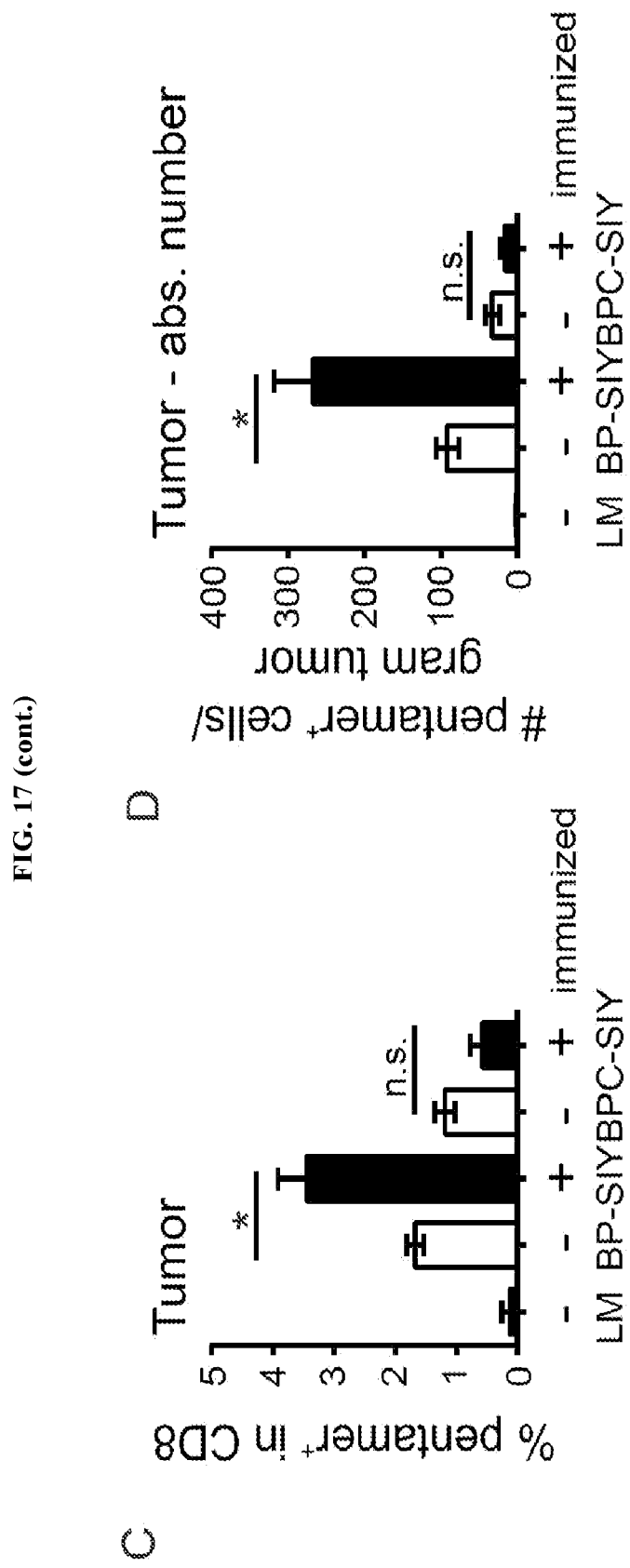
Figure 18:
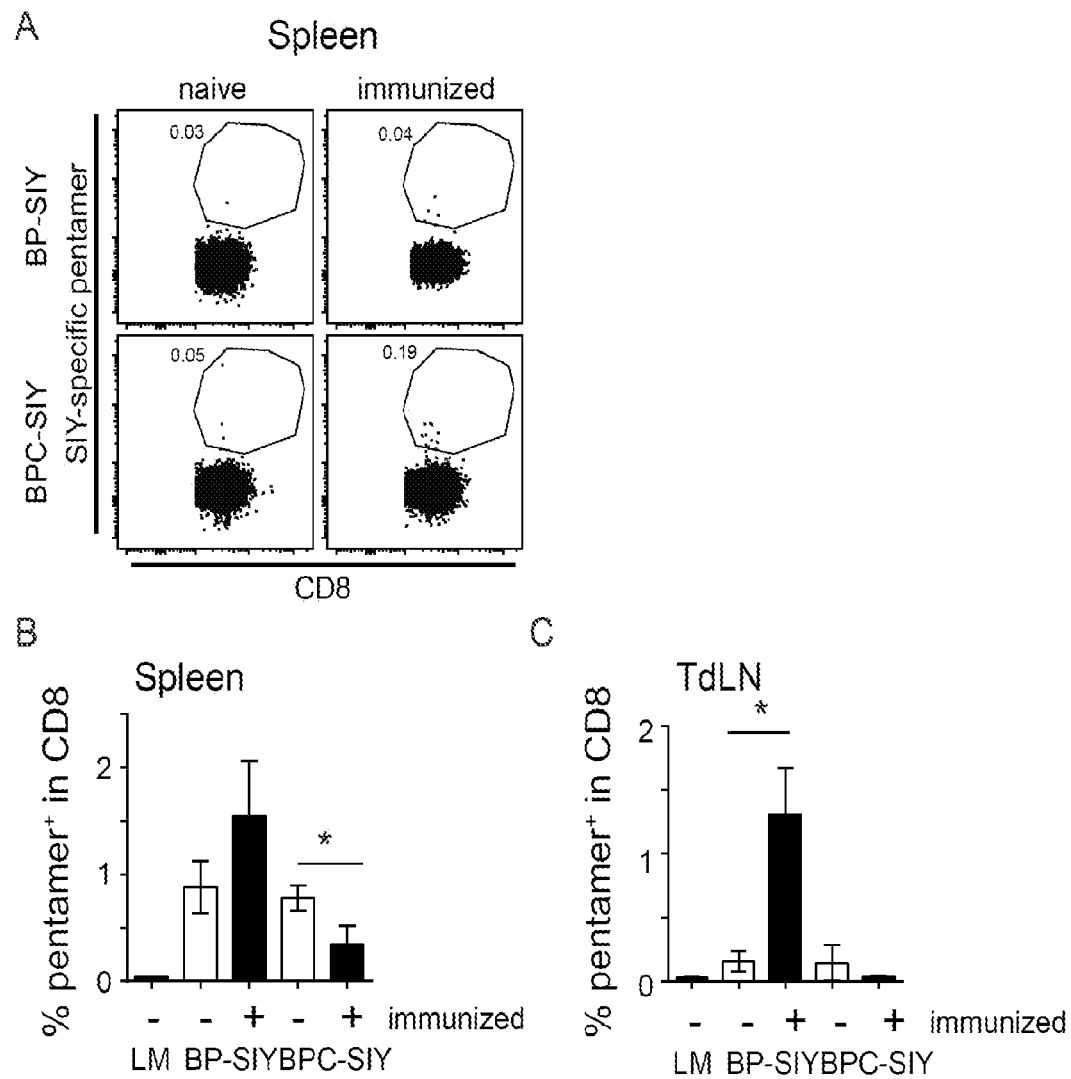
FIG. 18. Reactivation of SIY-specific memory T cells in the periphery of tumor-bearing mice. (A) Representative example of pentamer staining for SIY-specific T cells in the spleen of naïve or immunized tumor-bearing BP-SIY and BPC-SIY mice, isolated at the end point of the experiment shown in FIG. 16. (B-C) Statistical analysis of antigen-specific cells detectable within the spleen (B) and TdLN (C) assessed though SIY-specific pentamer staining at the end point of the experiment.

Increased Tumor Control in Tumors with Baseline/β-Catenin Signaling is Associated with Reactivation of Antigen-Specific Peripheral Memory T Cells and Increased Tumor Infiltration In order to identify if the lack of tumor control was associated with differences in the reactivation of the memory immune response, the systemic as well as local SIY-specific immune response was assessed at the endpoint of experiments. The systemic immune response was assessed using an IFN-γ ELISpot assay on splenocytes from tumor bearing naïve and immunized BP-SIY and BPC-SIY mice. A strong SIY-response in spleen isolated from immunized BP-SIY mice was observed (FIG. 17A). The response detected was 6-7 fold higher that observed at the two-month time point when the memory response was assessed (FIG. 15C). These data indicate a defect in memory activation in β-catenin-positive positive BPC-SIY tumor bearing mice. Consistently, an increase in percent and absolute number of SIY-specific T cells was detected, assessed using a SIY-specific pentamer, in tumors of immunized BP-SIY mice (FIG. 17B-D). In contrast, a distinct SIY-specific T cell population was not detected in either of the β-catenin-positive BPC-SIY tumor cohorts (FIG. 17B-D). When assessing the frequency of SIY-reactive T cells in the spleen as well as the tumor-draining lymph node (TdLN) no differences were observed, with the exception of an increased in pentamer positive cells in TdLN of immunized BP-SIY tumor bearing mice (FIG. 18A-C). Data indicate that β-catenin-positive tumors (BPC-SIY) are able to exclude even a potent anti-tumor specific memory response and thereby avoid immune surveillance. In contrast, β-catenin-negative tumors comprise a strong and antigen-specific immune infiltrate within the tumor microenvironment and a delay in tumor growth is detected.

Figure 19:
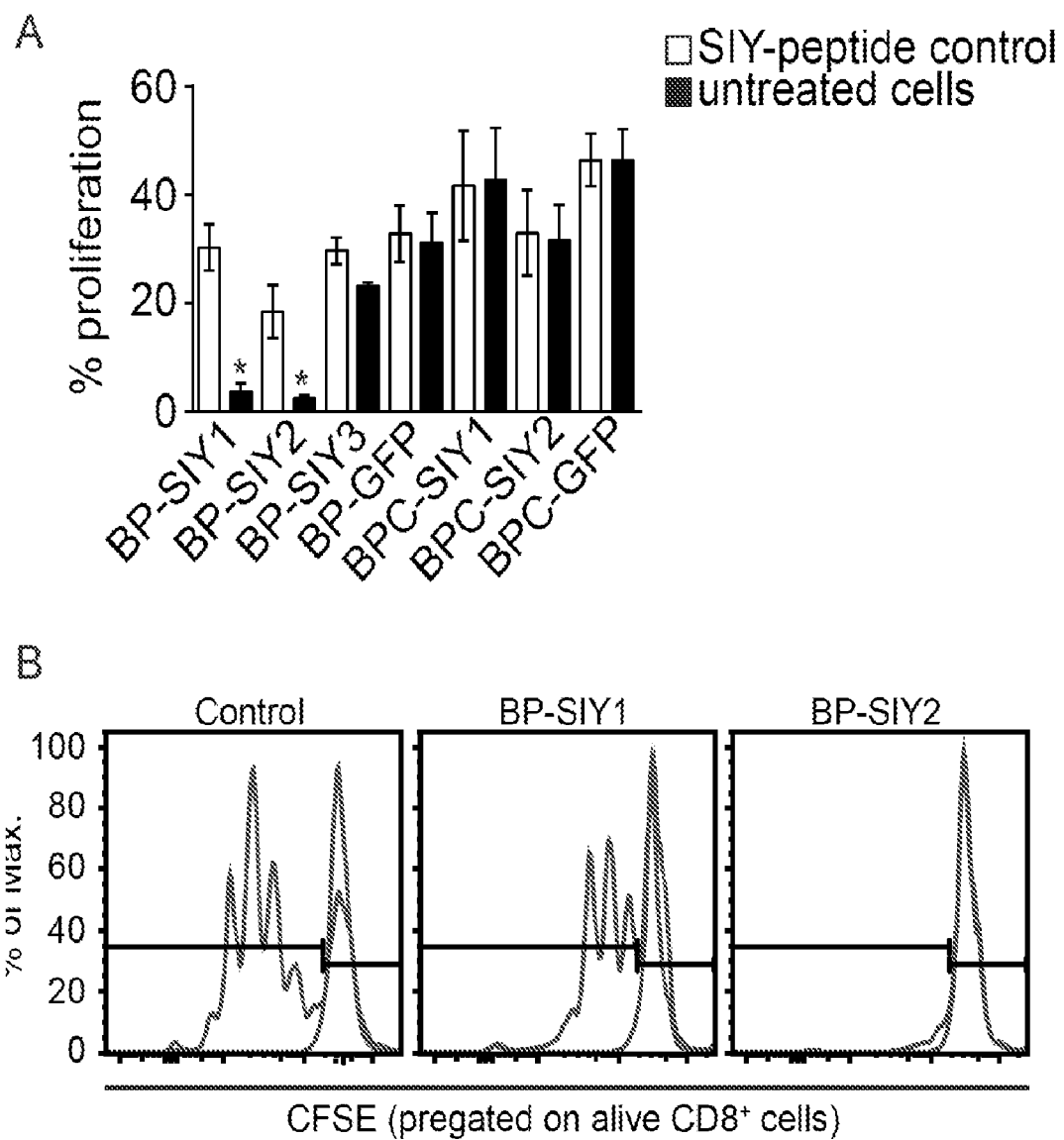
FIG. 19. Immune surveillance results in a loss of immunogenicity in β-catenin-negative tumor cells but not in β-catenin-positive tumor cells. (A) Depicts the immune-stimulatory capacity (proliferation) of tumor cell lines isolated from MC57-SIY immunized, BP-SIY and BPC-SIY tumor bearing mice. The immune stimulatory potential was assessed by measuring T cell proliferation in a co-culture assay of CFSE-labeled 2C TCR transgenic T cells and untreated or SIY-peptide pulsed tumor cells. Transduced tumor cells isolated from antigen negative mice were used as positive control. (B) Representative examples of histograms depicting CFSE dilution for control (unstimulated vs. transduced BP cell lines) and the two cell lines shown defective T cell stimulation. (C) PCR analysis assessing the SIY-mRNA levels in the cell lines used in A (representative for two independent experiments). (D) Genotyping PCR confirming the presence of the SIY-LUC transgene in the BP-SIY1 cell line. (E) Representative histogram assessing the expression profile of MHC-I on the surface of untreated or IFN-γ-treated BP-SIY1 and BP-SIY2 cell lines.
Figure 19:
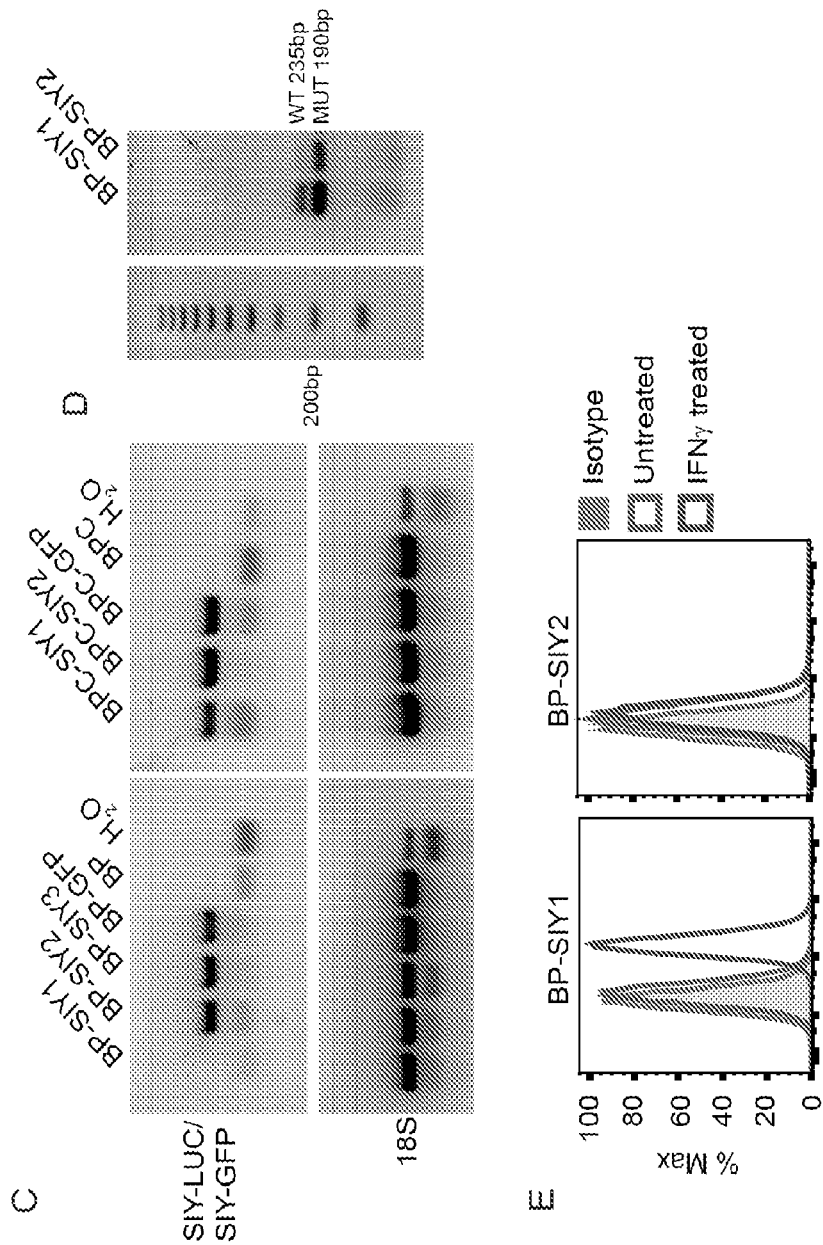
Figure 20:
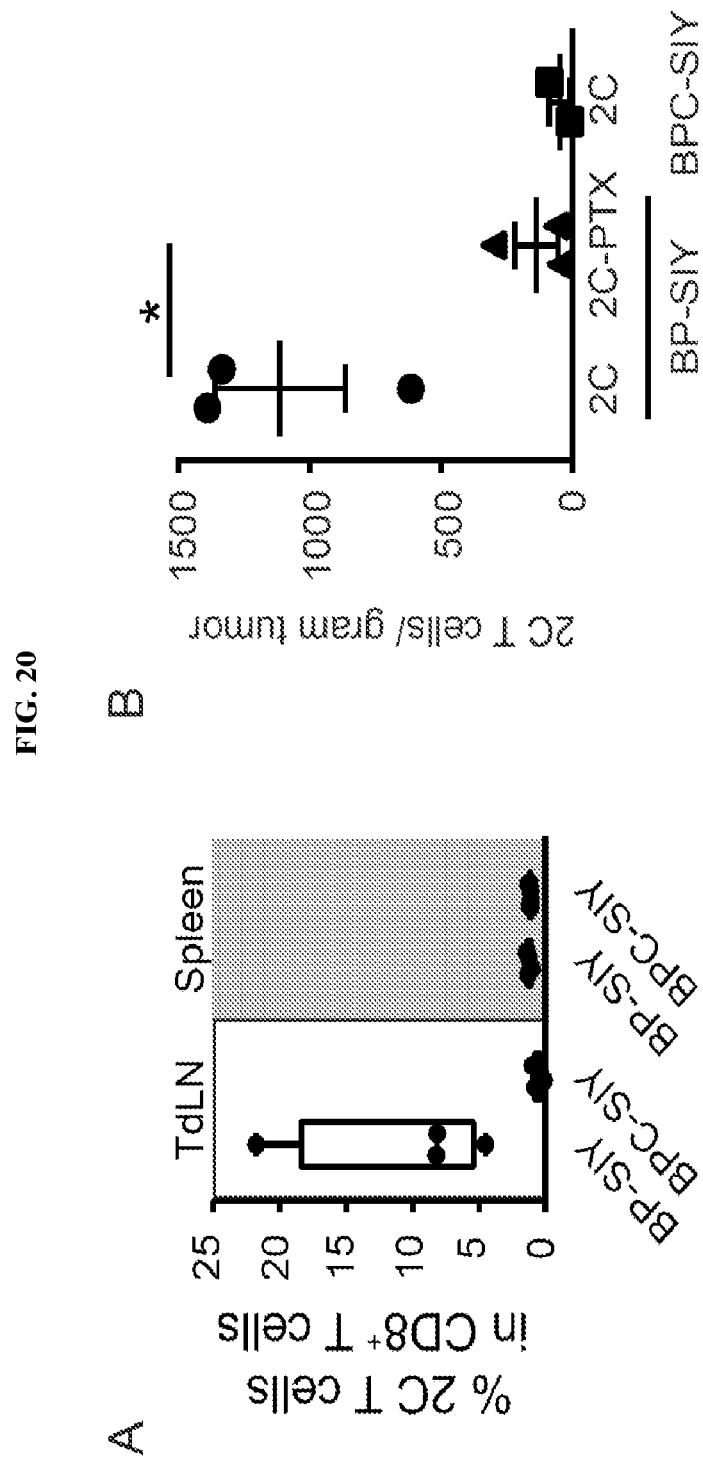
FIG. 20. Adoptively transferred 2C T cells migrate into the tumor microenvironment in a chemokine dependent manner. (A) Amount of effector T cells present in spleen and TdLN three days post adoptive transfer of 1×10$^6$ in vitro activated T cells. Left panel shown percent within CD8$^+$ T cells and right panel depicts amount total 2C T cells per gram tumor. Shown are mean with 95$^{th}$ percentile for BP-SIY and BPC-SIY. (B) Amount (number/gram tumor) of 2C T cells detectable after 72 h post transfer into BP-SIY (circle) and BPC-SIY (square) tumor or after transfer of 2C T cells, pretreated with pertussis toxin, into BP-SIY tumors (triangle).

Mechanisms of Immune Surveillance can Only be Observed in β-Catenin-Negative Tumors Experiments were conducted during development of embodiments herein to interrogate the notion that β-catenin-negative tumors are exposed to immune surveillance, while tumors with up-regulation of tumor cell-intrinsic β-catenin signaling are protected from this process through exclusion of T cells. The process of immune surveillance is typically characterized by the outgrowth of less immunogenic tumor cell clones. In order to interrogate the immunogenicity of the tumor, the autochthonous tumors were harvested at the endpoint of the experiment and generated transplantable cells lines through injection into Rag2$^{-/-}$ mice. After two in vivo-passages, the cell lines were adapted to cell culture conditions and three BP-SIY tumor cell lines (3/10) and two BPC-SIY tumor cell lines (2/8) were obtained. As readout of immunogenicity of the obtained tumor cell lines, tumor cells were co-cultured with CFSE-labeled SIY-specific TCR-transgenic 2C T cells for 72 h. Subsequently, T cell activation was assessed by CFSE dilution as readout of antigen recognition. As control, tumor cells pulsed with exogenous SIY-peptide as well as tumor cells established from SIY negative animals but transduced with a SIY-GFP expression plasmid were used. While both cell lines isolated from BPC-SIY mice showed similar capacities to activate T cells when compared to the corresponding peptide pulsed control, only one (BP-SIY3) out of the three BP-SIY isolated tumor cell lines showed those characteristics (FIG. 19A). Further, it was observed that one of the BP-SIY cells lines (BP-SIY2) was incapable of stimulating T cells even in the presence of exogenous peptide (FIG. 19B). Either loss of antigen expression or down-regulation of MHC-I expression are the predominant mechanisms resulting in reduced immunogenicity of tumor cells. First, the expression of SIY antigen was assessed in all cell lines. It was observed that BP-SIY1, the cell line which only failed to stimulate 2C T cell in the absence of exogenous peptide, lost the SIY mRNA transcript. All other cell lines retained SIY mRNA expression (FIG. 19C). To assess if this was due to loss of the genetic locus or rather epigenetic silencing, the cell line was genotyped, identifying that the genetic locus was still present. Based on this observation as well as previous reports, which suggested epigenetic silencing as the predominant mechanism of immune escape in this model, it is conclusive that the SIY mRNA expression on BP-SIY1 cells was down-regulated through epigenetic changes (FIG. 19D). To assess the second plausible mechanism of reduced immunogenicity, the expression level of MHC-I was determined, with or without stimulation with IFN-Γ, on both cell lines, which failed to stimulate 2C T cells. Consistent with previous observations, expression or IFN-γ-induced up-regulation of MHC-I was not detected on BP-SIY2 cells, indicating that down-regulation of MHC-I expression is the dominant mechanism in this cell line (FIG. 20E). Outgrowth of tumor with reduced immunogenicity was observed exclusively from BP-SIY tumor-bearing mice, which have had a pre-existing anti-tumor immune response (immunization through MC57-SIY) and not from BPC-SIY tumor bearing mice comprising the same SIY-specific memory response. Those data indicated that tumor cell intrinsic activation of the WNT/β-catenin pathway mediates resistance even against a strong pre-existing, antigen-specific memory response.

Absence of Tumor Control in Tumors with Activated β-Catenin Signaling is Due to Lack of Recruitment of Effector T Cells into the Tumor Microenvironment Expansion of an SIY-specific peripheral immune response was not observed upon challenge with the autochthonous tumor in BPC-SIY mice. Therefore, experiments were conducted during development of embodiments herein to further investigate if the lack of effector T cell infiltration in β-catenin-positive tumor was due to lack of T cell reactivation or due to ineffective effector T cell recruitment into the tumor. In some embodiments, the separation of those two mechanisms may be of importance, since it is a common observation that non-T cell-inflamed tumor lesions coincide with T cell-inflamed lesions, capable of activating the systemic immune response. Further, in some embodiments, therapeutic solutions overcoming the lack of T cell-infiltration would be different between both scenarios.

Figure 21:
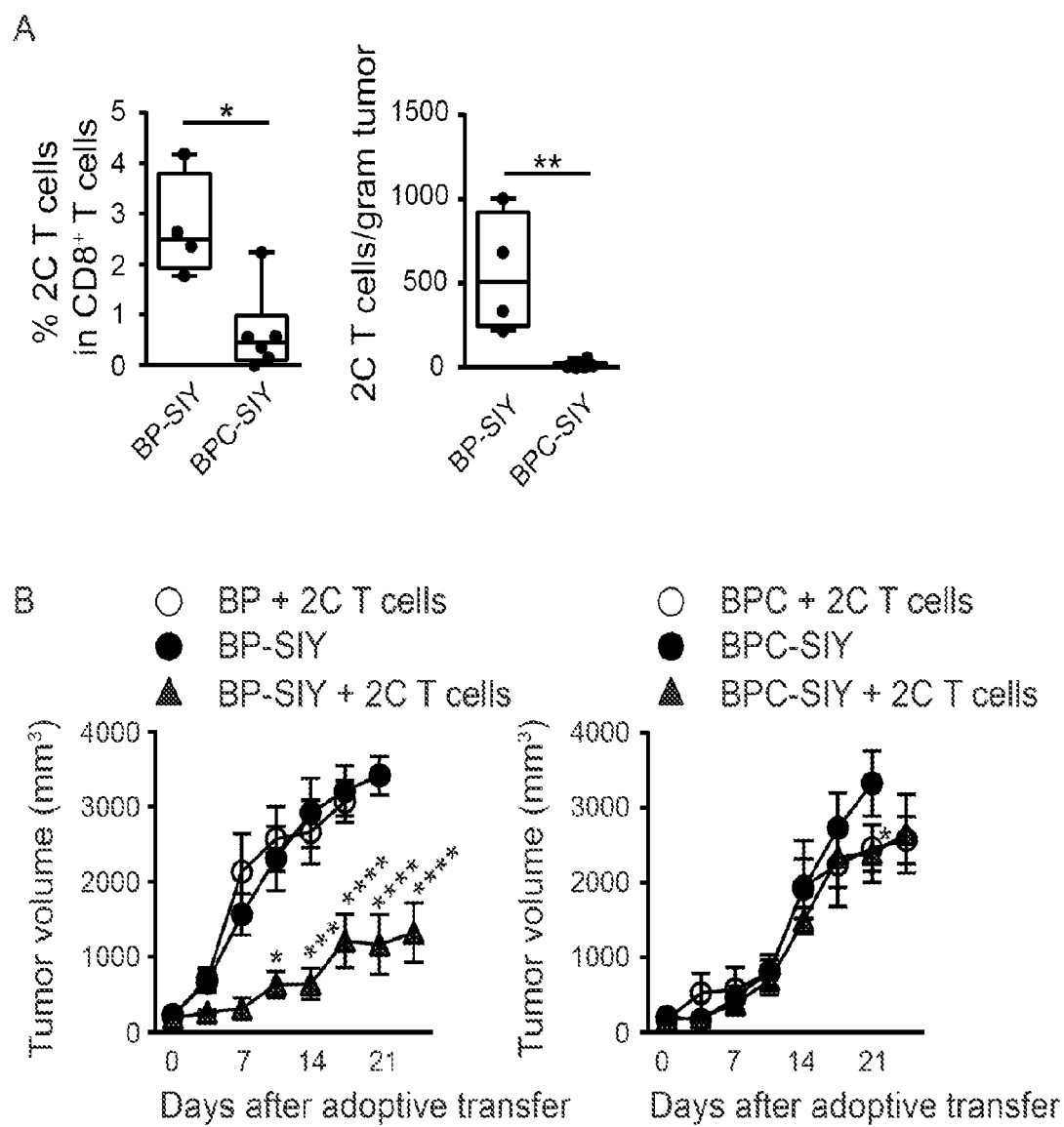
FIG. 21. Adoptively transferred SIY-specific TCR-transgenic effector T cells only infiltrate and control BP-SIY tumor and not BPC-SIY tumors. (A) Depicts the amount of detectable 2C T cells within the tumor 3 days post adoptive transfer of 1×10$^6$ in vitro activated T cells. Left panel shown percent within CD8 T cells and right panel depicts amount total 2C T cells per gram tumor. Shown are mean with 95$^{th}$ percentile for BP-SIY and BPC-SIY. (B) Depicts tumor outgrowth curves of BP-SIY and BPC-SIY tumor (filled circle) or after adoptive transfer of 10×10$^6$ 2C T cells (filled triangle). As controls, antigen-negative BP and BPC mice were treated with the same amount of 2C T cells (open symbols). Adoptive transfer was performed at day 21-post tamoxifen application.

To assess if lack of T cell infiltration was due to a defect in effector T cell recruitment, an adoptive T cell transfer approach was used, transferring in vitro-activated effector 2C T cells into tumor bearing BP-SIY and BPC-SIY mice. As a first assessment, only the capacity of the effector T cells to migrate into the tumor within 72 h was analyzed. It was detected that even in vitro-activated 2C T cells failed to be recruited into the tumor microenvironment of β-catenin-positive tumors (FIG. 21A). In contrast, experiments were able to detect infiltration of 2C effector T cells into β-catenin-negative tumors. This observation was accompanied by an increased accumulation of 2C T cell in TdLN of BP-SIY mice compared to BPC-SIY mice, while the amount of 2C T cell detected in the spleen was comparable (FIG. 20A). Secondly, experiments addressed whether recruitment of 2C effector T cells upon adoptive transfer results in a therapeutic effect in this model. Therefore, the amount of transferred cells was increased to $5\times10^8$ cells/kg, an amount that is routinely administered in the context of adoptive T cell transfer therapy. Indeed, a highly significant reduction in tumor outgrowth was observed when 2C effector T cells were administered into BP-SIY mice with a preexisting tumor, when compared to untreated mice or mice bearing SIY negative tumors (FIG. 21B). Consistent with the observation that effector T cells are not infiltrating into β-catenin-positive tumor, no therapeutic benefit of adoptive transfer of 2C T cells was observed in the context of BPC tumors (FIG. 21B). It was next addressed if effector T cell infiltration into β-catenin-negative tumors was due to a directed, chemokine-dependent migration. In vitro-activated effector 2C T cells were treated for 12 h with pertussis toxin (PTX) prior to injection into BP-SIY tumor bearing hosts. PTX inhibits G-protein-coupled receptors, including chemokine receptors, and thereby inhibits a directed, chemotaxis induced migration of treated T cells. It was observed that this block of chemokine mediated migration completely block the migration of effector 2C T cells into β-catenin-negative tumors (FIG. 20B), while transferred cells were still detected in the spleen and TdLN. In sum, these data indicate that tumor cell-intrinsic activation of the β-catenin results in a defective recruitment of effector T cells into the tumor microenvironment when compared to β-catenin-negative tumors. Further, the data indicate that the recruitment of effector T cells is due to a chemokine: chemokine receptor mediated migratory stimulus.

Figure 22:
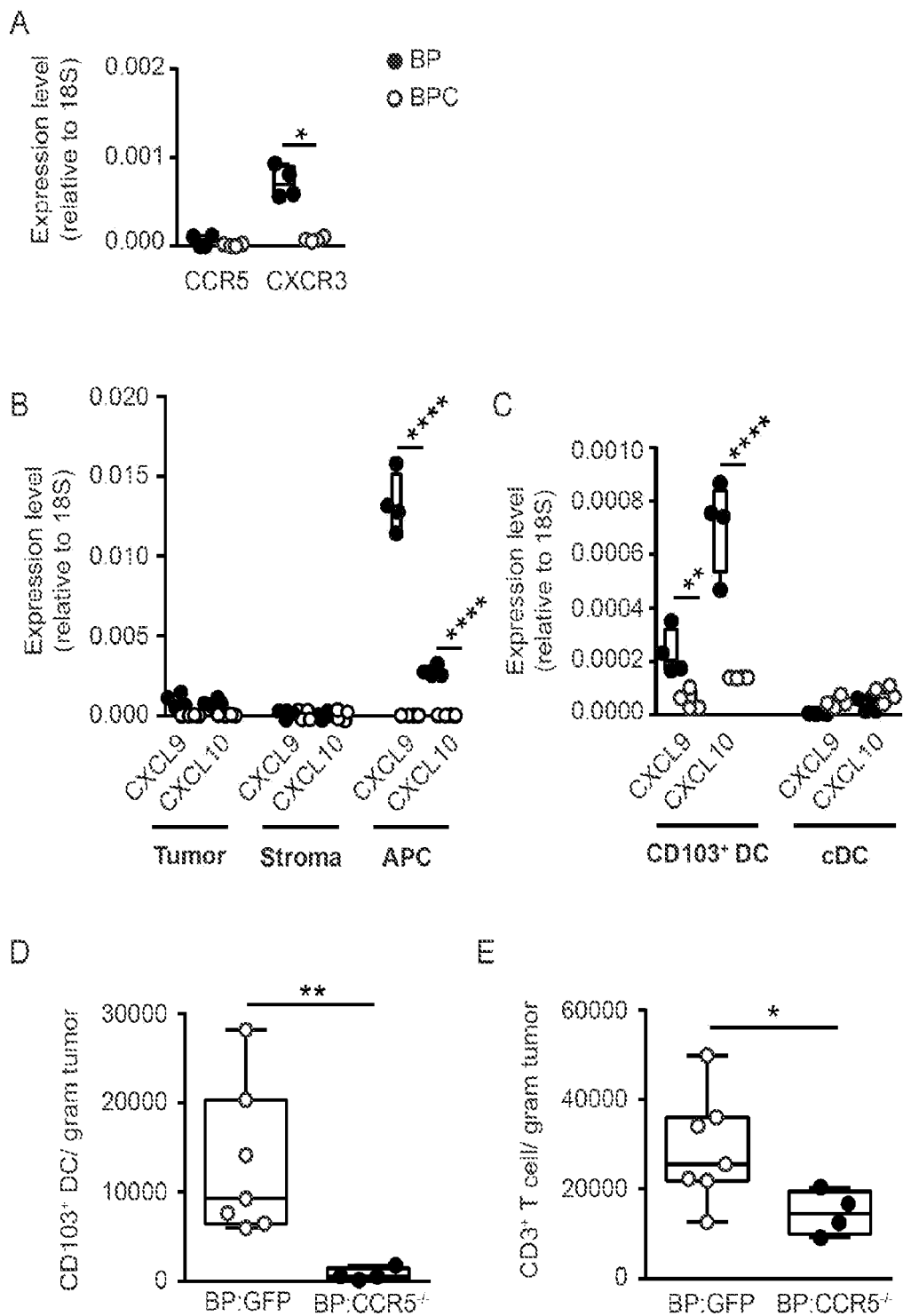
FIG. 22. CXCR3-CXCL9/10 chemokine axis and the presence of CD103$^+$-dendritic cells are associated with the presence of T cells in the tumor microenvironment. (A) Depicts the expression level of chemokine receptors CCR5 and CXCR3 on tumor-infiltrating T cells isolated from BP (black) and BPC (gray) tumors. Expression was assessed on T cells isolated from two tumors per data point via quantitative real-time PCR and normalized to 18S. (B-C) Similarly assessed expression levels of CXCL9 and CXCL10 in tumor (CD45$^-$, YFP$^+$), stroma (CD45$^-$, YFP$^-$) and ACP (CD45$^+$, MHCII$^+$, CD11c$^+$) (B) and on CD103$^+$ and cDC (MHCII$^+$, CD11c$^+$, CD103/CD8α$^-$). (D-E) CCR5$^{-/-}$ and control (GFP) bone marrow chimeras with BP hosts were generated and following tumor induction the amount of tumor infiltrating CD103$^+$ DC (D) and CD3$^+$ T cells (E) were assessed and are depicted as number/gram tumor.
Figure 23:
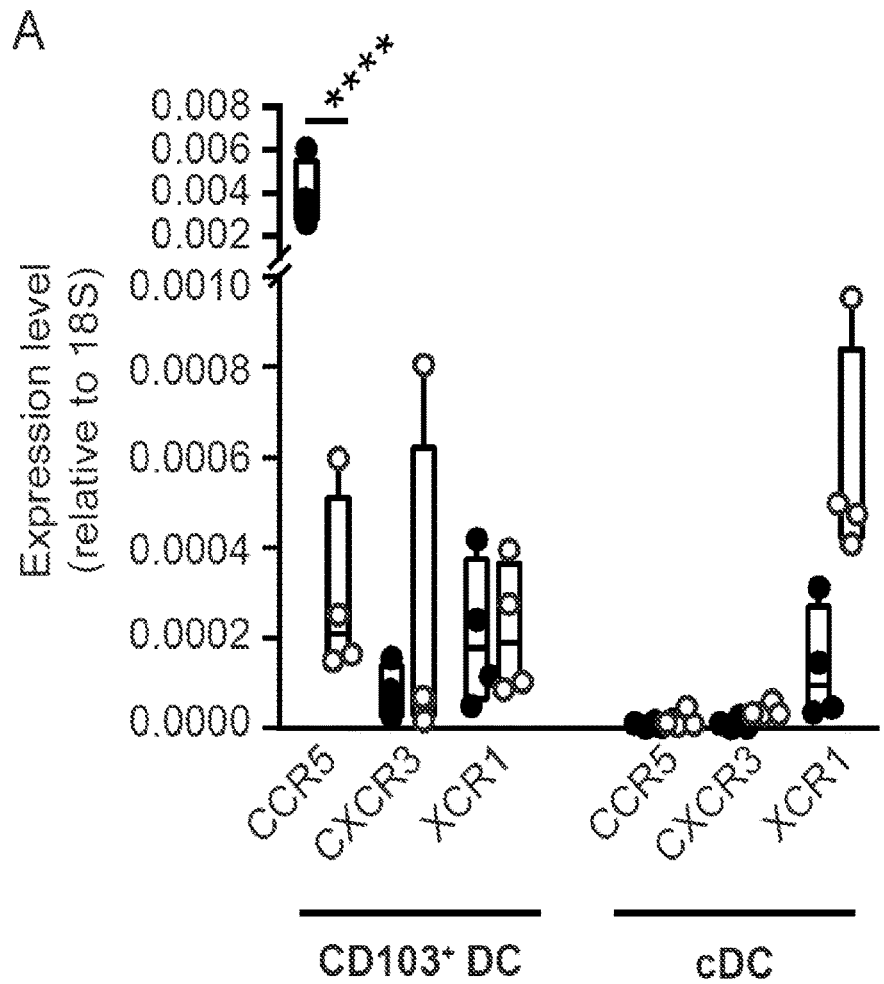
FIG. 23. CCR5 dependent recruitment of CD103+ dendritic cells is important of the recruitment of effector T cells into the tumor microenvironment. (A) Chemokine expression profiling on CD103$^+$ and conventional DC assessed from sorted DC via quantitative PCR analysis. (B) Amount of conventional CD103$^-$ DC found in tumors with control (GFP) or CCR5$^{-/-}$ bone marrow (corresponding data to FIG. 22D, E).
Figure 23:
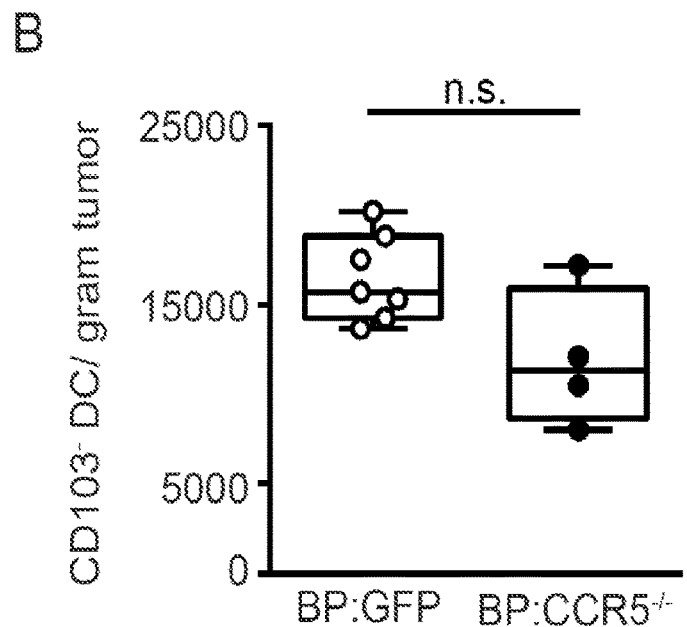

CXCR3-CXCL9/10 Chemokine Axis is Required for the Recruitment of Effector T Cells into the Tumor Microenvironment In order to elucidate the chemokine stimulus responsible for the recruitment of effector T cells into the tumor microenvironment of β-catenin-negative tumors, experiments assessed the chemokine receptor profile on endogenous effector T cells infiltrating BP and BPC tumors. Consistent with previous observations, it was observed that $CD3^+$ T cells isolated from β-catenin-negative BP tumor showed expression of CXCR3, a chemokine receptor reported to be expressed on effector T cells (FIG. 22A). Expression of CCR5 was not observed on tumor-infiltrating T cells, which excluded CCL4 as the driving chemokine for T cell infiltration, known to be differentially expressed between BP and BPC tumors. Similarly, expression of either CCR5 or CXCR3 was not observed on T cells isolated from BPC tumors, indicating that those T cells are not effector T cells (FIG. 22A). T cells from BPC tumor showed expression of XCR1, a chemokine receptor responsible for skin homing, which suggests that these T cells are tissue residing memory cells with no direct anti-tumor functionality. Experiments were conducted during development of embodiments herein to identify the cellular source of the CXCR3-engaging chemokines, CXCL9 and CXCL10. In order to do so, BP and BPC mice were crossed to an YFP-reporter mouse strain, marking all tumor cells with YFP. Subsequently, YFP-positive tumor cells, non-hematopoietic stroma cells ($CD45^-$, $YFP^-$) and antigen-presenting cells ($CD45^+$, $MHCII^+$, $CD11c^+$, $CD11b^+$) were separated, and quantitative-PCR for CXCL9 and CXCL10 was performed. Experiments identified that none of the cell types isolated from BPC tumor produced a significant amount of CXCR3 chemokines, while expression was detected in tumor cells as well as APC isolated from β-catenin-negative tumors (FIG. 22B). Contrasting the expression levels of CXCX9 and CXCL10 between tumor cells and APC demonstrates that for both chemokines tumor-residing APC produced, a significantly higher amount than tumor cells and CXCL9 appeared to be higher expressed in tumor-residing APC compared to CXCL10. Within the APC compartment, the most significant alteration between β-catenin-positive and negative tumor was found to be in the $CD103^+$ dendritic cell compartment. Experiments therefore focused on the separation of $CD103^+$ DC from the tumor-residing APC pool in order to assess if the difference in this compartment explain the differential secretion of CXCR3 chemokines between the two tumor types. Indeed, experiments assessing the expression of CXCL9 and CXCL10 in $CD103^+$ DC and conventional DC ($CD45^+$, $MHCII^+$, $CD11c^+$, $CD103^-$) demonstrate that the predominant source of chemokine production were $CD103^+$ DC (FIG. 22C). Consistent with the finding that only $CD103^+$ DC isolated from β-catenin-negative but not from β-catenin-positive tumors were capable of producing CXCR3-engaging chemokines. It was further confirmed that $CD103^+$ DC are recruited into the tumor microenvironment by CCR5: CCL4-dependet recruitment (FIG. 23A). Experiments took advantage that CCR5: CCL4 appeared to be the predominant recruitment for $CD103^+$ DC while other cell types seemed to be recruited independent of this axis and generated bone marrow chimeras of $CCR5^{-/-}$ mice in BP hosts. In tumor bearing mice, a significant reduction in $CD103^+$ DC infiltrating into the tumor was observed, while infiltration of conventional DC appeared to be unperturbed (FIGS. 22D and 23B). Furthermore, significant changes in the DC subsets in peripheral lymphoid organs were not observed. Consistent with the notion that tumor-residing $CD103^+$ DC are responsible for the effective recruitment of effector T cells, it was observed that $CCR5^{-/-}$ bone marrow chimeras have a significant reduction of tumor-infiltrating T cells compared to the control bone marrow chimeras (GFP) (FIG. 22E). Altogether, data demonstrate that the migration of effector T cells into the tumor microenvironment depends on the production of CXCR3-engaging chemokines. In β-catenin-negative, T cell-inflamed tumors, the predominant source of those chemokines, CXCL9 and CXCL10, are $CD103^+$ tumor-residing DC, a subset of DC, which is absent in tumors with activated β-catenin signaling eliminating the recruitment signal for effector T cells.

Figure 24:
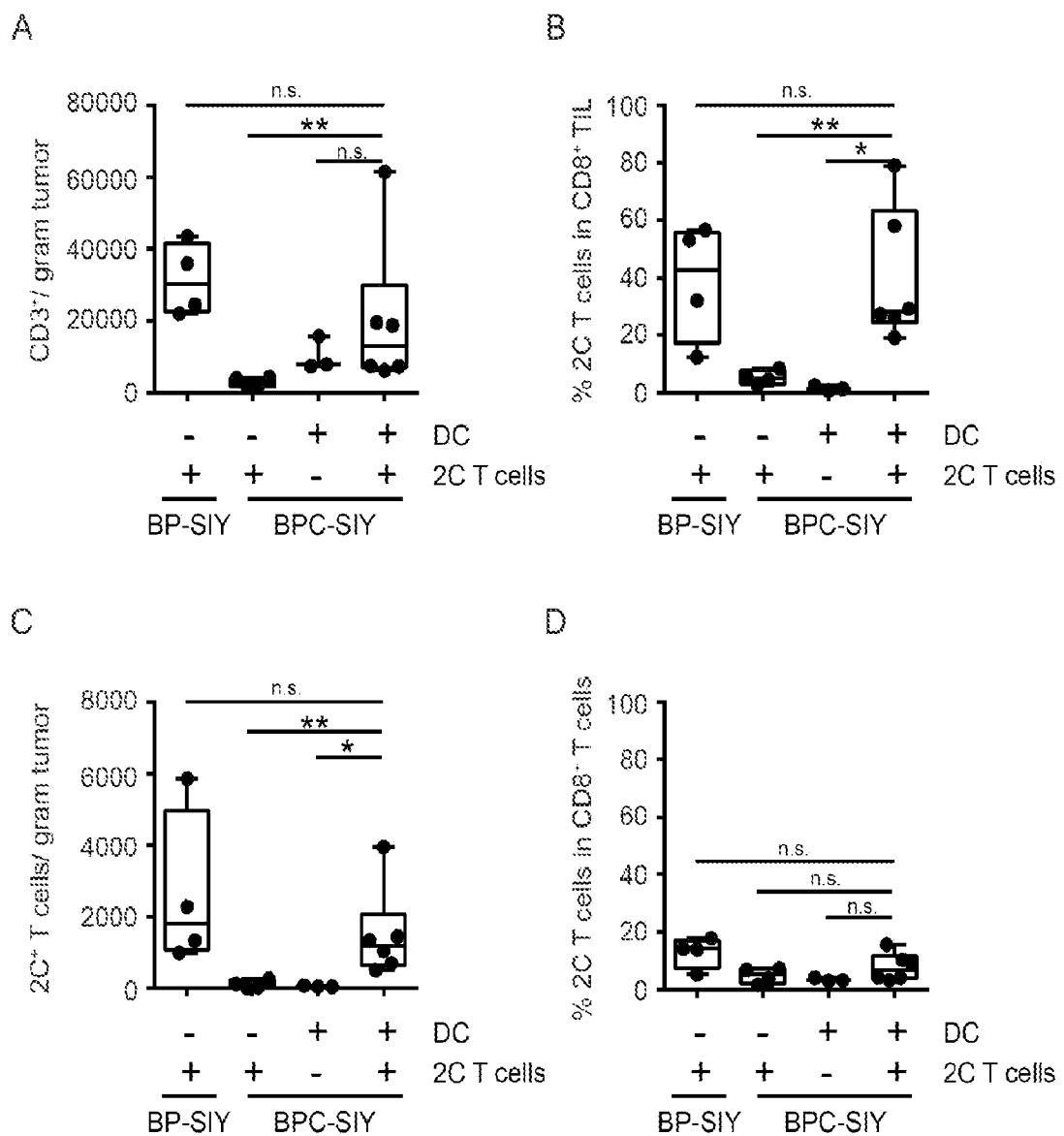
FIG. 24. Batf3-driven dendritic cells are sufficient and required for recruitment of effector T cells into the tumor microenvironment. (A-D) BP-SIY and BPC-SIY tumor bearing mice were injected twice intra-tumorally with Flt3-L derived DC or control injected with PBS 72 h prior to intravenous injection of effector 2C T cells. 3 days post T cell injection amount of T cells (A), 2C T cells in the tumor (B-C) and 2C T cell in the TdLN were assessed and are depicted as number per gram of tumor or percent in CD8 T cells. (E) Batf3 BM chimeras and 2C recruitment.

Batf3-Driven Dendritic Cells within the Tumor Microenvironment are Required for the Recruitment of Effector T Cells into the Tumor Microenvironment Experiments were conducted during development of embodiments herein to determine if administration of CD103-like, Flt3-ligand derived, bone marrow DC would affect recruitment of effector T cells into β-catenin-positive tumors. Flt3-ligand derived bone marrow DC activated with polyI:C was injected into BPC-SIY tumors 48 h before in vitro activated effector 2C T cells were injected into tumor bearing mice. Injection of Flt3-ligand derived DC mildly affected the recruitment of endogenous T cells into BPC-SIY tumor, while injection of effector 2C T cell had no impact on the endogenous T cell response (FIG. 24A). In contrast recruitment of effector 2C T cells, as percent of $CD8^+$ T cell as well as in absolute numbers, was significantly increased in mice receiving intra-tumoral DC compared to PBS-injected control mice (FIG. 24B-C). Most strikingly, a single injection of Flt3-ligand derived DC was sufficient to enhance effector 2C T cell recruitment in BPC-SIY tumors to similar levels as observed in unperturbed BP-SIY mice receiving also adoptive transfer of 2C T cells, while accumulation in the TdLN seemed to be unaffected (FIG. 24D). The data indicate that tumor-residing CD103+ DC are mediating effector T cell recruitment into the tumor microenvironment, and that lack of T cell infiltration into tumor is due to a lack of CD103+ DC due to alterations in tumor cell-intrinsic signaling pathways (e.g. activation of the Wnt/(β-catenin pathway).

Figure 25:
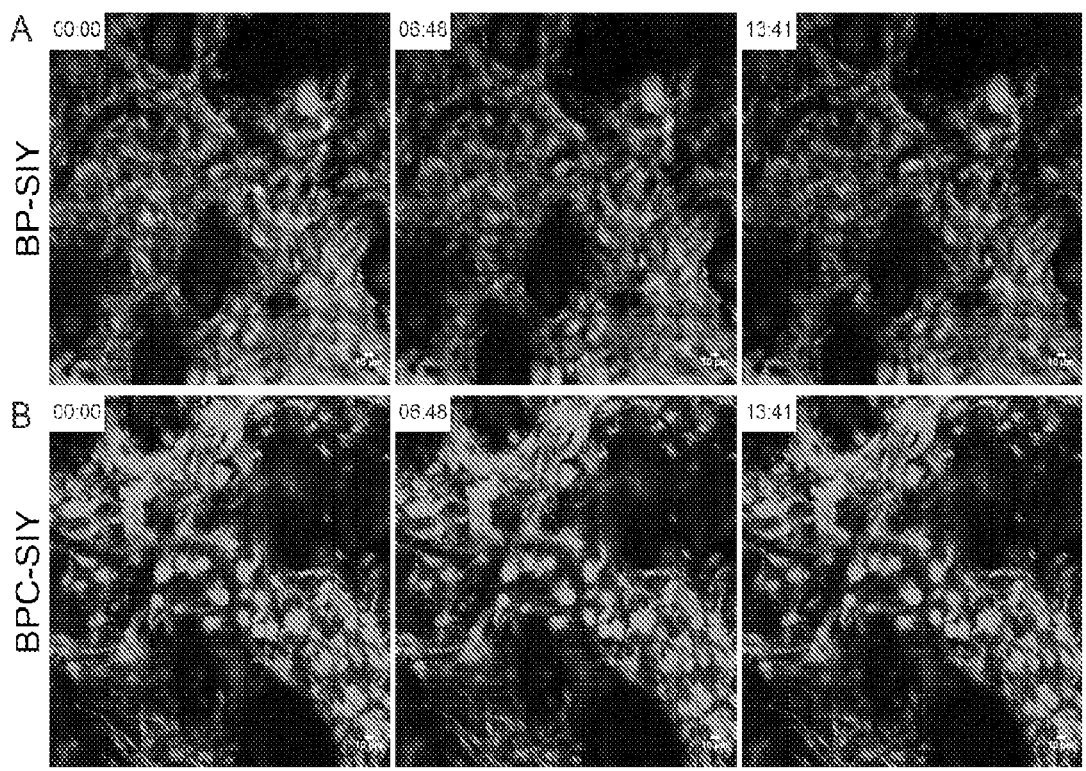
FIG. 25. Effector T cells infiltrating BPC-SIY show reduced motility and interaction with tumor cells compared to T cells infiltrating BP-SIY. (A-B) Representative examples images showing 2C effector T cell migrating through BP-SIY (A) or BPC-SIY (B) tumors. (C) Amount of adoptively transferred effector 2C T cells assessed in BP-SIY and BCP-SIY tumors 72 h post transfer. (D-E) Representative example of T cell motility analyses with start position being normalized to 0. (F-G) Velocity (speed, μm/sec) (F) and displacement (distance, μm) of tumor-infiltrating effector 2C T cells assessed 48-72 h post adoptive transfer. (H) Mean distance between T cell (center) and nearest tumor cell (edge) with a maximal distance of 50 μm.
Figure 25:
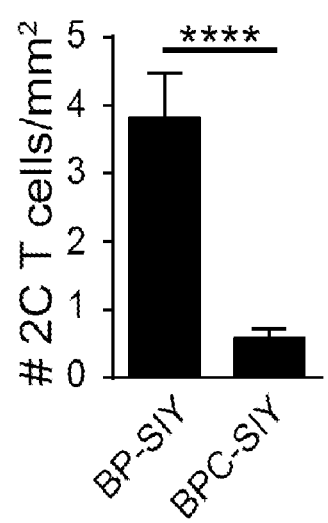
Figure 25:
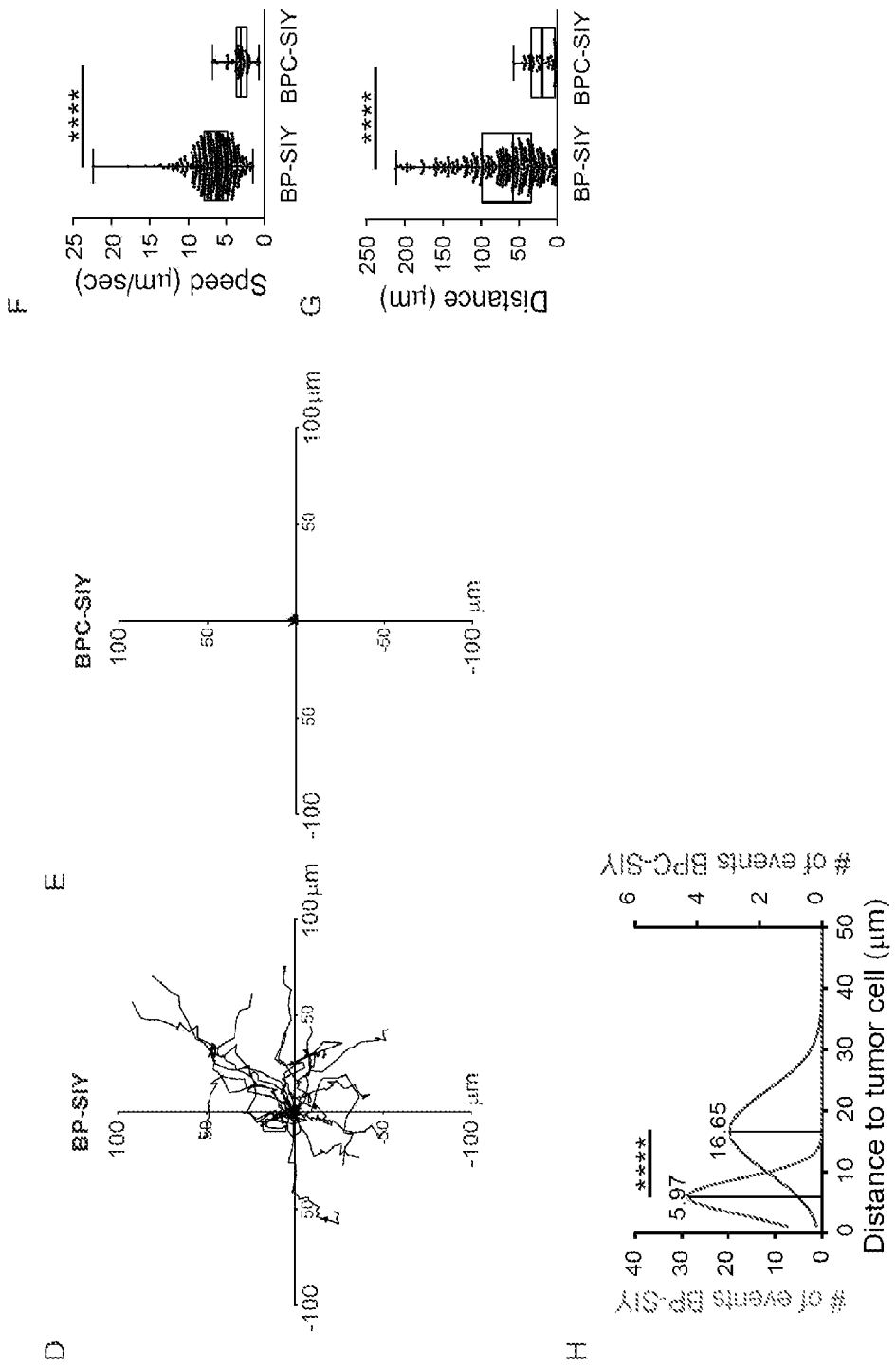
Figure 26:
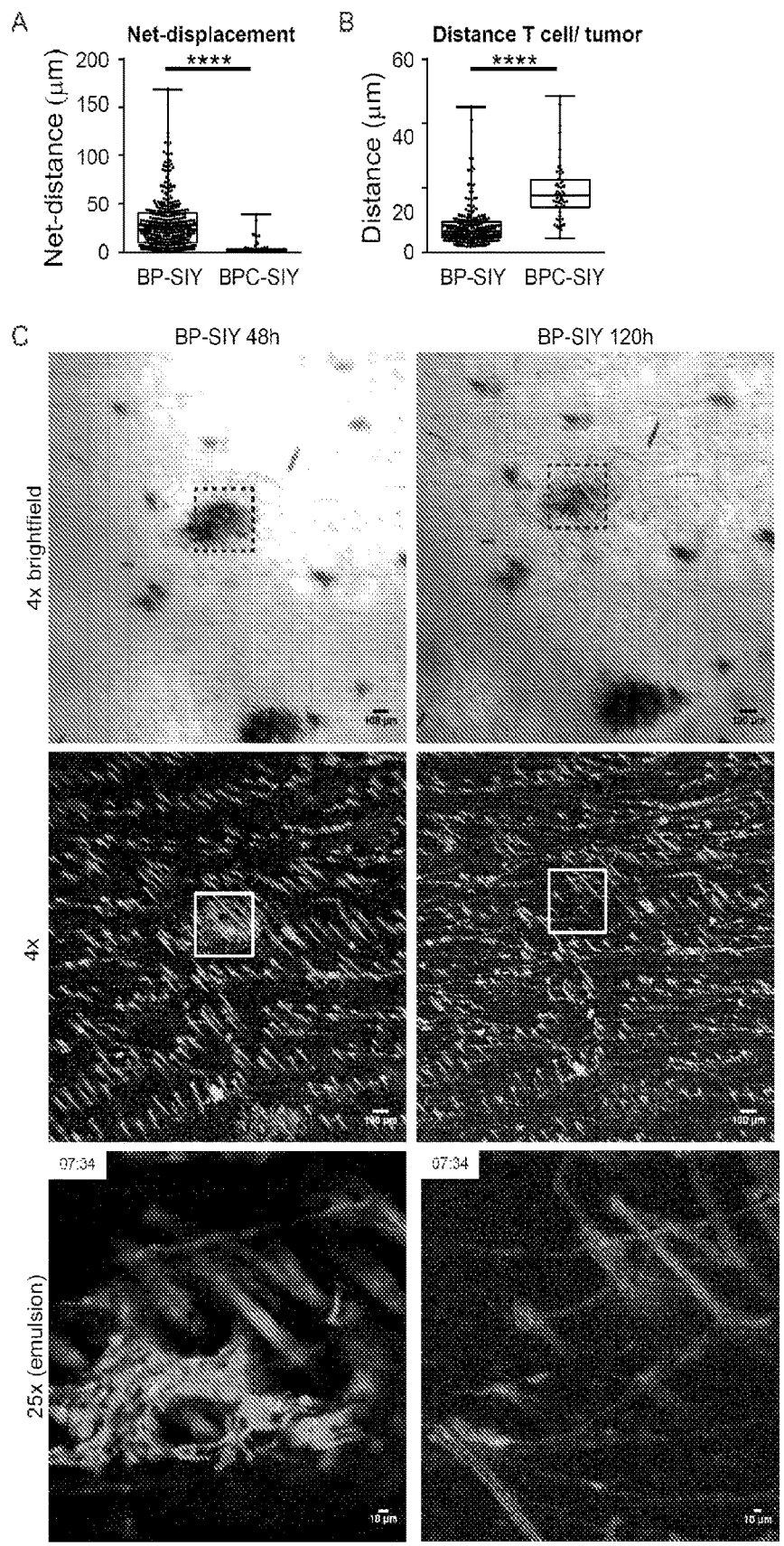
FIG. 26. Adoptive transfer of effector T cell results in tumor eradication exclusively in β-catenin-negative tumors. (A) Net-displacement of adoptively transferred T cell in β-catenin-negative and positive tumors. Net displacement was calculated from start and end points obtained from the total displacement/distance analysis (FIG. 25G) and displays the most linear distance traveled by a given T cell. (B) Depicts the individual distances between tumor cell and T cell used to calculate the mean distance. Only events with a distance of 50 μm or less were assessed. (C) Shows representative example of eradicated tumor lesion in BP-SIY tumor model after transfer of effector 2C T cells. Left tumor lesion on day 2 post transfer, brightfield, 4× and 25× magnification (top to bottom) and right same area on day 5 post transfer.

Effective Recruitment of Effector T Cells into the Tumor Microenvironment is Associated with Increased Motility and Co-localization with Tumor Cells Experiments repeatedly demonstrate a low infiltration of effector T cells into (β-catenin-positive tumor. Despite this observation, experiments do not detect any positive feedback on infiltration, which would be expected even if only very few effector cells are infiltrating the tissue. Since the cell numbers are a limiting factor to study phenotype and function using flow cytometry, an intra-vital imaging technique was developed to allow visualizing effector T cell behavior in a naturally arising autochthonous tumor over time. In order to allow visualization of the tumor cells, BP-SIY and BPC-SIY mice were intercrossed with BP-YFP or BPC-SIY mice, respectively, which allowed antigen-expression as well as visualization of transformed cells by YFP expression. Further, the application of 4OH-tamoxifen was adjusted to flank of the mice to allow the surgical implantation of a metal frame holding the cover slip over the tumor. The static implantation of the frame in combination with the imaging software also allowed the sequenced imaging of individual tumor lesions over the course of multiple days. Tumor induction and adoptive transfer of red-fluorescently-labeled effector T cells was sequences by 21 days since this allowed imaging of individual tumor lesions. The metal frame was implanted 24 h post adoptive transfer and imaging was initiated the following day and carried out over the course of one week. Using this experimental setup enabled visualization of transferred effector T cells (red) and tumor cells (green) in both mouse models (FIG. 25A,B). As a first control, the number of transferred T cells present in either tumor microenvironment was enumerated. Despite the surgical manipulation, a significant reduction in effector T cell infiltration into BPC-SIY tumors was still observed (FIG. 25C). Effector T cells infiltrating BP-SIY tumor and BPC-SIY tumors comprised a strikingly different migratory behavior (FIG. 25A,B). In order to quantify this observation, transferred effector T cells were tracked individually using MtrackJ and spider plots were generated indicating the overall displacement (FIG. 25D,E). When quantified over multiple lesions and individual mice a highly significant reduction in T cell velocity, displacement (total traveled distance) as well as net displacement (directed traveled distance) was observed (FIGS. 25F,G and 26A). The observed velocity in T cell inflamed, β-catenin-negative tumors, is highly consistent with literature reported velocities for T cell engaging cell contract in the presence of antigen. In contrast, the observation that T cells in β-catenin-positive tumor are not motile was unexpected, since an increase in T cell motility due to a lack of TCR engagement would have been predicted. In addition to the changes in motility of T cells, it was also observed that T cells in β-catenin-negative tumors show a close engagement with tumor cells, while in β-catenin-positive BPC-SIY tumors this close engagement was largely missing. The distance between the center of each T cell and the edge of the nearest tumor cells was assessed (FIG. 26B). Although outliers were observed, in either cohort of analyzed mice, a highly significant difference in the median distance of T cells to tumor cells was observed (FIG. 25H). While most effector T cell in (β-catenin-negative tumors were in direct engagement with tumor cells (median distance 5.97 μm, median radius of effector T cell 6 μm), most of the T cells found in β-catenin-positive tumors showed no direct contact (median distance 16.65 μm). This result indicates that additional, proximal tumor-specific mechanisms are preventing the effector T cells to engage close contact with β-catenin-positive tumor cells while contact with β-catenin-negative tumor cells occurs very frequently. All of these observations coincide with the observation that individual β-catenin-negative tumor lesions can be fully eradicated by adoptively transferred tumor cells (2/10) or stalled in expansion, while this phenomena was not observed in β-catenin-positive lesions (0/10). A representative example of the process of a successful eradication of a single tumor lesion is demonstrated in FIG. 26C.

All publications and patents provided herein are incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

REFERENCES

The following references are herein incorporated by reference in their entireties:

Kaufman, H. L. et al. The Society for Immunotherapy of Cancer consensus statement on tumor immunotherapy for the treatment of cutaneous melanoma. *Nature Reviews. Clinical Oncology* 10, 588-598, doi:10.1038/nrclinonc.2013.153 (2013).

Mellman, I., Coukos, G. & Dranoff, G. Cancer immunotherapy comes of age. *Nature* 480, 480-489, doi:10.1038/nature10673 (2011).

Wolchok, J. D. et al. Nivolumab plus ipilimumab in advanced melanoma. *The New England Journal of Medicine* 369, 122-133, doi:10.1056/NEJMoa1302369 (2013).

Topalian, S. L. et al. Survival, durable tumor remission, and long-term safety in patients with advanced melanoma receiving nivolumab. *Journal of Clinical Oncology: Official Journal of the American Society of Clinical Oncology* 32, 1020-1030, doi:10.1200/JCO.2013.53.0105 (2014).

Topalian, S. L. et al. Safety, activity, and immune correlates of anti-PD-1 antibody in cancer. *The New England Journal of Medicine* 366, 2443-2454, doi:10.1056/NEJMoa1200690 (2012).

Hodi, F. S. et al. Improved survival with ipilimumab in patients with metastatic melanoma. *The New England Journal of Medicine* 363, 711-723, doi:10.1056/NEJMoa1003466 (2010).

Harlin, H. et al. Chemokine expression in melanoma metastases associated with CD8+ Tcell recruitment. *Cancer Research* 69, 3077-3085, doi:10.1158/0008-5472.CAN-08-2281 (2009).

Ji, R. R. et al. An immune-active tumor microenvironment favors clinical response to ipilimumab. *Cancer Immunology, Immunotherapy: CII* 61, 1019-1031, doi:10.1007/s00262-011-1172-6 (2012).

Gajewski, T. F., Louahed, J. & Brichard, V. G. Gene signature in melanoma associated with clinical activity: a potential clue to unlock cancer immunotherapy. *Cancer Journal* 16, 399-403, doi:10.1097/PPO.0b013e3181eacbd8 (2010).

Dankort, D. et al. Braf(V600E) cooperates with Pten loss to induce metastatic melanoma. *Nature Genetics* 41, 544-552, doi:10.1038/ng.356 (2009).

Damsky, W. E. et al. beta-catenin signaling controls metastasis in Braf-activated Ptendeficient melanomas. *Cancer Cell* 20, 741-754, doi:10.1016/j.ccr.2011.10.030 (2011).

Gajewski, T. F., Schreiber, H. & Fu, Y. X. Innate and adaptive immune cells in the tumor microenvironment. *Nature Immunology* 14, 1014-1022, doi:10.1038/ni.2703 (2013).

Galon, J. et al. Type, density, and location of immune cells within human colorectal tumors predict clinical outcome. *Science* 313, 1960-1964, doi:10.1126/science.1129139 (2006).

Rimm, D. L., Caca, K., Hu, G., Harrison, F. B. & Fearon, E. R. Frequent nuclear/cytoplasmic localization of beta-catenin without exon 3 mutations in malignant melanoma. *The American Journal of Pathology* 154, 325-329 (1999).

Herbst, A. et al. Comprehensive analysis of beta-catenin target genes in colorectal carcinoma cell lines with deregulated Wnt/beta-catenin signaling. *BMC Genomics* 15, 74, doi:10.1186/1471-2164-15-74 (2014).

Spranger, S. et al. Up-regulation of PD-L1, IDO, and T(regs) in the melanoma tumor microenvironment is driven by CD8(+) T cells. *Science Translational Medicine* 5, 200ra116, doi:10.1126/scitranslmed.3006504 (2013).

Bosenberg, M. et al. Characterization of melanocyte-specific inducible Cre recombinase transgenic mice. *Genesis* 44, 262-267, doi:10.1002/dvg.20205 (2006).

Dankort, D. et al. A new mouse model to explore the initiation, progression, and therapy of BRAFV600E-induced lung tumors. *Genes & Development* 21, 379-384, doi:10.1101/gad.1516407 (2007).

Suzuki, A. et al. High cancer susceptibility and embryonic lethality associated with mutation of the PTEN tumor suppressor gene in mice. *Current Biology:CB* 8, 1169-1178 (1998).

Gounari, F. et al. Stabilization of beta-catenin induces lesions reminiscent of prostatic intraepithelial neoplasia, but terminal squamous transdifferentiation of other secretory epithelia. *Oncogene* 21, 4099-4107, doi:10.1038/sj.onc.1205562 (2002).

Harada, N. et al. Intestinal polyposis in mice with a dominant stable mutation of the betacatenin gene. *The EMBO Journal* 18, 5931-5942, doi:10.1093/emboj/18.21.5931 (1999).

Woo, S. R. et al. Immune inhibitory molecules LAG-3 and PD-1 synergistically regulate T-cell function to promote tumoral immune escape. *Cancer Res* 72, 917-927, doi:10.1158/0008-5472. CAN-11-1620-0008-5472. CAN-11-1620 [pii] (2012).

Landsberg, J. et al. Melanomas resist T-cell therapy through inflammation-induced reversible dedifferentiation. *Nature* 490, 412-416, doi:10.1038/nature11538 (2012).

Soudja, S. M. et al. Tumor-initiated inflammation overrides protective adaptive immunity in an induced melanoma model in mice. *Cancer Research* 70, 3515-3525, doi:10.1158/0008-5472.CAN-09-4354 (2010).

Matsushita, H. et al. Cancer exome analysis reveals a T-cell-dependent mechanism of cancer immunoediting. *Nature* 482, 400-404, doi:10.1038/nature10755 (2012).

Cheung, A. F., Dupage, M. J., Dong, H. K., Chen, J. & Jacks, T. Regulated expression of a tumor-associated antigen reveals multiple levels of T-cell tolerance in a mouse model of lung cancer. *Cancer Research* 68, 9459-9468, doi:10.1158/0008-5472.CAN-08-2634 (2008).

DuPage, M. et al. Endogenous T cell responses to antigens expressed in lung adenocarcinomas delay malignant tumor progression. *Cancer Cell* 19, 72-85, doi:10.1016/j.ccr.2010.11.011 (2011).

Fuertes, M. B. et al. Host type I IFN signals are required for antitumor CD8+ T cell responses through CD8{alpha}+ dendritic cells. *The Journal of Experimental Medicine* 208, 2005-2016, doi:10.1084/jem.20101159 (2011).

Hildner, K. et al. Batf3 deficiency reveals a critical role for CD8alpha+ dendritic cells in cytotoxic T cell immunity. *Science* 322, 1097-1100, doi:10.1126/science.1164206 (2008).

Engelhardt, J. J. et al. Marginating dendritic cells of the tumor microenvironment crosspresent tumor antigens and stably engage tumor-specific T cells. *Cancer Cell* 21, 402-417, doi:10.1016/j.ccr.2012.01.008 (2012).

Bedoui, S. et al. Cross-presentation of viral and self antigens by skin-derived CD103+ dendritic cells. *Nature Immunology* 10, 488-495, doi:10.1038/ni.1724 (2009).

Edelson, B. T. et al. Peripheral CD103+ dendritic cells form a unified subset developmentally related to CD8alpha+ conventional dendritic cells. *The Journal of Experimental Medicine* 207, 823-836, doi:10.1084/jem.20091627 (2010).

Mollah, S. A. et al. Flt3L dependence helps define an uncharacterized subset of murine cutaneous dendritic cells. *The Journal of Investigative Dermatology* 134, 1265-1275, doi:10.1038/jid.2013.515 (2014).

Bald, T. et al. Immune cell-poor melanomas benefit from PD-1 blockade after targeted type I IFN activation. *Cancer Discovery* 4, 674-687, doi:10.1158/2159-8290.CD-13-0458 (2014).

Malissen, B., Tamoutounour, S. & Henri, S. The origins and functions of dendritic cells and macrophages in the skin. *Nature Reviews. Immunology* 14, 417-428, doi:10.1038/nri3683 (2014).

Aliberti, J. et al. CCR5 provides a signal for microbial induced production of IL-12 by CD8 alpha+ dendritic cells. *Nature Immunology* 1, 83-87, doi:10.1038/76957 (2000).

Salerno, E. P., Olson, W. C., McSkimming, C., Shea, S. & Slingluff, C. L., Jr. T cells in the human metastatic melanoma microenvironment express site-specific homing receptors and retention integrins. *International Journal of Cancer. Journal International du Cancer* 134, 563-574, doi:10.1002/ijc.28391 (2014).

Peng, W. et al. PD-1 blockade enhances T-cell migration to tumors by elevating IFNgamma inducible chemokines. *Cancer Research* 72, 5209-5218, doi:10.1158/0008-5472.CAN-12-1187 (2012).

Li, Y. et al. N-myc downstream-regulated gene 2, a novel estrogen-targeted gene, is involved in the regulation of Na+/K+-ATPase. *The Journal of Biological Chemistry* 286, 32289-32299, doi:10.1074/jbc.M111.247825 (2011).

Khuu, C. H., Barrozo, R. M., Hai, T. & Weinstein, S. L. Activating transcription factor 3 (ATF3) represses the expression of CCL4 in murine macrophages. *Molecular Immunology* 44, 1598-1605, doi:10.1016/j.molimm.2006.08.006 (2007).

Jongbloed, S. L. et al. Human CD141+ (BDCA-3)+ dendritic cells (DCs) represent a unique myeloid DC subset that cross-presents necrotic cell antigens. *The Journal of Experimental Medicine* 207, 1247-1260, doi: 10.1084/jem.20092140 (2010).

Spranger, S. et al. Mechanism of tumor rejection with doublets of CTLA-4, PD-1/PD-L1, or IDO blockade involves restored IL-2 production and proliferation of CD8+ T cells directly within the tumor microenvironment. *Journal of ImmunoTherapy of Cancer* 2 (2014).

Yaguchi, T. et al. Immune suppression and resistance mediated by constitutive activation of Wnt/beta-catenin signaling in human melanoma cells. *Journal of Immunology* 189, 2110-2117, doi:10.4049/jimmunol.1102282 (2012).

Chien, A. J. et al. Activated Wnt/beta-catenin signaling in melanoma is associated with decreased proliferation in patient tumors and a murine melanoma model. *Proceedings of the National Academy of Sciences of the United States of America* 106, 1193-1198, doi:10.1073/pnas.0811902106 (2009).

Driessens, G. et al. Beta-catenin inhibits T cell activation by selective interference with linker for activation of T cells-phospholipase C-gammal phosphorylation. *Journal of Immunology* 186, 784-790, doi:10.4049/jimmunol.1001562 (2011).

Driessens, G., Zheng, Y. & Gajewski, T. F. Beta-catenin does not regulate memory T cell phenotype. *Nature Medicine* 16, 513-514; author reply 514-515, doi:10.1038/nm0510-513 (2010).

Cipponi, A., Wieers, G., van Baren, N. & Coulie, P. G. Tumor-infiltrating lymphocytes: apparently good for melanoma patients. But why? *Cancer Immunology, Immunotherapy: CII* 60, 1153-1160, doi:10.1007/s00262-011-1026-2 (2011).

Molon, B. et al. Chemokine nitration prevents intratumoral infiltration of antigen-specific T cells. *The Journal of Experimental Medicine* 208, 1949-1962, doi:10.1084/jem.20101956 (2011).

Sato, E. et al. Intraepithelial CD8+ tumor-infiltrating lymphocytes and a high CD8+/regulatory T cell ratio are associated with favorable prognosis in ovarian cancer. *Proceedings of the National Academy of Sciences of the United States of America* 102, 18538-18543, doi:10.1073/pnas.0509182102 (2005).

Nelson, B. H. The impact of T-cell immunity on ovarian cancer outcomes. *Immunological Reviews* 222, 101-116, doi:10.1111/j.1600-065X.2008.00614.x (2008).

Li, B. & Dewey, C. N. RSEM: accurate transcript quantification from RNA-Seq data with or without a reference genome. *BMC Bioinformatics* 12, 323, doi:10.1186/1471-2105-12-323 (2011).

Wilkerson, M. D. & Hayes, D. N. ConsensusClusterPlus: a class discovery tool with confidence assessments and item tracking. *Bioinformatics* 26, 1572-1573, doi:10.1093/bioinformatics/btq170 (2010).

Wang, K., Li, M. & Hakonarson, H. ANNOVAR: functional annotation of genetic variants from high-throughput sequencing data. *Nucleic Acids Research* 38, e164, doi: 10.1093/nar/gkq603 (2010).

Genomes Project, C. et al. An integrated map of genetic variation from 1,092 human genomes. *Nature* 491, 56-65, doi:10.1038/nature11632 (2012).

Jensen, L. J. et al. STRING 8—a global view on proteins and their functional interactions in 630 organisms. *Nucleic Acids Research* 37, D412-416, doi:10.1093/nar/gkn760 (2009).

Jeong, J., Mao, J., Tenzen, T., Kottmann, A. H. & McMahon, A. P. Hedgehog signaling in the neural crest cells regulates the patterning and growth of facial primordia. *Genes & Development* 18, 937-951, doi:10.1101/gad.1190304 (2004).

Manning, T. C. et al. Antigen recognition and allogeneic tumor rejection in CD8+ TCR transgenic/RAG(-/-) mice. *Journal of Immunology* 159, 4665-4675 (1997).

Erdag, G. et al. Immunotype and immunohistologic characteristics of tumor-infiltrating immune cells are associated with clinical outcome in metastatic melanoma. *Cancer Research* 72, 1070-1080, doi:10.1158/0008-5472.CAN-11-3218 (2012).

Schmittgen, T. D. & Livak, K. J. Analyzing real-time PCR data by the comparative C(T) method. *Nature Protocols* 3, 1101-1108 (2008).

Spranger, S. et al. Generation of Th1-polarizing dendritic cells using the TLR7/8 agonist CL075. *Journal of Immunology* 185, 738-747, doi:10.4049/jimmunol.1000060 (2010).

The invention claimed is:

1. A method for the treatment of solid tumor cancer in a subject comprising;
   (a) testing tumor cells or tissue from the subject for one or more of:
      (i) exclusion of T cell infiltration,
      (ii) transcriptional repression of chemokine CCL4,
      (iii) defective recruitment of CD103$^+$ dermal dendritic cells; and
   (b) administering a β-catenin inhibitor and/or a Wnt/β-catenin pathway inhibitor to the subject.

2. The method of claim 1, wherein the subject suffers from melanoma.

3. The method of claim 1, wherein the subject has one or more tumors exhibiting tumor-intrinsic-β-catenin-signaling.

4. The method of claim 3, further comprising a step of testing the subject, a tumor, or a tumor cell for β-catenin signaling.

5. The method of claim 1, wherein the β-catenin inhibitor and/or β-catenin pathway inhibitor is selected from a group consisting of a small molecule, a peptide, a polypeptide, a nucleic acid, an antibody, and an antibody fragment.

6. The method of claim 1, further comprising co-administration of an additional therapeutic agent.

7. The method of claim 6, wherein the additional therapeutic agent is a chemotherapeutic or an immunotherapeutic agent.

8. The method of claim 7, wherein the additional therapeutic agent is an immunotherapeutic agent selected from the list consisting of cell-based therapies, monoclonal antibody (mAb) therapy, cytokine therapy, and adjuvant treatment.

9. The method of claim 8, wherein the immunotherapeutic agent is a mAb therapy selected from the list consisting of anti-CTLA-4 monoclonal antibodies and/or anti-PD-L1 monoclonal antibodies.

10. The method of claim 8, wherein the immunotherapeutic agent is a cell-based therapy selected from the list consisting of dendritic-cell therapy and T-cell therapy.

11. The method of claim 1, further comprising:
    testing tumor cells or tissue from the subject for one or more of:
       (iv) tumor-intrinsic-β-catenin-signaling, and
       (v) activation of CD8$^+$ T cells.

12. The method of claim 11, further comprising surgical, radiation, and/or chemotherapeutic cancer intervention.

13. The method of claim 11, further comprising:
    retesting the subject for one or more of (i) through (v).

14. The method of claim 13, wherein if the subject retests negative for one or more of (i) through (v) that were positive in an initial test, an immunotherapeutic agent is administered to the subject.

15. The method of claim 11, further comprising testing the subject for one or more additional cancer biomarkers.

* * * * *